United States Patent
Yoon et al.

(10) Patent No.: US 12,139,530 B2
(45) Date of Patent: Nov. 12, 2024

(54) BISPECIFIC ANTIBODY SPECIFICALLY BINDING TO IL-17A AND TNF-α

(71) Applicant: Y-BIOLOGICS INC., Daejeon (KR)

(72) Inventors: Jae Bong Yoon, Daejeon (KR); Eun Young Jeon, Daejeon (KR); Gi Sun Baek, Daejeon (KR); Seok Ho Yoo, Daejeon (KR); Bum-Chan Park, Daejeon (KR); Young Woo Park, Daejeon (KR)

(73) Assignee: Y-BIOLOGICS INC., Daejeon (KR)

( * ) Notice: Subject to any disclaimer, the term of this patent is extended or adjusted under 35 U.S.C. 154(b) by 703 days.

(21) Appl. No.: 17/430,144

(22) PCT Filed: Apr. 20, 2020

(86) PCT No.: PCT/KR2020/005213
§ 371 (c)(1),
(2) Date: Aug. 11, 2021

(87) PCT Pub. No.: WO2020/218791
PCT Pub. Date: Oct. 29, 2020

(65) Prior Publication Data
US 2022/0098297 A1 Mar. 31, 2022

(30) Foreign Application Priority Data
Apr. 26, 2019 (KR) .................. 10-2019-0049177

(51) Int. Cl.
| C07K 16/24 | (2006.01) |
| A61K 39/00 | (2006.01) |
| A61K 47/68 | (2017.01) |
| A61P 37/06 | (2006.01) |
| C12N 5/00 | (2006.01) |
| C12N 15/85 | (2006.01) |

(52) U.S. Cl.
CPC ........ *C07K 16/244* (2013.01); *A61K 47/6845* (2017.08); *A61P 37/06* (2018.01); *C07K 16/241* (2013.01); *C12N 5/0018* (2013.01); *C12N 15/85* (2013.01); *A61K 2039/5156* (2013.01); *C07K 2317/31* (2013.01); *C07K 2317/565* (2013.01); *C07K 2317/567* (2013.01); *C12N 2800/107* (2013.01)

(58) Field of Classification Search
CPC .......................... C07K 16/244; C07K 16/241; C07K 2317/31; C07K 2317/565; C07K 2317/567; C07K 2317/56; C07K 2317/622; C07K 2317/76; C07K 2317/92; C07K 16/461; A61K 47/6845; A61K 2039/5156; A61K 2039/55; A61K 47/6801; A61K 2039/505; A61P 37/06; A61P 1/00; A61P 9/14; A61P 13/12; A61P 17/06; A61P 37/02; A61P 37/00; A61P 19/02; A61P 19/08; A61P 25/00; A61P 27/02; A61P 29/00; C12N 5/0018; C12N 15/85; C12N 2800/107
See application file for complete search history.

(56) References Cited

U.S. PATENT DOCUMENTS

| 5,656,272 A | 8/1997 | Le et al. |
| 2014/0255406 A1 | 9/2014 | Allan et al. |
| 2015/0147327 A1 | 5/2015 | Wu et al. |
| 2017/0218092 A1 | 8/2017 | Chiu et al. |

FOREIGN PATENT DOCUMENTS

| WO | WO 97/29131 A1 | 8/1997 |
| WO | WO 01/94585 A1 | 12/2001 |
| WO | WO 2007/028106 A2 | 3/2007 |
| WO | WO 2009/149189 A2 | 12/2009 |
| WO | WO 2014/189306 A1 | 11/2014 |
| WO | WO 2015/014979 A1 | 2/2015 |
| WO | WO 2017/123556 A1 | 7/2017 |
| WO | WO 2019/093807 A2 | 5/2019 |

OTHER PUBLICATIONS

European Search Report For EP20795896.8 issued on Aug. 2, 2022 from European patent office in a counterpart European patent application.
Office action issued on Aug. 8, 2022 from Japan Intellectual Property Office in a counterpart Japanese Patent Application No. 2021-546752 (all the cited references are listed in this IDS.) (English translation is also submitted herewith.).
Michela Silacci et al., "Discovery and characterization of COVA322, a clinical-stage bispecific TNF/IL-17A inhibitor for the treatment of inflammatory diseases", mAbs, 2016, vol. 8, No. 1, pp. 141-149.
Tianshu Xu et al., "A native-like bispecific antibody suppresses the inflammatory cytokine response by simultaneously neutralizing tumor necrosis factor-alpha and interleukin-17A", Oncotarget, 2017, vol. 8, No. 47, pp. 81860-81872, doi: 10.18632/oncotarget.19899.
International Search Report for PCT/KR2020/005213 mailed on Sep. 8, 2020.
George E. Gifford et al., "Introduction to TNF and related lymphokines", Biotherapy, vol. 3, pp. 103-111, 1991.
M Feldmann et al., "Role of cytokines in rheumatoid arthritis", Annu Rev Immunol. 14:397-440, 1996 (Abstract is submitted herewith.).
W J Sandborn et al., "Antitumor necrosis factor therapy for inflammatory bowel disease: a review of agents, pharmacology, clinical results, and safety", Inflamm Bowel Dis. 5(2): 119-33, 1999 (Abstract is submitted herewith.).

(Continued)

*Primary Examiner* — Brad Duffy
*Assistant Examiner* — Amber K Faust
(74) *Attorney, Agent, or Firm* — The PL Law Group, PLLC

(57) ABSTRACT

A bispecific antibody according to an embodiment of the present disclosure specifically binds to IL-17A and TNF-α. The bispecific antibody according to the present invention or an antigen binding fragment thereof exhibits high specificity for IL-17A and TNF-α and more favorable neutralization property compared to monospecific antibody of a prior art, and, by quickly suppressing inflammation and an immune response by inhibiting simultaneously IL-17 and TNF-α, it has an advantage of improving the treatment effect with lower dose.

21 Claims, 17 Drawing Sheets
Specification includes a Sequence Listing.

(56) References Cited

OTHER PUBLICATIONS

M H Buch et al., "Long-term infliximab treatment in rheumatoid arthritis: subsequent outcome of initial responders", Rheumatology (Oxford). 46(7):1153-6, 2007 (Abstract is submitted herewith.).
A Finckh et al., "Evidence for differential acquired drug resistance to antitumour necrosis factor agents in rheumatoid arthritis", Ann Rheum Dis. 65(6):746-52, 2006 (Abstract is submitted herewith.).
F Fossiez et al., "T cell interleukin-17 induces stromal cells to produce proinflammatory and hematopoietic cytokines", J Exp Med. 1;183(6):2593-603, 1996 (Abstract is submitted herewith.).
Andrea Chiricozzi et al., "Integrative responses to IL-17 and TNF-α in human keratinocytes account for key Inflammatory pathogenic circuits in psoriasis", J Invest Dermatol. 131(3):677-87, 2011 (Abstract is submitted herewith.).
Pierre Miossec, M.D., Ph.D., et al., "Interleukin-17 and Type 17 Helper T Cells", N Engl J Med. 27;361(9):888-98, 2009.
David A Martin et al., "The emerging role of IL-17 in the pathogenesis of psoriasis: preclinical and clinical findings", J Invest Dermatol. 133(1):17-26, 2013 (Abstract is submitted herewith.).
Joachim Sieper, "New treatment targets for axial spondyloarthritis", Rheumatology (Oxford). 55, ii38-ii42, 2016.
Denis Poddubnyy et al., "What is the best treatment target in axial spondyloarthritis: tumour necrosis factor a, interleukin 17, or both?", Rheumatology 2018, vol. 57:1145-150 (Advance Access publication Oct. 12, 2017).

SEQUENCE LISTING

```
<160> NUMBER OF SEQ ID NOS: 89

<210> SEQ ID NO 1
<211> LENGTH: 5
<212> TYPE: PRT
<213> ORGANISM: Artificial Sequence
<220> FEATURE:
<223> OTHER INFORMATION: H-CDR1

<400> SEQUENCE: 1

Ser Tyr Thr Met His
1               5

<210> SEQ ID NO 2
<211> LENGTH: 16
<212> TYPE: PRT
<213> ORGANISM: Artificial Sequence
<220> FEATURE:
<223> OTHER INFORMATION: H-CDR2

<400> SEQUENCE: 2

Ile Ser Phe Asp Gly Arg Ser Lys Leu Tyr Gly Asp Ser Val Arg Asp
1               5                   10                  15

<210> SEQ ID NO 3
<211> LENGTH: 11
```

```
<212> TYPE: PRT
<213> ORGANISM: Artificial Sequence
<220> FEATURE:
<223> OTHER INFORMATION: H-CDR3

<400> SEQUENCE: 3

Arg Gly Arg Glu Gly Glu Asp Ala Phe Asp Leu
1               5                   10

<210> SEQ ID NO 4
<211> LENGTH: 16
<212> TYPE: PRT
<213> ORGANISM: Artificial Sequence
<220> FEATURE:
<223> OTHER INFORMATION: H-CDR2

<400> SEQUENCE: 4

Ile Ser Phe Asp Gly Arg Ser Lys Leu Tyr Gly Asp Ser Val Lys Gly
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: H-CDR3

<400> SEQUENCE: 5

Gly Ser Val Arg Gly Glu Ala Ala Phe Asp Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: H-CDR3

<400> SEQUENCE: 6

Gly Ser Lys Leu Gly Glu Asp Ala Phe Asp Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: H-CDR3

<400> SEQUENCE: 7

Gly Ser Arg Ile Gly Glu Asp Ala Phe Asp Leu
1               5                   10

<210> SEQ ID NO 8
<211> LENGTH: 5
<212> TYPE: PRT
<213> ORGANISM: Artificial Sequence
<220> FEATURE:
<223> OTHER INFORMATION: H-CDR1

<400> SEQUENCE: 8

Asp His Ala Met His
1               5

<210> SEQ ID NO 9
<211> LENGTH: 18
<212> TYPE: PRT
```

```
<213> ORGANISM: Artificial Sequence
<220> FEATURE:
<223> OTHER INFORMATION: H-CDR2

<400> SEQUENCE: 9

Ser Leu Ile Ser Gly Asp Gly Gly Ala Thr Tyr Tyr Ala Asp Ser Val
1               5                   10                  15

Lys Gly

<210> SEQ ID NO 10
<211> LENGTH: 15
<212> TYPE: PRT
<213> ORGANISM: Artificial Sequence
<220> FEATURE:
<223> OTHER INFORMATION: H-CDR3

<400> SEQUENCE: 10

His Phe Ser Asp Ser Arg Gly Arg Ser Asp Val Pro Phe Asp Ile
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: H-CDR2

<400> SEQUENCE: 11

Gly Leu Ile Gly Pro Asp Gly Gly Ala Thr Tyr Tyr Ala Asp Ser Val
1               5                   10                  15

Lys Gly

<210> SEQ ID NO 12
<211> LENGTH: 11
<212> TYPE: PRT
<213> ORGANISM: Artificial Sequence
<220> FEATURE:
<223> OTHER INFORMATION: L-CDR1

<400> SEQUENCE: 12

Ser Gly Asp Asn Leu Arg Thr Lys Tyr Val Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: L-CDR2

<400> SEQUENCE: 13

Gln Asp Thr Arg Arg Pro Ser
1               5

<210> SEQ ID NO 14
<211> LENGTH: 10
<212> TYPE: PRT
<213> ORGANISM: Artificial Sequence
<220> FEATURE:
<223> OTHER INFORMATION: L-CDR3

<400> SEQUENCE: 14

Met Thr Trp Asp Val Asp Thr Thr Ser Met
1               5                   10
```

<210> SEQ ID NO 15
<211> LENGTH: 30
<212> TYPE: PRT
<213> ORGANISM: Artificial Sequence
<220> FEATURE:
<223> OTHER INFORMATION: FR1

<400> SEQUENCE: 15

Gln Val Gln Leu Val Glu Ser Gly Gly Gly Val Ala Gln Pro Gly Arg
1               5                   10                  15

Ser Leu Arg Leu Ser Cys Ala Ala Ser Gly Phe Ala Phe Gly
            20                  25                  30

<210> SEQ ID NO 16
<211> LENGTH: 15
<212> TYPE: PRT
<213> ORGANISM: Artificial Sequence
<220> FEATURE:
<223> OTHER INFORMATION: FR2

<400> SEQUENCE: 16

Trp Val Arg Gln Ala Pro Gly Lys Gly Leu Glu Trp Val Thr Leu
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: FR3

<400> SEQUENCE: 17

Arg Phe Thr Ile Ser Arg Asp Asn Ser Lys Asn Met Leu Tyr Leu Lys
1               5                   10                  15

Ile Ser Asp Leu Arg Ser Glu Asp Thr Ala Val Tyr Tyr Cys Ala Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: FR4

<400> SEQUENCE: 18

Trp Gly Gln Gly Thr Met Val Thr Val Ser Ser
1               5                   10

<210> SEQ ID NO 19
<211> LENGTH: 30
<212> TYPE: PRT
<213> ORGANISM: Artificial Sequence
<220> FEATURE:
<223> OTHER INFORMATION: FR1

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Gly
            20                  25                  30

<210> SEQ ID NO 20
<211> LENGTH: 32
<212> TYPE: PRT
<213> ORGANISM: Artificial Sequence
<220> FEATURE:

-continued

<223> OTHER INFORMATION: FR3

<400> SEQUENCE: 20

Arg Phe Thr Ile Ser Arg Asp Asn Ser Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 21
<211> LENGTH: 11
<212> TYPE: PRT
<213> ORGANISM: Artificial Sequence
<220> FEATURE:
<223> OTHER INFORMATION: FR4

<400> SEQUENCE: 21

Trp Gly Gln Gly Thr Leu Val Thr Val Ser Ser
1               5                   10

<210> SEQ ID NO 22
<211> LENGTH: 30
<212> TYPE: PRT
<213> ORGANISM: Artificial Sequence
<220> FEATURE:
<223> OTHER INFORMATION: FR1

<400> SEQUENCE: 22

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp
            20                  25                  30

<210> SEQ ID NO 23
<211> LENGTH: 13
<212> TYPE: PRT
<213> ORGANISM: Artificial Sequence
<220> FEATURE:
<223> OTHER INFORMATION: FR2

<400> SEQUENCE: 23

Trp Val Arg Gln Ala Pro Gly Lys Gly Leu Glu Trp Val
1               5                   10

<210> SEQ ID NO 24
<211> LENGTH: 32
<212> TYPE: PRT
<213> ORGANISM: Artificial Sequence
<220> FEATURE:
<223> OTHER INFORMATION: FR3

<400> SEQUENCE: 24

Arg Phe Ile Ile Ser Arg Asp Asn Ser Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 25
<211> LENGTH: 11
<212> TYPE: PRT
<213> ORGANISM: Artificial Sequence
<220> FEATURE:
<223> OTHER INFORMATION: FR4

<400> SEQUENCE: 25

Trp Gly Gln Gly Thr Leu Ile Thr Val Ser Ser

```
1               5                   10

<210> SEQ ID NO 26
<211> LENGTH: 13
<212> TYPE: PRT
<213> ORGANISM: Artificial Sequence
<220> FEATURE:
<223> OTHER INFORMATION: FR2

<400> SEQUENCE: 26

Trp Val Arg Gln Ala Pro Gly Asn Gly Leu Glu Trp Val
1               5                   10

<210> SEQ ID NO 27
<211> LENGTH: 22
<212> TYPE: PRT
<213> ORGANISM: Artificial Sequence
<220> FEATURE:
<223> OTHER INFORMATION: FR1

<400> SEQUENCE: 27

Ser Tyr Glu Leu Thr Gln Ala Pro Ser Leu Ser Val Ser Pro Gly Gln
1               5                   10                  15

Thr Ala Asn Ile Ile Cys
            20

<210> SEQ ID NO 28
<211> LENGTH: 15
<212> TYPE: PRT
<213> ORGANISM: Artificial Sequence
<220> FEATURE:
<223> OTHER INFORMATION: FR2

<400> SEQUENCE: 28

Trp Tyr Gln Gln Lys Pro Gly Gln Ser Pro Leu Leu Val Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: FR3

<400> SEQUENCE: 29

Gly Ile Pro Ala Arg Phe Ser Gly Ser Asn Ser Gly Asn Thr Ala Thr
1               5                   10                  15

Leu Thr Ile Ser Gly Thr Gln Thr Arg Asp Glu Ser Tyr Tyr Cys
            20                  25                  30

<210> SEQ ID NO 30
<211> LENGTH: 11
<212> TYPE: PRT
<213> ORGANISM: Artificial Sequence
<220> FEATURE:
<223> OTHER INFORMATION: FR4

<400> SEQUENCE: 30

Ile Phe Gly Gly Gly Thr Lys Leu Thr Val Leu
1               5                   10

<210> SEQ ID NO 31
<211> LENGTH: 22
<212> TYPE: PRT
<213> ORGANISM: Artificial Sequence
<220> FEATURE:
```

```
<223> OTHER INFORMATION: FR1

<400> SEQUENCE: 31

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: FR2

<400> SEQUENCE: 32

Trp Tyr Gln Gln Lys Pro Gly Gln Ser Pro Val Leu Val Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: FR3

<400> SEQUENCE: 33

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 34
<211> LENGTH: 120
<212> TYPE: PRT
<213> ORGANISM: Artificial Sequence
<220> FEATURE:
<223> OTHER INFORMATION: VH

<400> SEQUENCE: 34

Gln Val Gln Leu Val Glu Ser Gly Gly Val Ala Gln Pro Gly Arg
1               5                   10                  15

Ser Leu Arg Leu Ser Cys Ala Ala Ser Gly Phe Ala Phe Gly Ser Tyr
            20                  25                  30

Thr Met His Trp Val Arg Gln Ala Pro Gly Lys Gly Leu Glu Trp Val
        35                  40                  45

Thr Leu Ile Ser Phe Asp Gly Arg Ser Lys Leu Tyr Gly Asp Ser Val
    50                  55                  60

Arg Asp Arg Phe Thr Ile Ser Arg Asp Asn Ser Lys Asn Met Leu Tyr
65                  70                  75                  80

Leu Lys Ile Ser Asp Leu Arg Ser Glu Asp Thr Ala Val Tyr Tyr Cys
                85                  90                  95

Ala Arg Arg Gly Arg Glu Gly Glu Asp Ala Phe Asp Leu Trp Gly Gln
            100                 105                 110

Gly Thr Met Val Thr Val Ser Ser
        115                 120

<210> SEQ ID NO 35
<211> LENGTH: 120
<212> TYPE: PRT
<213> ORGANISM: Artificial Sequence
<220> FEATURE:
```

<223> OTHER INFORMATION: VH

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Gly Ser Tyr
            20                  25                  30

Thr Met His Trp Val Arg Gln Ala Pro Gly Lys Gly Leu Glu Trp Val
        35                  40                  45

Thr Leu Ile Ser Phe Asp Gly Arg Ser Lys Leu Tyr Gly Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Val Arg Gly Glu Ala Ala Phe Asp Leu Trp Gly Gln
            100                 105                 110

Gly Thr Leu Val Thr Val Ser Ser
            115                 120

<210> SEQ ID NO 36
<211> LENGTH: 120
<212> TYPE: PRT
<213> ORGANISM: Artificial Sequence
<220> FEATURE:
<223> OTHER INFORMATION: VH

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Gly Ser Tyr
            20                  25                  30

Thr Met His Trp Val Arg Gln Ala Pro Gly Lys Gly Leu Glu Trp Val
        35                  40                  45

Thr Leu Ile Ser Phe Asp Gly Arg Ser Lys Leu Tyr Gly Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Lys Leu Gly Glu Asp Ala Phe Asp Leu Trp Gly Gln
            100                 105                 110

Gly Thr Leu Val Thr Val Ser Ser
            115                 120

<210> SEQ ID NO 37
<211> LENGTH: 120
<212> TYPE: PRT
<213> ORGANISM: Artificial Sequence
<220> FEATURE:
<223> OTHER INFORMATION: VH

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Gly Ser Tyr
            20                  25                  30

Thr Met His Trp Val Arg Gln Ala Pro Gly Lys Gly Leu Glu Trp Val

```
                35                  40                  45
Thr Leu Ile Ser Phe Asp Gly Arg Ser Lys Leu Tyr Gly Asp Ser Val
         50                  55                  60
Lys Gly Arg Phe Thr Ile Ser Arg Asp Asn Ser Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gly Ser Arg Ile Gly Glu Asp Ala Phe Asp Leu Trp Gly Gln
            100                 105                 110
Gly Thr Leu Val Thr Val Ser Ser
            115                 120

<210> SEQ ID NO 38
<211> LENGTH: 124
<212> TYPE: PRT
<213> ORGANISM: Artificial Sequence
<220> FEATURE:
<223> OTHER INFORMATION: VH

<400> SEQUENCE: 38

Gln Val Gln Leu Val Glu Ser Gly Gly Gly Val Val Gln Pro Gly Gly
 1               5                  10                  15
Ser Leu Arg Leu Ser Cys Ala Ala Ser Gly Phe Thr Phe Asp Asp His
                 20                  25                  30
Ala Met His Trp Val Arg Gln Ala Pro Gly Lys Gly Leu Glu Trp Val
            35                  40                  45
Ser Leu Ile Ser Gly Asp Gly Gly Ala Thr Tyr Tyr Ala Asp Ser Val
         50                  55                  60
Lys Gly Arg Phe Ile Ile Ser Arg Asp Asn Ser Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg His Phe Ser Asp Ser Arg Gly Arg Ser Asp Val Pro Phe Asp
            100                 105                 110
Ile Trp Gly Gln Gly Thr Leu Ile Thr Val Ser Ser
            115                 120

<210> SEQ ID NO 39
<211> LENGTH: 124
<212> TYPE: PRT
<213> ORGANISM: Artificial Sequence
<220> FEATURE:
<223> OTHER INFORMATION: VH

<400> SEQUENCE: 39

Gln Val Gln Leu Val Glu Ser Gly Gly Gly Val Val Gln Pro Gly Gly
 1               5                  10                  15
Ser Leu Arg Leu Ser Cys Ala Ala Ser Gly Phe Thr Phe Asp Asp His
                 20                  25                  30
Ala Met His Trp Val Arg Gln Ala Pro Gly Asn Gly Leu Glu Trp Val
            35                  40                  45
Gly Leu Ile Gly Pro Asp Gly Gly Ala Thr Tyr Tyr Ala Asp Ser Val
         50                  55                  60
Lys Gly Arg Phe Ile Ile Ser Arg Asp Asn Ser Lys Asn Ser Leu Tyr
 65                  70                  75                  80
Leu Gln Met Asn Ser Leu Arg Ala Glu Asp Thr Ala Val Tyr Tyr Cys
                 85                  90                  95
```

```
Ala Arg His Phe Ser Asp Ser Arg Gly Arg Ser Asp Val Pro Phe Asp
            100                 105                 110

Ile Trp Gly Gln Gly Thr Leu Ile Thr Val Ser Ser
        115                 120
```

<210> SEQ ID NO 40
<211> LENGTH: 108
<212> TYPE: PRT
<213> ORGANISM: Artificial Sequence
<220> FEATURE:
<223> OTHER INFORMATION: VL

<400> SEQUENCE: 40

```
Ser Tyr Glu Leu Thr Gln Ala Pro Ser Leu Ser Val Ser Pro Gly Gln
1               5                   10                  15

Thr Ala Asn Ile Ile Cys Ser Gly Asp Asn Leu Arg Thr Lys Tyr Val
            20                  25                  30

Ser Trp Tyr Gln Gln Lys Pro Gly Gln Ser Pro Leu Leu Val Ile Tyr
        35                  40                  45

Gln Asp Thr Arg Arg Pro Ser Gly Ile Pro Ala Arg Phe Ser Gly Ser
    50                  55                  60

Asn Ser Gly Asn Thr Ala Thr Leu Thr Ile Ser Gly Thr Gln Thr Arg
65                  70                  75                  80

Asp Glu Ser Thr Tyr Tyr Cys Met Thr Trp Asp Val Asp Thr Thr Ser
                85                  90                  95

Met Ile Phe Gly Gly Gly Thr Lys Leu Thr Val Leu
            100                 105
```

<210> SEQ ID NO 41
<211> LENGTH: 108
<212> TYPE: PRT
<213> ORGANISM: Artificial Sequence
<220> FEATURE:
<223> OTHER INFORMATION: VL

<400> SEQUENCE: 41

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Leu Arg Thr Lys Tyr Val
            20                  25                  30

Ser Trp Tyr Gln Gln Lys Pro Gly Gln Ser Pro Val Leu Val Ile Tyr
        35                  40                  45

Gln Asp Thr Arg Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Met Thr Trp Asp Val Asp Thr Thr Ser
                85                  90                  95

Met Ile Phe Gly Gly Gly Thr Lys Leu Thr Val Leu
            100                 105
```

<210> SEQ ID NO 42
<211> LENGTH: 360
<212> TYPE: DNA
<213> ORGANISM: Artificial Sequence
<220> FEATURE:
<223> OTHER INFORMATION: VH

<400> SEQUENCE: 42
caggtgcagc tggtggagtc tgggggaggc gtggcccagc ctggggaggtc cctcagactc    60

```
tcctgtgcag cctctggatt cgccttcggt agttacacta tgcactgggt ccgccaggcg      120
ccaggcaagg gactggagtg ggtgacactt atatcgtttg atggacgtag caagctttac      180
ggagactccg tgagggaccg attcaccatc tccagagaca attccaagaa catgctgtat      240
ctgaaaataa gtgacctgcg atctgaggac acggccgtgt attactgtgc gagacggggg      300
agggagggtg aagatgcttt cgatctctgg ggccaaggga caatggtcac cgtctcctca      360
```

<210> SEQ ID NO 43
<211> LENGTH: 360
<212> TYPE: DNA
<213> ORGANISM: Artificial Sequence
<220> FEATURE:
<223> OTHER INFORMATION: VH

<400> SEQUENCE: 43

```
caggtgcagc tggtggagtc tgggggaggc gtggtgcagc ctggagggtc cctcagactc      60
tcctgtgcag cctctggatt cgccttcggt agttacacta tgcactgggt ccgccaggcg      120
ccaggcaagg gactggagtg ggtgacactt atatcgtttg atggacgtag caagctttac      180
ggagactccg tgaagggccg attcaccatc tccagagaca attccaagaa cagcctgtat      240
ctgcagatga acagcctgcg agccgaggac acggccgtgt attactgtgc gagagggtct      300
gtgcggggtg aagctgcttt cgatctctgg ggccaaggga cactggtcac cgtctcctca      360
```

<210> SEQ ID NO 44
<211> LENGTH: 360
<212> TYPE: DNA
<213> ORGANISM: Artificial Sequence
<220> FEATURE:
<223> OTHER INFORMATION: VH

<400> SEQUENCE: 44

```
caggtgcagc tggtggagtc tgggggaggc gtggtgcagc ctggagggtc cctcagactc      60
tcctgtgcag cctctggatt cgccttcggt agttacacta tgcactgggt ccgccaggcg      120
ccaggcaagg gactggagtg ggtgacactt atatcgtttg atggacgtag caagctttac      180
ggagactccg tgaagggccg attcaccatc tccagagaca attccaagaa cagcctgtat      240
ctgcagatga acagcctgcg agccgaggac acggccgtgt attactgtgc gagagggagt      300
aagttgggtg aagatgcttt cgatctctgg ggccaaggga cactggtcac cgtctcctca      360
```

<210> SEQ ID NO 45
<211> LENGTH: 360
<212> TYPE: DNA
<213> ORGANISM: Artificial Sequence
<220> FEATURE:
<223> OTHER INFORMATION: VH

<400> SEQUENCE: 45

```
caggtgcagc tggtggagtc tgggggaggc gtggtgcagc ctggagggtc cctcagactc      60
tcctgtgcag cctctggatt cgccttcggt agttacacta tgcactgggt ccgccaggcg      120
ccaggcaagg gactggagtg ggtgacactt atatcgtttg atggacgtag caagctttac      180
ggagactccg tgaagggccg attcaccatc tccagagaca attccaagaa cagcctgtat      240
ctgcagatga acagcctgcg agccgaggac acggccgtgt attactgtgc gagaggttcg      300
cgtattggtg aagatgcttt cgatctctgg ggccaaggga cactggtcac cgtctcctca      360
```

<210> SEQ ID NO 46

```
<211> LENGTH: 372
<212> TYPE: DNA
<213> ORGANISM: Artificial Sequence
<220> FEATURE:
<223> OTHER INFORMATION: VH

<400> SEQUENCE: 46
caggtgcagc tggtggagtc tgggggaggc gtggtacagc ctggggggtc cctgagactc    60
tcctgtgcag cgtctggatt cacctttgat gatcatgcca tgcactgggt ccgtcaagct   120
ccagggaagg gtctggagtg ggtctctctt attagcggtg atggtggtgc cacatactat   180
gcagactctg tgaagggccg gttcatcatc tccagagaca acagcaaaaa ctccctgtat   240
ctgcaaatga acagtctgag agccgaggac acggccgtgt attactgtgc gagacatttt   300
tctgatagtc gtggtcgctc cgatgttcct tttgatatct ggggccaagg gacactgatc   360
accgtctcct ca                                                       372

<210> SEQ ID NO 47
<211> LENGTH: 372
<212> TYPE: DNA
<213> ORGANISM: Artificial Sequence
<220> FEATURE:
<223> OTHER INFORMATION: VH

<400> SEQUENCE: 47
caggtgcagc tggtggagtc tgggggaggc gtggtacagc ctggggggtc cctgagactc    60
tcctgtgcag cgtctggatt cacctttgat gatcatgcca tgcactgggt ccgtcaagct   120
ccagggaatg gtctggagtg ggtcggcctg attggtcctg atggtggtgc cacatactat   180
gcagactctg tgaagggccg gttcatcatc tccagagaca acagcaaaaa ctccctgtat   240
ctgcaaatga acagtctgag agccgaggac acggccgtgt attactgtgc gagacatttt   300
tctgatagtc gtggtcgctc cgatgttcct tttgatatct ggggccaagg gacactgatc   360
accgtctcct ca                                                       372

<210> SEQ ID NO 48
<211> LENGTH: 324
<212> TYPE: DNA
<213> ORGANISM: Artificial Sequence
<220> FEATURE:
<223> OTHER INFORMATION: VL

<400> SEQUENCE: 48
tcctatgagc tgacacaggc accctcactg tccgtgtcgc caggacagac agccaacatc    60
atctgctctg gagataactt gcgtactaaa tatgtttctt ggtatcagca gaagccaggc   120
cagtccccct tattggtcat ctatcaggac accaggcggc cctcaggcat ccctgcgcga   180
ttctcaggct ccaactcggg gaacacagcc actctgacca tcagcgggac ccagactaga   240
gatgaatcta cctattactg tatgacgtgg gacgtcgaca ctacctcgat gattttcggc   300
ggagggacca agctgaccgt ccta                                           324

<210> SEQ ID NO 49
<211> LENGTH: 324
<212> TYPE: DNA
<213> ORGANISM: Artificial Sequence
<220> FEATURE:
<223> OTHER INFORMATION: VL

<400> SEQUENCE: 49
tcctatgagc tgacacagcc cccctcagtg tccgtgtcgc caggacagac agccagcatc    60
```

```
acctgctctg agataaactt gcgtactaaa tatgtttctt ggtatcagca gaagccaggc    120
cagtcccctg tgttggtcat ctatcaggac accaggcggc cctcaggcat ccctgagcga    180
ttctcaggct ccaactcggg aacacagcc actctgacca tcagcgggac ccaggctatg    240
gatgaagctg actattactg tatgacgtgg gacgtcgaca ctacctcgat gattttcggc    300
ggagggacca agctgaccgt ccta                                           324
```

```
<210> SEQ ID NO 50
<211> LENGTH: 396
<212> TYPE: DNA
<213> ORGANISM: Artificial Sequence
<220> FEATURE:
<223> OTHER INFORMATION: hIL-17A

<400> SEQUENCE: 50
ggaatcacaa tcccacgaaa tccaggatgc ccaaattctg aggacaagaa cttccccgg     60 actgtgatgg tcaacctgaa catccataac cggaatacca ataccaatcc caaaaggtcc   120
tcagattact acaaccgatc cacctcacct tggaatctcc accgcaatga ggaccctgag   180
agatatccct ctgtgatctg ggaggcaaag tgccgccact tgggctgcat caacgctgat   240
gggaacgtgg actaccacat gaactctgtc cccatccagc aagagatcct ggtcctgcgc   300
agggagcctc cacactgccc caactccttc cggctggaga agatactggt gtccgtgggc   360
tgcacctgtg tcaccccgat tgtccaccat gtggcc                             396
```

```
<210> SEQ ID NO 51
<211> LENGTH: 420
<212> TYPE: DNA
<213> ORGANISM: Artificial Sequence
<220> FEATURE:
<223> OTHER INFORMATION: IL-17A-His

<400> SEQUENCE: 51
ggaatcacaa tcccacgaaa tccaggatgc ccaaattctg aggacaagaa cttccccgg     60 actgtgatgg tcaacctgaa catccataac cggaatacca ataccaatcc caaaaggtcc   120
tcagattact acaaccgatc cacctcacct tggaatctcc accgcaatga ggaccctgag   180
agatatccct ctgtgatctg ggaggcaaag tgccgccact tgggctgcat caacgctgat   240
gggaacgtgg actaccacat gaactctgtc cccatccagc aagagatcct ggtcctgcgc   300
agggagcctc cacactgccc caactccttc cggctggaga agatactggt gtccgtgggc   360
tgcacctgtg tcaccccgat tgtccaccat gtggcccatc atcatcatca tcaccatcac   420
```

```
<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
ggaatcacaa tcccacgaaa t                                              21
```

```
<210> SEQ ID NO 53
<211> LENGTH: 21
<212> TYPE: DNA
<213> ORGANISM: Artificial Sequence
<220> FEATURE:
<223> OTHER INFORMATION: Primer
```

```
<400> SEQUENCE: 53
ggccacatgg tggacaatcg g                                    21

<210> SEQ ID NO 54
<211> LENGTH: 5
<212> TYPE: PRT
<213> ORGANISM: Artificial Sequence
<220> FEATURE:
<223> OTHER INFORMATION: H-CDR1

<400> SEQUENCE: 54

Asp Tyr Ala Met His
1               5

<210> SEQ ID NO 55
<211> LENGTH: 17
<212> TYPE: PRT
<213> ORGANISM: Artificial Sequence
<220> FEATURE:
<223> OTHER INFORMATION: H-CDR2

<400> SEQUENCE: 55

Ala Ile Thr Trp Asn Ser Gly His Ile Asp Tyr Ala Asp Ser Val Glu
1               5                   10                  15

Gly

<210> SEQ ID NO 56
<211> LENGTH: 14
<212> TYPE: PRT
<213> ORGANISM: Artificial Sequence
<220> FEATURE:
<223> OTHER INFORMATION: H-CDR3

<400> SEQUENCE: 56

Ala Lys Val Ser Tyr Leu Ser Thr Ala Ser Ser Leu Asp Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: L-CDR1

<400> SEQUENCE: 57

Arg Ala Ser Gln Gly Ile Arg Asn Tyr Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: L-CDR2

<400> SEQUENCE: 58

Ala Ala Ser Thr Leu Gln Ser
1               5

<210> SEQ ID NO 59
<211> LENGTH: 9
<212> TYPE: PRT
<213> ORGANISM: Artificial Sequence
<220> FEATURE:
<223> OTHER INFORMATION: L-CDR3
```

```
<400> SEQUENCE: 59

Gln Arg Tyr Asn Arg Ala Pro Tyr Thr
1               5

<210> SEQ ID NO 60
<211> LENGTH: 8
<212> TYPE: PRT
<213> ORGANISM: Artificial Sequence
<220> FEATURE:
<223> OTHER INFORMATION: H-CDR1

<400> SEQUENCE: 60

Gly Phe Ile Phe Ser Ser Tyr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: H-CDR2

<400> SEQUENCE: 61

Met Ser Tyr Asp Gly Ser Asn Lys
1               5

<210> SEQ ID NO 62
<211> LENGTH: 19
<212> TYPE: PRT
<213> ORGANISM: Artificial Sequence
<220> FEATURE:
<223> OTHER INFORMATION: H-CDR3

<400> SEQUENCE: 62

Ala Arg Asp Arg Gly Ile Ala Ala Gly Gly Asn Tyr Tyr Tyr Tyr Gly
1               5                   10                  15

Met Asp Val

<210> SEQ ID NO 63
<211> LENGTH: 7
<212> TYPE: PRT
<213> ORGANISM: Artificial Sequence
<220> FEATURE:
<223> OTHER INFORMATION: L-CDR1

<400> SEQUENCE: 63

Ser Gln Ser Val Tyr Ser Tyr
1               5

<210> SEQ ID NO 64
<211> LENGTH: 449
<212> TYPE: PRT
<213> ORGANISM: Artificial Sequence
<220> FEATURE:
<223> OTHER INFORMATION: VH

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
```

```
                50             55              60
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                     85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro

<210> SEQ ID NO 65
<211> LENGTH: 10
```

-continued

```
<212> TYPE: PRT
<213> ORGANISM: Artificial Sequence
<220> FEATURE:
<223> OTHER INFORMATION: L-CDR3

<400> SEQUENCE: 65

Gln Gln Arg Ser Asn Trp Pro Pro Phe Thr
1               5                   10

<210> SEQ ID NO 66
<211> LENGTH: 8
<212> TYPE: PRT
<213> ORGANISM: Artificial Sequence
<220> FEATURE:
<223> OTHER INFORMATION: H-CDR1

<400> SEQUENCE: 66

Gly Tyr Val Phe Thr Asp Tyr Gly
1               5

<210> SEQ ID NO 67
<211> LENGTH: 9
<212> TYPE: PRT
<213> ORGANISM: Artificial Sequence
<220> FEATURE:
<223> OTHER INFORMATION: H-CDR2

<400> SEQUENCE: 67

Ile Asn Thr Tyr Ile Gly Glu Pro Ile
1               5

<210> SEQ ID NO 68
<211> LENGTH: 11
<212> TYPE: PRT
<213> ORGANISM: Artificial Sequence
<220> FEATURE:
<223> OTHER INFORMATION: H-CDR3

<400> SEQUENCE: 68

Ala Arg Gly Tyr Arg Ser Tyr Ala Met Asp Tyr
1               5                   10

<210> SEQ ID NO 69
<211> LENGTH: 6
<212> TYPE: PRT
<213> ORGANISM: Artificial Sequence
<220> FEATURE:
<223> OTHER INFORMATION: L-CDR1

<400> SEQUENCE: 69

Gln Asn Val Gly Thr Asn
1               5

<210> SEQ ID NO 70
<211> LENGTH: 214
<212> TYPE: PRT
<213> ORGANISM: Artificial Sequence
<220> FEATURE:
<223> OTHER INFORMATION: VL

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
```

```
                35                  40                  45
Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 71
<211> LENGTH: 9
<212> TYPE: PRT
<213> ORGANISM: Artificial Sequence
<220> FEATURE:
<223> OTHER INFORMATION: L-CDR3

<400> SEQUENCE: 71

```
Gln Gln Tyr Asn Ile Tyr Pro Leu Thr
 1               5
```

<210> SEQ ID NO 72
<211> LENGTH: 8
<212> TYPE: PRT
<213> ORGANISM: Artificial Sequence
<220> FEATURE:
<223> OTHER INFORMATION: H-CDR1

<400> SEQUENCE: 72

```
Gly Phe Ile Phe Ser Asn His Trp
 1               5
```

<210> SEQ ID NO 73
<211> LENGTH: 10
<212> TYPE: PRT
<213> ORGANISM: Artificial Sequence
<220> FEATURE:
<223> OTHER INFORMATION: H-CDR2

<400> SEQUENCE: 73

```
Ile Arg Ser Lys Ser Ile Asn Ser Ala Thr
 1               5                  10
```

<210> SEQ ID NO 74
<211> LENGTH: 11
<212> TYPE: PRT
<213> ORGANISM: Artificial Sequence

```
<220> FEATURE:
<223> OTHER INFORMATION: H-CDR3

<400> SEQUENCE: 74

Ser Arg Asn Tyr Tyr Gly Ser Thr Tyr Asp Tyr
1               5                   10

<210> SEQ ID NO 75
<211> LENGTH: 6
<212> TYPE: PRT
<213> ORGANISM: Artificial Sequence
<220> FEATURE:
<223> OTHER INFORMATION: L-CDR1

<400> SEQUENCE: 75

Gln Phe Val Gly Ser Ser
1               5

<210> SEQ ID NO 76
<211> LENGTH: 712
<212> TYPE: PRT
<213> ORGANISM: Artificial Sequence
<220> FEATURE:
<223> OTHER INFORMATION: SDA-0070

<400> SEQUENCE: 76

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Ala Ile Thr Trp Asn Ser Gly His Ile Asp Tyr Ala Asp Ser Val
            50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Gly Gly Gly Ser Gly Gly Gly Gly Ser Gly Gly Gly Gly Ser
            450                 455                 460

Gln Val Gln Leu Val Glu Ser Gly Gly Val Val Gln Pro Gly Arg
465                 470                 475                 480

Ser Leu Arg Leu Ser Cys Ala Ala Ser Gly Phe Ala Phe Gly Ser Tyr
            485                 490                 495

Thr Met His Trp Val Arg Gln Ala Pro Gly Lys Cys Leu Glu Trp Val
            500                 505                 510

Thr Leu Ile Ser Phe Asp Gly Arg Ser Lys Leu Tyr Gly Asp Ser Val
            515                 520                 525

Lys Gly Arg Phe Thr Ile Ser Arg Asp Asn Ser Lys Asn Ser Leu Tyr
530                 535                 540

Leu Gln Met Asn Ser Leu Arg Ala Glu Asp Thr Ala Val Tyr Tyr Cys
545                 550                 555                 560

Ala Arg Gly Ser Val Arg Gly Glu Ala Ala Phe Asp Leu Trp Gly Gln
            565                 570                 575

Gly Thr Leu Val Thr Val Ser Ser Gly Gly Gly Gly Ser Gly Gly Gly
            580                 585                 590

Gly Ser Gly Gly Gly Gly Ser Gly Gly Gly Gly Ser Ser Tyr Glu Leu
            595                 600                 605

Thr Gln Pro Pro Ser Val Ser Val Ser Pro Gly Gln Thr Ala Ser Ile
            610                 615                 620

Thr Cys Ser Gly Asp Asn Leu Arg Thr Lys Tyr Val Ser Trp Tyr Gln
625                 630                 635                 640

Gln Lys Pro Gly Gln Ser Pro Val Leu Val Ile Tyr Gln Asp Thr Arg
            645                 650                 655

Arg Pro Ser Gly Ile Pro Glu Arg Phe Ser Gly Ser Asn Ser Gly Asn
            660                 665                 670

Thr Ala Thr Leu Thr Ile Ser Gly Thr Gln Ala Met Asp Glu Ala Asp
```

```
                675                 680                 685
Tyr Tyr Cys Met Thr Trp Asp Val Asp Thr Thr Ser Met Ile Phe Gly
        690                 695                 700

Cys Gly Thr Lys Leu Thr Val Leu
705             710

<210> SEQ ID NO 77
<211> LENGTH: 9
<212> TYPE: PRT
<213> ORGANISM: Artificial Sequence
<220> FEATURE:
<223> OTHER INFORMATION: L-CDR3

<400> SEQUENCE: 77

Gln Gln Ser His Ser Trp Pro Phe Thr
1               5

<210> SEQ ID NO 78
<211> LENGTH: 121
<212> TYPE: PRT
<213> ORGANISM: Artificial Sequence
<220> FEATURE:
<223> OTHER INFORMATION: VH

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 79
<211> LENGTH: 107
<212> TYPE: PRT
<213> ORGANISM: Artificial Sequence
<220> FEATURE:
<223> OTHER INFORMATION: VL

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 80
<211> LENGTH: 126
<212> TYPE: PRT
<213> ORGANISM: Artificial Sequence
<220> FEATURE:
<223> OTHER INFORMATION: VH

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
                20                  25                  30

Ala Met His Trp Val Arg Gln Ala Pro Gly Asn Gly Leu Glu Trp Val
            35                  40                  45

Ala Phe Met Ser Tyr Asp Gly Ser Asn Lys Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125

<210> SEQ ID NO 81
<211> LENGTH: 108
<212> TYPE: PRT
<213> ORGANISM: Artificial Sequence
<220> FEATURE:
<223> OTHER INFORMATION: VL

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 82
<211> LENGTH: 117
<212> TYPE: PRT
<213> ORGANISM: Artificial Sequence
<220> FEATURE:
<223> OTHER INFORMATION: VH
```

```
<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser
        115

<210> SEQ ID NO 83
<211> LENGTH: 107
<212> TYPE: PRT
<213> ORGANISM: Artificial Sequence
<220> FEATURE:
<223> OTHER INFORMATION: VL

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 84
<211> LENGTH: 119
<212> TYPE: PRT
<213> ORGANISM: Artificial Sequence
<220> FEATURE:
<223> OTHER INFORMATION: VH

<400> SEQUENCE: 84

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60
```

```
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115

<210> SEQ ID NO 85
<211> LENGTH: 107
<212> TYPE: PRT
<213> ORGANISM: Artificial Sequence
<220> FEATURE:
<223> OTHER INFORMATION: VL

<400> SEQUENCE: 85

Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys
            100                 105

<210> SEQ ID NO 86
<211> LENGTH: 1347
<212> TYPE: DNA
<213> ORGANISM: Artificial Sequence
<220> FEATURE:
<223> OTHER INFORMATION: VH

<400> SEQUENCE: 86
gaagtgcagc tggtggagag cggcggcggc ctggtgcagc ccggcggag  cctgcggctg      60 agctgcgccg ccagcggctt caccttcgac gactacgcca tgcactggt  gcggcaggcc    120 cccggcaagg gcctggagtg ggtgagcgcc atcacctgga  cagcggcca  catcgactac    180 gccgacagcg tggagggccg gttcaccatc agcgggaca  acgccaagaa cagcctgtac    240
ctgcagatga acagcctgcg ggccgaggac accgccgtgt actactgcgc caaggtgagc    300
tacctgagca ccgccagcag cctggactac tggggccagg gcaccctggt caccgtctct    360
agcgctagca ccaagggccc atcggtcttc cccctggcac cctcctccaa gagcacctct    420
gggggcacag cggccctggg ctgcctggtc aaggactact cccccgaacc ggtgacggtg    480
tcgtggaact caggcgccct gaccagcggc gtgcacacct tccggctgt  cctacagtcc    540 tcaggactct actccctcag cagcgtggtg accgtgccct ccagcagcct gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat  ctcccggacc    780
```

```
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca gaaccaggt cagcctgacc tgcctggtca aaggcttcta tcccagcgac    1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccg                                       1347

<210> SEQ ID NO 87
<211> LENGTH: 744
<212> TYPE: DNA
<213> ORGANISM: Artificial Sequence
<220> FEATURE:
<223> OTHER INFORMATION: scFv

<400> SEQUENCE: 87
caggtgcagc tggtggagtc tgggggaggc gtggtgcagc ctggagggtc cctcagactc     60
tcctgtgcag cctctggatt cgccttcggt agttacacta tgcactgggt ccgccaggcg    120
ccaggcaagt gcctggagtg ggtgacactt atatcgtttg atggacgtag caagctttac    180
ggagactccg tgaagggccg attcaccatc tccagagaca attccaagaa cagcctgtat    240
ctgcagatga acagcctgcg agccgaggac acggccgtgt attactgtgc gagagggtct    300
gtgcggggtg aagctgcttt cgatctctgg ggccaaggga cactggtcac cgtctcctca    360
ggcggcggtg gatccggcgg aggaggctcc ggaggtggcg gaagcggtgg cggaggatct    420
tcctatgagc tgacacagcc cccctcagtg tccgtgtcgc aggacagaca agccagcatc    480
acctgctctg gagataactt gcgtactaaa tatgtttctt ggtatcagca gaagccaggc    540
cagtcccctg tgttggtcat ctatcaggac accaggcggc cctcaggcat ccctgagcga    600
ttctcaggct ccaactcggg gaacacagcc actctgacca tcagcgggac ccaggctatg    660
gatgaagctg actattactg tatgacgtgg gacgttgaca ctacctcgat gattttcggc    720
tgcgggacca agctgaccgt ccta                                           744

<210> SEQ ID NO 88
<211> LENGTH: 45
<212> TYPE: DNA
<213> ORGANISM: Artificial Sequence
<220> FEATURE:
<223> OTHER INFORMATION: linker

<400> SEQUENCE: 88
ggaggcggag gttctggcgg cggcggctcc ggtggaggtg gctca                     45

<210> SEQ ID NO 89
<211> LENGTH: 642
<212> TYPE: DNA
<213> ORGANISM: Artificial Sequence
<220> FEATURE:
<223> OTHER INFORMATION: VL

<400> SEQUENCE: 89
```

```
gacatccaga tgacccagtc tcccagcagc ctgagcgcca gcgtgggcga ccgggtgacc      60
atcacctgcc gggccagcca gggcatccgg aactacctgg cctggtacca gcagaagccc     120
ggcaaggccc ccaagctgct gatctacgcc gccagcaccc tgcagagcgg cgtgcccagc     180
cggttcagcg gcagcggcag cggcaccgac ttcaccctga ccatcagcag cctgcagccc     240
gaggacgtgg ccacctacta ctgccagcgg tacaaccggg ccccctacac cttcggccag     300
ggcaccaagg tggaaatcaa agaaccgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg     540 ctgagcaaag cagactacga gaaacacaaa gtctacgcct gcgaagtcac ccatcagggc     600
ctgagctcgc ccgtcacaaa gagcttcaac aggggagagt gt                       642
```

BISPECIFIC ANTIBODY SPECIFICALLY BINDING TO IL-17A AND TNF-α

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/005213, filed Apr. 20, 2020 which claims priority to the benefit of Korean Patent Application No. 10-2019-0049177 filed in the Korean Intellectual Property Office on Apr. 26, 2019, the entire contents of which are incorporated herein by reference.

BACKGROUND

1. Technical Field

The present invention relates to a bispecific antibody specifically binding to IL-17A and TNF-α and use thereof.

2. Background Art

TNF-α (tumor necrosis factor-alpha) is an inflammatory cytokine produced by immune cells like activated macrophages, CD4+ T cells, and NK cells, and it plays a role of controlling immune responses based on immune cell regulation. For some tumor cells, TNF-α induces hemorrhagic necrosis and cell apoptosis, and, by promoting proliferation and differentiation of T cells and proliferation of B cells, it activates immune responses (*Biotherapy.* 3(2): 103-11, 1991). Although TNF-α is a cytokine that is important for having normal immune responses, when an imbalance like overexpression of TNF-α occurs in a living body, various autoimmune responses are caused. In addition, as a pro-inflammatory cytokine, TNF-α causes an enhancement of other cytokines in an area showing autoimmune responses to accelerate the symptoms (*Annu Rev Immunol.* 14: 97-440, 1996; *Inflamm Bowel Dis.* 5(2): 19-33, 1999).

To have a treatment and alleviation of the autoimmune diseases, various TNF-α inhibitors have been developed, and representative examples of the inhibitors include infliximab (brand name: Remicade), adalimumab (brand name: Humira), etanercept (brand name: Enbrel), and the like. However, for 10 to 30% of the patients suffering from autoimmune disease, TNF-α inhibitor shows no treatment effect, and also a gradual decrease in the treatment effect is shown in about 60% of the patients, and thus it is required to have higher dose or other alternative therapies (*Rheumatology* (Oxford). 46(7): 1153-6, 2007; *Ann Rheum Dis.* 65(6): 746-52, 2006).

IL-17 (interleukin-17A) as a representative inflammatory cytokine is produced by Th cell group known as T helper 17 cells (*J Exp Med.* 1; 183(6): 2593-603, 1996). IL-17 consists of total 6 families, i.e., IL-17A, IL-17B, IL-17C, IL-17D, IL-17E, and IL-17F, and, in particular, IL-17F shows the highest homology with IL-17A. IL-17A and IL-17F separately form a homo dimer or a hetero dimer in which they are linked to each other. IL-17 in dimer form binds to IL-17R, i.e., a receptor. IL-17R has 5 subtypes of IL-17RA, IL-17RB, IL-17RC, IL-17RD, and IL-17RE. Once IL-17 binds to IL-17R as a receptor, the signal transduction system for inducing chemokines is activated and immune cells like monocytes and neutrophils are induced to an inflammation site by the chemokines. IL-17 works with TNF-α, IL-1, or the like, and their signal transduction system is identified in onset mechanisms of various autoimmune diseases (*J Invest Dermatol.* 131(3): 677-87, 2011; *N Engl J Med.* 27; 361(9): 888-98, 2009; *J Invest Dermatol.* 133(1): 17-26, 2013).

For the treatment and alleviation of IL-17 mediated autoimmune diseases, IL-17 inhibitors have been developed and approved as a pharmaceutical product. In January 2015, secukinumab (brand name: Cosentyx), which is a monoclonal antibody inhibiting IL-17, was approved by FDA as a therapeutic agent for severe plaque psoriasis.

Interestingly, secukinumab was tested for a patient having ankylosing spondylitis as a subject who does not respond to TNF-α inhibitor during phase 3 clinical trial, and the ASAS20 response rate was between 45.5% and 58.8% depending on administration mode. Compared to the result that the ASAS20 response rate is, depending on administration mode, 60%, 66.3% in a patient who has not previously administered with TNF-α inhibitor, secukinumab was shown to be effective for a patient having ankylosing spondylitis regardless of the previous exposure to TNF-α inhibitor (2014 ACR/ARHP annual meeting, ABSTRACT NUMBER: 819). However, as the ASAS20 non-response rate and ASAS40 non-response rate still remain at 40% and 60%, respectively, there is a need for having an agent with improved therapeutic effect for the disease.

For those reasons, considering the excellent efficacy of TNF-α inhibitor and IL-17 inhibitor for ankylosing spondylitis, axial spondyloarthritis, or the like, combination therapy for having enhanced efficacy while dealing with the problem of side effects receives increasing attention (*Rheumatology* (Oxford). 55 (suppl 2): ii38-ii42, 2016). Moreover, for a patient which shows an undesirable response to a monospecific antibody relating to previous anti TNF-α therapy or anti IL-17 therapy, a need for switching to a bispecific pharmaceutical has been reported (*Rheumatology* (Oxford). 2017 Oct. 12).

It is expected based on those results that, rather than the inhibition of a single cytokine, quick inhibition of inflammation and immune response by simultaneously inhibiting TNF-α and IL-17 at the level at which the normal immune system is not greatly affected is more effective and enduring therapy. Moreover, such therapy is expected to show the effect even when applied to a patient showing no response to a TNF-α inhibitor and also a patient who has developed resistance to TNF-α. In this regard, combination therapy in which each of an immunosuppressant for TNF-α and an immunosuppressant for IL-17 is administered may be considered. However, considering the inconvenience caused by increased administration number and increased dose and also the higher cost caused by producing separately each pharmaceutical, it is efficient to use a bispecific antibody for which minimum administration and cost reduction are anticipated.

Accordingly, inventors of the present invention carried out intensive studies to develop a bispecific antibody specifically binding to IL-17A and TNF-α, and, as a result, produced a bispecific antibody which specifically inhibits IL-17A and TNF-α at the same time and has excellent efficacy. By also finding that the antibody has a lower chance of having side effect while exhibiting the desired therapeutic effect, the inventors completed the present invention.

The information described in Background Art above is given only for helping the understanding of background of the present invention, and information forming prior art that is already well known to a person with common knowledge in the technical field to which the present invention pertains may not be included.

SUMMARY

Object of the present invention is to provide a bispecific antibody specifically binding to IL-17A and TNF-α comprising an antibody specifically binding to IL-17A or an antigen binding fragment thereof and an antibody specifically binding to TNF-α or an antigen binding fragment thereof.

Another object of the present invention is to provide a polynucleotide encoding the bispecific antibody or an antigen binding fragment thereof.

Another object of the present invention is to provide a vector including the polynucleotide, a cell transformed with the vector, and a method of producing the bispecific antibody or an antigen binding fragment thereof.

Another object of the present invention is to provide a pharmaceutical composition for preventing or treating an autoimmune disease comprising the bispecific antibody or an antigen binding fragment thereof.

Still another object of the present invention is to provide an antibody-drug conjugate containing the bispecific antibody or an antigen binding fragment thereof.

To achieve the object described above, the present invention provides a bispecific antibody specifically binding to IL-17A and TNF-α comprising an antibody specifically binding to IL-17A or an antigen binding fragment thereof and an antibody specifically binding to TNF-α or an antigen binding fragment thereof, characterized in that the antibody specifically binding to IL-17A or an antigen binding fragment thereof includes (i) heavy chain CDR1 of SEQ ID NO: 1 or SEQ ID NO: 8; heavy chain CDR2 selected from the group consisting of SEQ ID NO: 2, SEQ ID NO: 4, SEQ ID NO: 9 and SEQ ID NO: 11, and heavy chain CDR3 selected from the group consisting of SEQ ID NO: 3, SEQ ID NO: 5, SEQ ID NO: 6, SEQ ID NO: 7 and SEQ ID NO: 10, and (ii) light chain CDR1 of SEQ ID NO: 12; light chain CDR2 of SEQ ID NO: 13; and light chain CDR3 of SEQ ID NO: 14.

The present invention further provides a polynucleotide encoding the bispecific antibody or an antigen binding fragment thereof.

The present invention further provides a vector including the polynucleotide.

The present invention further provides a cell transformed with the vector.

The present invention further provides a method of producing the bispecific antibody or an antigen binding fragment thereof including steps of: (a) culturing the aforementioned cell; and (b) collecting a bispecific antibody specifically binding to IL-17A and TNF-α or an antigen binding fragment thereof from the cultured cell.

The present invention further provides a pharmaceutical composition for preventing or treating an autoimmune disease comprising the bispecific antibody or an antigen binding fragment thereof, or a method of preventing or treating an autoimmune disease including administering the bispecific antibody or an antigen binding fragment thereof to an individual.

The present invention still further provides an antibody-drug conjugate containing the bispecific antibody or an antigen binding fragment thereof, and a drug conjugated thereto.

DETAILED DESCRIPTION

Figure 1:
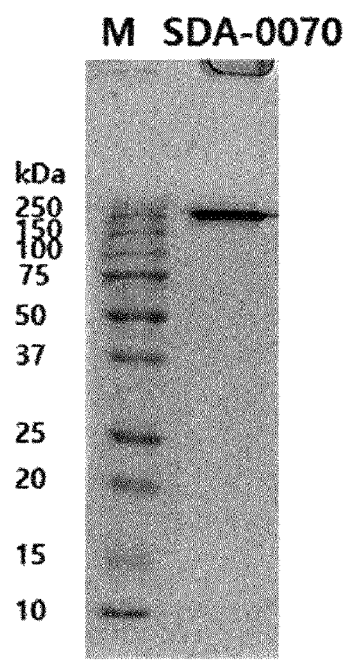
FIG. 1 shows the result of SDS-PAGE analysis of SDA-0070, which is a bispecific antibody candidate, after purifying SDA-0070 by GFC (gel filtration chromatography) and FPLC (fast protein liquid chromatography).

Unless defined otherwise, all the technical and scientific terms described in the present specification have the same meaning as those generally understood by a person who is skilled in the technical field to which the present invention pertains. In general, the nomenclature employed in the present specification is the same as those well-known and commonly used in the corresponding technical field.

The bispecific antibody of the present invention has an effect of suppressing an autoimmune disease by more efficiently inhibiting TNF-α and IL-17A, which are inflammatory cytokines, and it also has a binding property for each target of TNF-α and IL-17A. In particular, without having any binding to a non-specific antigen protein, the bispecific antibody of the present invention shows excellent specificity of specifically binding to human TNF-α and human IL-17A or IL-17A/F only, and, compared to the monospecific antibody against TNF-α (Humira), monospecific antibody against IL-17A (secukinumab), or conventional bispecific antibody against TNF-α and IL-17A (LY3114062), it shows more excellent efficacy.

Thus, in one aspect, the present invention relates to a bispecific antibody specifically binding to IL-17A and TNF-α comprising an antibody specifically binding to IL-17A or an antigen binding fragment thereof and an antibody specifically binding to TNF-α or an antigen binding fragment thereof, characterized in that the antibody specifically binding to IL-17A or an antigen binding fragment thereof includes heavy chain CDR1 of SEQ ID NO: 1 or SEQ ID NO: 8; heavy chain CDR2 selected from the group consisting of SEQ ID NO: 2, SEQ ID NO: 4, SEQ ID NO: 9 and SEQ ID NO: 11; and heavy chain CDR3 selected from the group consisting of SEQ ID NO: 3, SEQ ID NO: 5, SEQ ID NO: 6, SEQ ID NO: 7 and SEQ ID NO: 10, and (ii) light chain CDR1 of SEQ ID NO: 12; light chain CDR2 of SEQ ID NO: 13; and light chain CDR3 of SEQ ID NO: 14.

As described herein, the term "bispecific antibody" means an antibody having a binding property or an antagonistic property for one or more targets, and it indicates antibody form in which antibodies having a binding property or an antagonistic property for 2 or more different targets are bound to each other, or an antibody in which an antibody having a binding property for one target and a material having an antagonistic property for other target are bound to each other.

The "IL-17A" protein as one target of the bispecific antibody of the present invention may be those derived from any species. For example, it may be a protein derived from primates like human and monkey or rodents like mouse and rat, or the like. IL-17 is related with the abnormal expression of immune system involved in autoimmune diseases such as rheumatoid arthritis (RA), psoriasis (PsA), lupus erythematosus, Crohn's disease, multiple sclerosis, systemic sclerosis, Behcet's disease, or the like.

As described herein, the term "antibody" encompasses both the polyclonal antibody and monoclonal antibody, and it also encompasses not only an antibody in complete form having two full-chain light chains and two full-chain heavy chains but also a fragment of the antibody molecule.

An antibody in complete form has a structure with two full-chain light chains and two full-chain heavy chains, in which each light chain is linked to heavy chain via a disulfide bond. Constant region of a heavy chain has gamma (γ), mu (μ), alpha (α), delta (δ) and epsilon (ε) types, and, as a subclass, it has gamma1 (γ1), gamma2 (γ2), gamma3 (γ3), gamma4 (γ4), alpha1 (α1) and alpha2 (α2). Constant region of a light chain has kappa (κ) and lambda (2) types. A basic 4-chain antibody unit is a hetero tetramer glycoprotein consisting of 2 identical light chains (L) and 2 identical heavy chains (H). Light chain has a variable region (VL) at the N-terminus and a constant region at the other terminus. Heavy chain has a variable region (VH) at the N-terminus and 3 constant regions (CH) for α and γ chains, respectively, and 4 CH regions for μ and ε isotypes. The term "variable" means the sequence at specific part of a variable region is significantly different among the antibodies. By the variable region, antigen binding is mediated and specificity of a specific antibody against a specific antigen is determined. In variable region of both the light chain and heavy chain, the variation property is concentrated at hypervariable region (HVR) i.e., 3 segments referred to as CDR (complementarity determining region). More highly conserved part in variable region is referred to as framework region (FR). Heavy chain and light chain variable regions have a structure in which FR1, CDR1, FR2, CDR2, FR3, CDR3 and FR4 are present from N-terminus to C-terminus.

As described herein, the term "heavy chain" means a full-length heavy chain and a fragment thereof which has a variable region domain VH including an amino acid sequence with variable region sequence that is sufficient for providing an antigen with specificity, and 3 constant region domains of CH1, CH2 and CH3.

Moreover, as described herein, the term "light chain" means a full-length light chain and a fragment thereof which has a variable region domain VL including an amino acid sequence with variable region sequence that is sufficient for providing an antigen with specificity, and constant region domain CL.

The antigen binding fragment of an antibody or antibody fragment means a fragment which has a property of binding to an antigen, and it encompasses Fab, F(ab')2, Fv, and the like.

"Fv" fragment is an antibody fragment which has a full antibody recognizing and binding site. This region is composed of a dimer in which one heavy chain variable domain and one light chain variable domain are tightly associated with each other, i.e., actually covalently linked as scFv, for example.

"Fab" fragment contains variable and constant domains of a light chain and variable domain and the first constant domain (CH1) of a heavy chain. F(ab')$_2$ antibody fragment generally includes a pair of Fab fragments which are covalently linked, via hinge cysteine, near their carboxy terminals.

"Single chain Fv" or "scFv" antibody fragment includes VH and VL domains of an antibody, and those domains are present within a single polypeptide chain. Fv polypeptide may further contain a polypeptide linker between the VH domain and VL domain so that scFv forms a structure suitable for binding to an antigen.

In one example, the antibody according to the present invention is in Fv form (e.g., scFv) or full antibody form. Moreover, the heavy chain constant region may be any isotype selected from gamma (γ), mu (μ), alpha (α), delta (δ), and epsilon (ε). For example, the constant region is gamma 1 (IgG1), gamma 3 (IgG3) or gamma 4 (IgG4). The light chain constant region may be kappa or lambda type.

The antibody of the present invention encompasses a monoclonal antibody, a multi-specific antibody, a human antibody, a humanized antibody, a chimera antibody, a single chain Fvs (scFV), a single chain antibody, a Fab fragment, a F(ab') fragment, a disulfide-bridge Fvs (sdFV), an anti-idiotype (anti-Id) antibody, and an epitope-binding fragment of those antibodies, but it is not limited thereto.

The monoclonal antibody indicates an antibody obtained from a substantially homologous antibody group, i.e., antibodies constituting the group are identical to each other except naturally occurring mutants which may be present in trace amount. As the monoclonal antibody is highly specific, it is derived against a single antigen site.

Non-human (e.g., murine) antibody in the aforementioned "humanized" form is a chimera antibody which contains a minimum sequence derived from non-human immunoglobulin. In most cases, the humanized antibody is human immunoglobulin (i.e., recipient antibody) in which residues of the hypervariable region of a recipient is substituted with residues of the hypervariable region of non-human species like mouse, rat, rabbit, or non-human primates having desired specificity, affinity, and properties (i.e., donor antibody).

The "human antibody" means that, as a molecule derived from human immunoglobulin, entire amino acid sequence constituting the antibody including complementarity determining region and structure region are composed of human immunoglobulin. Human antibody can be produced by using various techniques, including phage display library, that are well known in the pertinent art. Although a human antibody is modified to produce an antibody in response to the test injection of an antigen, it can be also produced by administering an antigen to a transgenic animal without functioning endogenous locus, i.e., immunologically treated xenomouse. While ixekizumab is a humanized antibody which has been conventionally used, the antibody according to the present invention is a human antibody.

Also encompassed by the present invention is a fragment of the aforementioned antibody showing the desired biological activity as well as a "chimera" antibody (immunoglobulin) in which part of the heavy chain and/or light chain is derived from a certain species or the same as or homologous to a corresponding sequence within the antibody belonging to a specific antibody class or subclass while other chain(s) is/are derived from other species or the same as or homologous to a corresponding sequence within the antibody belonging to other antibody class or subclass.

As described herein, the expression "antibody variable domain" indicates light chain and heavy chain parts of an antibody molecule including the amino acid sequences of complementarity determining region (CDR) and framework region (FR). VH indicates the variable domain of a heavy chain. VL indicates the variable domain of a light chain.

"Complementarity determining region (CDR)" indicates the amino acid residue of an antibody variable domain, which is required for binding to an antigen. Each variable domain typically has 3 CDR regions that are identified as CDR1, CDR2 and CDR3.

In one example, with regard to the bispecific antibody or an antigen binding fragment thereof according to the present invention, the antibody specifically binding to IL-17A or an antigen binding fragment thereof may include heavy chain CDR1 of SEQ ID NO: 1, heavy chain CDR2 of SEQ ID NO: 2, heavy chain CDR3 of SEQ ID NO: 3; heavy chain CDR1 of SEQ ID NO: 1, heavy chain CDR2 of SEQ ID NO: 4, heavy chain CDR3 of SEQ ID NO: 5; heavy chain CDR1 of SEQ ID NO: 1, heavy chain CDR2 of SEQ ID NO: 4, heavy chain CDR3 of SEQ ID NO: 6; heavy chain CDR1 of SEQ ID NO: 1, heavy chain CDR2 of SEQ ID NO: 4, heavy chain CDR3 of SEQ ID NO: 7; heavy chain CDR1 of SEQ ID NO: 8, heavy chain CDR2 of SEQ ID NO: 9, heavy chain CDR3 of SEQ ID NO: 10; or heavy chain CDR1 of SEQ ID NO: 8, heavy chain CDR2 of SEQ ID NO: 11, heavy chain CDR3 of SEQ ID NO: 10.

"Framework region (FR)" means a residue of variable domain other than CDR residue. Each variable domain typically has 4 FRs that are identified as FR1, FR2, FR3 and FR4.

In one example, with regard to the bispecific antibody or an antigen binding fragment thereof according to the present invention, the antibody specifically binding to IL-17A or an antigen binding fragment thereof may include a heavy chain variable region FR selected from the group consisting of SEQ ID NO: 15 to SEQ ID NO: 26. Specifically, it may include a heavy chain variable region FR selected from the group consisting of FR1 of SEQ ID NO: 15, FR2 of SEQ ID NO: 16, FR3 of SEQ ID NO: 17 and FR4 of SEQ ID NO: 18; FR1 of SEQ ID NO: 19, FR2 of SEQ ID NO: 16, FR3 of SEQ ID NO: 20 and FR4 of SEQ ID NO: 21; FR1 of SEQ ID NO: 22, FR2 of SEQ ID NO: 23, FR3 of SEQ ID NO: 24 and FR4 of SEQ ID NO: 25; and FR1 of SEQ ID NO: 22, FR2 of SEQ ID NO: 26, FR3 of SEQ ID NO: 24 and FR4 of SEQ ID NO: 25.

In one example, with regard to the bispecific antibody or an antigen binding fragment thereof according to the present invention, the antibody specifically binding to IL-17A or an antigen binding fragment thereof may include a light chain variable region FR selected from the group consisting of SEQ ID NO: 27 to SEQ ID NO: 33. Specifically, it may include a light chain variable region FR selected from the group consisting of FR1 of SEQ ID NO: 27, FR2 of SEQ ID NO: 28, FR3 of SEQ ID NO: 29 and FR4 of SEQ ID NO: 30; or FR1 of SEQ ID NO: 31, FR2 of SEQ ID NO: 32, FR3 of SEQ ID NO: 33 and FR4 of SEQ ID NO: 30.

Including the aforementioned CDR1 to CDR3 and FR, with regard to the bispecific antibody or an antigen binding fragment thereof according to the present invention, the antibody specifically binding to IL-17A or an antigen binding fragment thereof may include a heavy chain variable region selected from the group consisting of SEQ ID NO: 34 to SEQ ID NO: 39. Moreover, the antibody or an antigen binding fragment thereof according to the present invention may include a light chain variable region selected from SEQ ID NO: 40 or SEQ ID NO: 41.

In one example, with regard to the bispecific antibody or an antigen binding fragment thereof according to the present invention, the antibody specifically binding to IL-17A or an antigen binding fragment thereof may include a heavy chain variable region and a light chain variable region that are shown below:
  (i) heavy chain variable region of SEQ ID NO: 34 and light chain variable region of SEQ ID NO: 40;
  (ii) heavy chain variable region of SEQ ID NO: 35 and light chain variable region of SEQ ID NO: 41;
  (iii) heavy chain variable region of SEQ ID NO: 36 and light chain variable region of SEQ ID NO: 41;
  (iv) heavy chain variable region of SEQ ID NO: 37 and light chain variable region of SEQ ID NO: 41;
  (v) heavy chain variable region of SEQ ID NO: 38 and light chain variable region of SEQ ID NO: 40; or
  (vi) heavy chain variable region of SEQ ID NO: 39 and light chain variable region of SEQ ID NO: 41.

"TNF-α" as one target of the bispecific antibody of the present invention is an inflammatory cytokine produced by activated macrophages and immune cells such as CD4+ T cells or NK cells, and it plays a role of regulating an inflammation response by controlling immune cells. TNF-α protein may be those derived from any species. For example, it may be a protein derived from primates like human and monkey or rodents like mouse and rat, or the like. Activation of the immune system caused by TNF-α mediates an autoimmune disease such as rheumatoid arthritis (RA), ankylosing spondylitis, or inflammatory bowel disease, psoriasis.

With regard to the bispecific antibody according to the present invention, the antibody specifically binding to TNF-α or an antigen binding fragment thereof can be used without any limitation as long as it is an antibody having a property of binding to TNF-α and inhibiting the TNF-α activity It is preferably selected from the group consisting of adalimumab (brand name: Humira), golimumab (brand name: Simponi), certolizumab (brand name: Cimzia), and infliximab (brand name: Remicade), or a variant thereof, but it is not limited thereto.

With regard to the bispecific antibody according to the present invention, the antibody specifically binding to TNF-α or an antigen binding fragment thereof preferably includes (i) heavy chain CDR1 of SEQ ID NO: 54, heavy chain CDR2 of SEQ ID NO: 55, and heavy chain CDR3 of SEQ ID NO: 56; and light chain CDR1 of SEQ ID NO: 57, light chain CDR2 of SEQ ID NO: 58, and light chain CDR3 of SEQ ID NO: 59; (ii) heavy chain CDR1 of SEQ ID NO: 60, heavy chain CDR2 of SEQ ID NO: 61, and heavy chain CDR3 of SEQ ID NO: 62; and light chain CDR1 of SEQ ID NO: 63, light chain CDR2 of Asp Ala Ser, and light chain CDR3 of SEQ ID NO: 65; (iii) heavy chain CDR1 of SEQ ID NO: 66, heavy chain CDR2 of SEQ ID NO: 67, and heavy chain CDR3 of SEQ ID NO: 68; and light chain CDR1 of SEQ ID NO: 69, light chain CDR2 of Ser Ala Ser, and light chain CDR3 of SEQ ID NO: 71; or (iv) heavy chain CDR1 of SEQ ID NO: 72, heavy chain CDR2 of SEQ ID NO: 73, and heavy chain CDR3 of SEQ ID NO: 74; and light chain CDR1 of SEQ ID NO: 75, light chain CDR2 of Tyr Ala Ser, and light chain CDR3 of SEQ ID NO: 77. More preferably, it includes (i) heavy chain variable region of SEQ ID NO: 78 and light chain variable region of SEQ ID NO: 79; (ii) heavy chain variable region of SEQ ID NO: 80 and light chain variable region of SEQ ID NO: 81; (iii) heavy chain variable region of SEQ ID NO: 82 and light chain variable region of SEQ ID NO: 83; or (iv) heavy chain variable region of SEQ ID NO: 84 and light chain variable region of SEQ ID NO: 85, but it is not limited thereto.

Sequence of the antibody specific to TNF-α is the same as those described in the following Table 1 (heavy chain CDR and heavy chain variable region) and Table 2 (light chain CDR and light chain variable region).

TABLE 1

| TNF-α Antibody | H-CDR1 | H-CDR2 | H-CDR3 |
|---|---|---|---|
| Adalimumab | DYAMH (SEQ ID NO: 54) VH | AITWNSGHIDYADSVEG (SEQ ID NO: 55) | AKVSYL STA S SLDY (SEQ ID NO: 56) |
| | EVQLVESGGGLVQPGRSLRLSCAASGFTFDDYAMHWVRQAPGKGLEWVSAITWNSGHIDYADSVEGRFTISRDNAKNSLYLQMNSLRAEDTAVYYCAKVSYLSTASSLDYWGQGTLVTVSS (SEQ ID NO: 78) | | |
| Golimumab | GFIFSSYA (SEQ ID NO: 60) VH | MSYDGSNK (SEQ ID NO: 61) | ARDRGIAAGGNYYYYGMDV (SEQ ID NO: 62) |
| | QVQLVESGGGVVQPGRSLRLSCAASGFIFSSYAMHVVRQAPGNGLEWVAFMSYDGSNKKYADSVKGRFTISRDNSKNTLYLQMNSLRAEDTAVYYCARDRGIAAGGNYYYYGMDVVVGQGTTVTVSS (SEQ ID NO: 80) | | |
| Certolizumab pegol | GYVFTDYG (SEQ ID NO: 66) VH | INTYIGEPI (SEQ ID NO: 67) | ARGYRSYAMDY (SEQ ID NO: 68) |
| | EVQLVESGGGLVQPGGSLRLSCAASGYVFTDYGMNWVRQAPGKGLEWMGWINTYIGEPIYADSVKGRFTFSLDTSKSTAYLQMNSLRAEDTAVYYCARGYRSYAMDYWGQGTLVTVS (SEQ ID NO: 82) | | |
| Infliximab | GF1FSNHW (SEQ ID NO: 72) VH | IRSKSINSAT (SEQ ID NO: 73) | SRNYYGSTYDY (SEQ ID NO: 74) |
| | EVKLEESGGGLVQPGGSMKLSCVASGFIFSNHWMNWVRQSPEKGLEWVAEIRSKSINSATHYAESVKGRFTISRDDSKSAVYLQMTDLRTEDTGVYYCSRNYYGSTYDYWGQGTTLTVS (SEQ ID NO: 84) | | |

TABLE 2

| TNF-α Antibody | L-CDR1 | L-CDR2 | L-CDR3 |
|---|---|---|---|
| Adalimumab | RASQGIRNYLA (SEQ ID NO: 57) VL | AASTLQS (SEQ ID NO: 58) | QRYNRAPYT (SEQ ID NO: 59) |
| | DIQMTQSPSSLSASVGDRVTITCRASQGIRNYLAWYQQKPGKAPKLLIYAASTLQSGVPSRFSGSGSGTDFTLTISSLQPEDVATYYCQRYNRAPYTFGQGTKVEIK (SEQ ID NO: 79) | | |
| Golimumab | SQSVYSY (SEQ ID NO: 63) VL | DAS (SEQ ID NO: 65) | QQRSNVVPPFT |
| | EIVLTQSPATLSLSPGERATLSCRASQSVYSYLAWYQQKPGQAPRLLIYDASNRATGIPARFSGSGSGTDFTLTISSLEPEDFAVYYCQQRSNWPPFTFGPGTKVDIK (SEQ ID NO: 81) | | |
| Certolizumab pegol | QNVGTN (SEQ ID NO: 69) VL | SAS | QQYNIYPLT (SEQ ID NO: 71) |
| | DIQMTQSPSSLSASVGDRVTITCKASQNVGTNVAWYQQKPGKAPKALIYSASFLYSGVPYRFSGSGSGTDFTLTISSLQPEDFATYYCQQYNIYPLTFGQGTKVEIK (SEQ ID NO: 83) | | |
| Infliximab | QFVGSS (SEQ ID NO: 75) VL | YAS | QQSHSWPFT (SEQ ID NO: 77) |
| | DILLTQSPAILSVSPGERVSFSCRASQFVGSSIHWYQQRTNGSPRLLIKYASESMSGIPSRFSGSGSGTDFTLSINTVESEDIADYYCQQSHSWPFTFGSGTNLEVK (SEQ ID NO: 85) | | |

In one embodiment of the present invention, a linker was introduced to the 3'-terminus of nucleic acid sequence (SEQ ID NO: 86) of the heavy chain of an anti TNF-α antibody, a scFv nucleic acid sequence (SEQ ID NO: 87) using anti IL-17A VH and VL, which have been obtained by optimization after the introduction, was linked thereto, and a bispecific antibody which simultaneously inhibits the activity of both TNF-α and IL-17A was expressed in HEK293F cells by using it.

The bispecific antibody is an antibody which can bind to two different types of antigens (target proteins), and it may be in antibody form which has been prepared by genetic engineering or any other method. The bispecific antibody according to the present invention may be in antibody form in which plural antibodies are linked to one another via a linker.

The linker means a linking body which can connect two different types of fusion partners (e.g., biological polymer) by utilizing hydrogen bond, electrostatic interaction, van der Waals force, disulfide bond, salt bridge, hydrophobic interaction, covalent bond, or the like. Specifically, the linker may have at least one cysteine capable of participating in forming one or more disulfide bonds at physiological conditions or other standard peptide conditions (e.g., conditions for peptide purification, conditions for peptide storage, or the like), and, other than the role of simply linking each fusion partner, it may play a role of a hinge which provides a gap with certain volume between fusion partners or provides flexibility or rigidity to a fusion body. The linker may be either a non-peptide linker or a peptide linker, and those directly linked by a peptide bond, disulfide bond, or the like may be also included herein.

The peptide linker may have an amino acid sequence in which plural amino acid sequences or motifs are repeated.

The non-peptide linker may be a biodegradable polymer such as polyethylene glycol (PEG) homopolymer, polypropylene glycol homopolymer, ethylene glycol-propylene glycol copolymer, polyoxyethylated polyol, polyvinyl alcohol, polysaccharide, dextran, or polyvinyl ether, a lipid polymer, chitins, hyaluronic acid, or a combination thereof. Specifically, it may be a polyethylene glycol homopolymer, and derivatives thereof that are already known in the pertinent art and derivatives that can be easily produced at a technical level of the pertinent art may be also within the scope of the present invention.

A site directly or indirectly linked via the linker is not particularly limited, but it may be Fc part, Fab', F(ab')$_2$, Fab, Fv, or the like.

In the present invention, the bispecific antibody contains the heavy chain and light chain of an antibody specifically binding to IL-17A; and the heavy chain and light chain of an antibody specifically binding to TNF-α, and it is preferable that the C-terminus of the heavy chain constant region of an antibody specifically binding to IL-17A is linked to the C-terminus of the heavy chain constant region of an antibody specifically binding to TNF-α, and it is also preferable that the antigen binding fragment of the antibody specifically binding to IL-17A is linked to the C-terminus of the heavy chain constant region of an antibody specifically binding to TNF-α, but it is not limited thereto.

With regard to the bispecific antibody of the present invention, the linkage between antibody and antibody or linkage between antibody and fragment may be achieved by various methods like binding via linker, direct chemical binding, and genetic fusion. Preferably, it is a binding via the linker (SEQ ID NO: 88), but it is not limited thereto.

Moreover, the antibody fragment is characterized in that it is a single-chain variable fragment (scFv).

In a specific example of the present invention, inventors of the present invention produced IL-17A antigen protein by cloning IL-17A gene. Moreover, according to a reaction of the antigen protein with a library phage, scFv-phage specifically binding to IL-17A was obtained, and a panning process for amplification based on bacterial infection was repeated 3 times.

Moreover, from a polyclonal phage antibody group with high binding property obtained after the $3^{rd}$ panning, a monoclonal antibody was selected. By carrying out an ELISA analysis therefor, a monoclonal antibody was selected once more. Based on sequence analysis of the monoclonal phages which have been selected as described, the pattern and polypeptide sequence of CDR region in VH and VL of 6 monoclonal antibodies were determined (Table 4 and Table 5).

Among the 6 types of monoclonal phages which have been selected as above, scFv of 7H3C11FW was cloned into the 3'-terminus of heavy chain nucleic acid sequence of Humira, which is an anti-TNF-α monospecific antibody, to produce SDA-0070 that is bispecific to IL-17A and TNF-α. It was found by ELISA analysis that the thus-produced bispecific antibody has binding specificity, i.e., binding only to TNF-α and human IL-17A or IL-17A/F, and has a significantly higher specific binding property and neutralization property compared to an IL-17A monospecific antibody or a TNF-α monospecific antibody and also a conventional TNF-α and IL-17A bispecific antibody (LY3114062).

Accordingly, it was found that the bispecific antibody specifically binding to IL-17A and TNF-α of the present invention has a property of strongly binding to IL-17A and TNF-α at the same time.

With regard to the antibody or antibody fragment of the present invention, an antibody having a mutation occurred in variable region or an antibody fragment thereof is also within the scope of the present invention, as long as the characteristics of antibody or antibody fragment are maintained. Examples thereof include an antibody having a conservative substitution of an amino acid occurred in variable region. Conservative substitution basically means substitution with other amino acid residue having characteristics similar to the original amino acid sequence. For example, lysine, arginine, and histidine share similar characteristics by having a basic side chain, and aspartic acid and glutamic acid share similar characteristics by having an acidic side chain. Moreover, glycine, asparagine, glutamine, serine, threonine, tyrosine, cysteine, and tryptophan share similar characteristics by having an uncharged polar side chain, alanine, valine, leucine, threonine, isoleucine, proline, phenylalanine, and methionine similar characteristics by having a non-polar side chain, and tyrosine, phenylalanine, tryptophan, and histidine share similar characteristics by having an aromatic side chain. As such, it would be evident to a person skilled in the art that substitution of an amino acid within a group having similar characteristics as described above will not lead to any significant change in the characteristics. Thus, as long as the characteristics of the antibody of the present invention are maintained, an antibody having a mutation caused by conservative substitution within a variable region also falls within the scope of the present invention.

Considering a mutation having the biologically equivalent activity as described above, it is understood that, in the polypeptide sequence of the antibody or antibody fragment of the present invention, a sequence showing substantial identity with the sequence described with the sequence number is also included. The substantial identity means that, when the sequence of the present invention and other arbitrary sequence are aligned such that they correspond to each other as much as possible and the aligned sequences are analyzed by an algorithm generally used in the pertinent art, the sequences show homology of at least 61%, more preferably homology of at least 70%, even more preferably homology of at least 80%, most preferably homology of at least 90%, and preferably sequence identity of 95% or higher, 96% or higher, 97% or higher, 98% or higher, or 99% or higher. The alignment method for comparing sequences is well known in the pertinent art. Access to NCBI Basic Local Alignment Search Tool (BLAST) can be made through NBCI and the like, and, on the internet, it may be used in conjunction with a sequence analysis program like blastp, blasm, blastx, tblastn, and tblastx.

According to another aspect, the present invention relates to a polynucleotide encoding the bispecific antibody or an antigen binding fragment thereof.

By isolating a polynucleotide encoding the bispecific antibody or an antigen binding fragment thereof of the present invention, an antibody or an antigen binding fragment thereof can be produced by a recombination technique. The polynucleotide is isolated, and, after insertion to a replicable vector, further cloned (i.e., DNA amplification) or further expressed. Based on this, another aspect of the present invention relates to a vector including the polynucleotide.

"Polynucleotide" has a meaning which broadly encompasses DNA (gDNA and cDNA) and RNA molecules, for example. Nucleotide as a basic constitutional unit of nucleic acid includes not only a natural nucleotide but also an analogue having modified sugar or base moieties. The polynucleotide sequence encoding heavy chain and light chain variable regions of the present invention may be in modified form. The modification includes an addition, a deletion, or a non-conservative or conservative substitution of a nucleotide.

In one example, the polynucleotide encoding the bispecific antibody or an antigen binding fragment thereof of the present invention, for example, a polynucleotide encoding the heavy chain variable region of an antibody specifically binding to IL-17A or an antigen binding fragment thereof may be selected from the group consisting of SEQ ID NO: 42 to SEQ ID NO: 47. A polynucleotide encoding the light chain variable region may be SEQ ID NO: 48 or SEQ ID NO: 49. A polynucleotide encoding the heavy chain region of an antibody specifically binding to TNF-α (tumor necrosis factor-alpha) or an antigen binding fragment thereof may be SEQ ID NO: 86. A polynucleotide encoding the light chain region may be SEQ ID NO: 89.

It is understood that the nucleic acid of the present invention also encompasses a nucleotide sequence which shows substantial identity with the aforementioned nucleotide sequence. The substantial identity means that, when the nucleotide sequence of the present invention and other arbitrary sequence are aligned such that they correspond to each other as much as possible and the aligned sequences are analyzed by an algorithm generally used in the pertinent art, the sequences show homology of at least 80%, more preferably homology of at least 90%, and most preferably homology of at least 95%, and preferably sequence identity of 95% or higher, 96% or higher, 97% or higher, 98% or higher, or 99% or higher.

DNA encoding the aforementioned antibody can be easily isolated or synthesized by using a common process (for example, by using an oligonucleotide probe which can specifically bind to DNA encoding the heavy chain variable region and light chain variable region of an antibody). For further cloning or expression of the DNA, various vectors can be used. As a vector component, one or more of the followings are generally included, but it is not limited thereto: signal sequence, replication origin, one or more marker genes, enhancer element, promoter, and transcription termination sequence.

As described herein, the term "vector" is a means for expressing a target gene in host cell, and examples thereof include a plasmid vector; a cosmid vector; a bacteriophage vector; and a virus vector such as adenovirus vector, retrovirus vector, or adeno-associated virus. In the vector, a nucleic acid encoding the antibody is operably linked to a promoter.

The expression "operably linked" means a functional linking between a sequence for regulating nucleic acid expression (e.g., array on promoter, signal sequence, or transcription regulation factor binding site) and other nucleic acid sequence, and, according to the linking, transcription and/or translation of other nucleic acid sequence can be regulated by the regulation sequence.

When a prokaryotic cell is used as a host, a potent promoter enabling the progress of transcription (e.g., tac promoter, lac promoter, lacUV5 promoter, 1pp promoter, pLλ, promoter, pRλ, promoter, rac5 promoter, amp promoter, recA promoter, SP6 promoter, trp promoter, and T7 promoter), a ribosome binding site for initiation of translation, and a transcription/translation termination sequence are generally included. Moreover, when an eukaryotic cell is used as a host, a promoter derived from a genome of mammalian cells (e.g., metallothionine promoter, β-actin promoter, human hemoglobin promoter and human muscle creatine promoter) or a promoter derived from mammalian virus (e.g., adenovirus late promoter, vaccinia virus 7.5K promoter, SV40 promoter, cytomegalo virus (CMV) promoter, tk promoter of HSV, mouse breast tumor virus (MMTV) promoter, LTR promoter of HIV, moloney virus promoter, Epstein Barr virus (EBV) promoter and Rous sarcoma virus (RSV) promoter) can be used. As a transcription termination sequence, a polyadenylated sequence is generally included.

Depending on a case, the vector may be fused to other sequence for having easier purification of an antibody that is expressed by the vector. Examples of a sequence for fusion include glutathione S-transferase (Pharmacia, USA), maltose binding protein (NEB, USA), FLAG (IBI, USA) and 6×His (hexahistidine; Quiagen, USA), and the like The vector includes, as a selection marker, an antibiotics resistant gene generally used in the pertinent art, and examples thereof include a gene resistant to ampicillin, gentamycin, carbenicillin, chloramphenicol, streptomycin, kanamycin, geneticin, neomycin, or tetracycline.

According to another aspect, the present invention relates to a cell transformed with the aforementioned vector. A cell used for producing the bispecific antibody of the present invention may be a cell of a prokaryote, yeast, or a higher eukaryotic organism, but it is not limited thereto.

Bacterial strain belonging to Bacillus sp. such as *Escherichia coli*, *Bacillus subtilis*, and *Bacillus thuringiensis* or prokaryotic host cell such as *Streptomyces*, *Pseudomonas* (e.g., *Pseudomonas putida*), *Proteus mirabilis* or *Staphylococcus* (e.g., *Staphylococcus carnosus*) can be used.

Moreover, as a host cell, an animal cell currently receives the highest attention. Examples of the useful host cell line include COS-7, BHK, CHO, CHO-S, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080, but it is not limited thereto.

According to another aspect, the present invention relates to a method of producing the bispecific antibody or an antigen binding fragment thereof including: (a) culturing the transformed cell; and (b) collecting a bispecific antibody or an antigen binding fragment thereof from the obtained cell culture medium.

The cell can be cultured in various media, and a commercially available medium can be used as a medium without any limitation. Other essential complements known to a person skilled in the art may be also included at suitable concentration. Culture condition, e.g., temperature, pH and the like, are already employed with a host cell selected for expression, and it wound be evident to a person who is skilled in the art.

Collecting the antibody or an antigen binding fragment thereof can be achieved by removing impurities by centrifuge or ultrafiltration of cell culture medium and purifying the resultant by affinity chromatography or the like, for example. As an additional technique for purification, anion or cation exchange chromatography, hydrophobic interaction chromatography, hydroxyapatite chromatography or the like can be used.

According to another aspect, the present invention relates to an antibody-drug conjugate containing the bispecific antibody or an antigen binding fragment thereof, and a drug conjugated thereto.

The drug includes chemical substances, radionuclides, immunotherapeutic agents, cytokines, chemokines, toxins, biological agents, and enzyme inhibitors. For example, the antibody of the present invention or a fragment thereof may be directly or indirectly bound to an anti-cancer agent. Examples of the anti-cancer agent include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guetin (BCG), Baker's Antifol, beta-2-deoxythioguanosine, bisantrene HCl, bleomycin sulfate, busulfan, buthionine sulfoximine, BWA773U82, BW502U83/HCl, BW7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, Corynebacterium parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydro galactitol, diaziquone, dibromodulcitol, didemnin B, diethyldithiocarbamate, diglycoaldehyde, dihydro-5-azacytine, doxorubicin, echinomycin, dedatrexate, edelfosine, eplolnitin, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5'-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, 4-ipomeanole, iproplatin, isotretinoin, leucovorin calcium, leuprolide acetate, levamisole, liposome daunorubicin, liposome encapsulated doxorubicin, lomustine, lonidamine, maytansine, mechlorethamine hydrochloride, melphalan, menogaril, merbarone, 6-mercaptopurine, mesna, methanol extract of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, cytosine arabinoside, etoposide, melphalan, taxotele, and taxol.

According to another aspect of the present invention, the present invention relates to a pharmaceutical composition for preventing or treating an autoimmune disease comprising, as an active ingredient, the bispecific antibody or an antigen binding fragment thereof, or the antibody-drug conjugate. For example, the present invention may be related to a pharmaceutical composition for preventing or treating an autoimmune disease comprising (a) a pharmaceutically effective amount of the bispecific antibody or an antigen binding fragment thereof according to the present invention, or the antibody-drug conjugate; and (b) a pharmaceutically acceptable carrier.

According to still another aspect, the present invention relates to a method of preventing or treating an autoimmune disease including administering the bispecific antibody or an antigen binding fragment thereof, or the antibody-drug conjugate in an effective amount that is required by an individual.

The autoimmune disease may be selected from the group consisting of rheumatoid arthritis, psoriasis, psoriatic arthritis, ankylosing spondylitis, multiple sclerosis, interstitial fibrosis, lupus, glomerulonephritis, Crohn's disease, inflammatory bowel disease, autoimmune eye disease, children arthritis, Behcet's disease, deficiency of the IL-1 receptor antagonist (DIRA), TNF receptor-associated periodic syndrome (TRAPS), neonatal-onset multisystem inflammatory disease (NOMID), familial Mediterranean fever (FMF), and cryopyrin-associated periodic syndrome (CAPS), but it is not limited thereto.

"Preventing" means all activities for suppressing an autoimmune disease or delaying the progress of disease by administering the composition of the present invention, and "treat" means inhibition of development of an autoimmune disease, or alleviation or complete curing of an autoimmune disease.

The pharmaceutically acceptable carrier contained in the composition of the present invention is those ordinarily used at the time of formulating a pharmaceutical composition, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. Th composition of the present invention may further contain a lubricant, a wetting agent, a sweetening agent, a flavoring agent, an emulsifier, a suspending agent, a preservative, and the like, in addition to the above components.

As described herein, "individual" means a mammal suffering from or carrying a risk of having a condition or a disorder which can be alleviated, suppressed, or treated by administering the bispecific antibody of the present invention, and it preferably means a human.

As described herein, "administration" means the introduction of a certain substance to an individual by a certain suitable method. As long as the delivery to a target tissue is achieved, administration route of the composition comprising the bispecific antibody of the present invention can be any route including any general route. Examples of the administration route include intraperitoneal administration, intravenous administration, intramuscular administration, subcutaneous administration, oral administration, topical administration, intranasal administration, intrapulmonary administration, rectal administration, or the like, but it is not limited thereto. However, as the proteins are digested in case of oral administration, in case of the composition for oral administration, the active pharmaceutical agent is preferably coated or formulated such that it is protected from digestion in stomach. In addition, the pharmaceutical composition of the present invention may be administered by an arbitrary device for delivering the active material to target cells.

The appropriate dose of the composition of the present invention varies depending on factors, such as the formulating method, mode of administration, patient's age, body weight, gender, morbidity, and food, time of administration, route of administration, excretion rate, and response sensitivity. The ordinarily skilled practitioner can easily determine and prescribe the dose that is effective for the desired treatment or prevention. For example, the daily dose of the pharmaceutical composition of the present invention may be 0.0001 to 100 mg/kg, for example, dose of 1 mg/kg to 2 g/kg. The antibody or an antigen binding fragment thereof may be administered just once or several times. As described herein, the term "pharmaceutically effective amount" means an amount sufficient for preventing or treating an autoimmune disease.

The composition of the present invention may be administered as an individual therapeutic agent or administered in combination with other therapeutic agent it may be also sequentially or simultaneously administered with a conventional therapeutic agent.

The composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, an emulsion, an extract, a pulvis, a suppository, a powder, granules, a tablet, or a capsule, and it may further include a dispersant or a stabilizer.

EXAMPLES

Hereinbelow, the present invention is explained in greater detail in view of the examples. However, the examples are given only for exemplification of the present invention and by no means the scope of the present invention is limited by them.

Example 1: Expression and Purification of IL-17 Antigen 1-1: Construction of IL-17A Protein Expression Vector For cloning the extracellular domain gene of IL-17A, polymerase chain reaction (PCR) was carried out by having human IL-17A cDNA (Sinobiological, China, SEQ ID NO: 50) as a template and using the primers that are described in Table 3. The amplified PCR product was inserted to N293F vector to produce IL-17A-N293F vector which expresses a protein having His-tag fused to the C-terminus of IL-17A. DH5α E. coli cells were transformed with thus-constructed IL-17A-N293F vector and ampicillin-resistant cells were selected. Based on digestion using the restriction enzymes of SfiI and XhoI followed by sequencing, it was determined whether IL-17A-His gene (SEQ ID NO: 51) has been successfully inserted or not. In the same manner as above, a vector expressing mouse IL-17A-His was also constructed.

TABLE 3

| Name | 5'→3' Sequence |
| --- | --- |
| IL-17A-F | ggaatcacaatcccacgaaat (SEQ ID NO: 52) |
| IL-17A-R | ggccacatggtggacaatcgg (SEQ ID NO: 53) |

1-2: Expression and Purification of IL-17A Antigen

To produce human IL-17A-His (hIL-17A-His) or mouse IL-17A-His (mIL-17A-His) antigen, HEK293F cells were inoculated to freestyle medium (Gibco, cat. A13835) at $5 \times 10^5$ cells/ml followed by culture for 1 day. Then, HEK293F cells were transfected with IL-17A-N293F vector produced in Section 1-1 above by using PEI (polyethylenimine, Aldrich, cat. 408727). After forming polyplex by admixing the plasmid with PEI at 1:2 (w/w), the cells were transfected. Cell culture medium obtained after culture for 7 days was subjected to SDS-PAGE and then transferred to a PVDF membrane. Following the treatment with anti-His HRP antibody, expression was determined by using ECL substrate.

Culture medium of the expressed hIL-17A-His and mIL-17A-His was separately isolated and purified by Ni-NTA column, subjected to SDS-PAGE, and then stained with CBR-250 to analyze the protein.

Example 2: Selection of IL-17 Antibody 2-1. Biopanning

To select antibody candidates which specifically bind to hIL-17A, the phage display technique and Ymax-nABL library (YBiologics, South Korea) composed of naive cDNA of human B cells were employed.

hIL-17A-His produced in Example 1 was coated onto an immuno tube, added with library phage, reacted for 2 hours at room temperature, and then washed with 1×PBST and 1×PBS. Thereafter, scFv-phage specifically bound to the library phage was eluted. According to a panning process in which the eluted scFv-phage is used again for E. coli infection to have amplification, pool of a positive phage was obtained. Then, except that the number of PBST washing has been increased, the second and the third pannings were repeatedly carried out in the same manner as the 1st panning while having the phage amplified by the first panning as a subject.

As a result of determining the CFU of hIL-17A phage antibody pool obtained by the 1st to the 3rd pannings, it was found that the output of the 3$^{rd}$ panning is almost 10 times higher than the output CFU of the 1$^{st}$ and the 2$^{nd}$ pannings.

2-2: Selection of IL-17A Specific Antibody

To determine the antigen specificity for the positive poly ScFv-phage antibody pool which has been obtained from each round of panning, polyphage ELISA (enzyme linked immunoassay) was carried out. For the immune-plate coated with mouse IL-17A-His antigen for examining cross-binding for mouse antigen and human IL-17A-His antigen that have been used for the panning, direct ELISA was carried out using the phage pool obtained from each round. As a result, it was found that the binding property for hIL-17A-His antigen has increased mainly in the 3$^{rd}$ poly ScFv-phage, indicating that anti-IL-17A phage antibody is present in increased number in the positive phage pool of the 3$^{rd}$ panning.

E. coli containing monoclones were randomly selected from the positive phage pool of the 3$^{rd}$ panning, cultured to a mid-log phase at 37° C., 300 rpm in a 96-deep well plate which has been treated with 2×YT/C culture medium, and infection of helper phage was induced. Cells were pelletized by centrifuge for 10 minutes at 6000 rpm and only the eluted mono scFv-phage present in the supernatant was obtained.

Human IL-17A-His and BSA were coated, each at 0.4 µg/ml, on a Maxisorb 96 well ELISA plate (Nunc, Denmark), and, after blocking with PBST containing 3% skim milk, mono scFv-phage obtained above was added to the well coated with each antigen. The ELISA plate was washed 3 times with 0.05% PBST and added with anti-M13-HRP (Horse Radish Peroxidase) antibody which has been diluted to 0.05% in PBST followed by a reaction for 1 hour. After having color development by treating for 10 minutes with OPD (o-phenylenediamine dihydrochloride) substrate, treatment with 2 N H$_2$SO$_4$ was carried out to terminate the reaction. Absorbance at 490 nm was measured for the plate by using SpectraMax ELISA reader (Molecular device, U.S.A) after having color development. As a result, dozens of mono scFv-phage clones which show the binding signal to hIL-17A-his at least 3 times higher than the signal binding to BSA used as a reference antigen were selected.

For the monoclones selected above, phagemid DNA was isolated by using DNA purification kit (Qiagen, Germany). By analyzing the nucleotide sequence of the isolated DNA and sequence of the heavy chain and light chain, specific clones having different sequence were determined. Next, by carrying out affinity maturation for modifying the heavy chain to have enhanced affinity, scFv specific to IL-17A was selected. Sequence of the antibody specific to IL-17A is described in the following Table 4 (heavy chain CDR and heavy chain variable region) and Table 5 (light chain CDR and light chain variable region).

TABLE 4

| Antibody | | H-CDR1 | H-CDR2 | H-CDR3 |
|---|---|---|---|---|
| 7D1 | | SYTMH (SEQ ID NO: 1) | ISFDGRSKLYGDSVRD (SEQ ID NO: 2) | RGREGEDAFDL (SEQ ID NO: 3) |
| | FR1 | | QVQLVESGGGVAQPGRSLRLSCAASGFAFG (SEQ ID NO: 15) | |
| | FR2 | | WVRQAPGKGLEWVTL (SEQ ID NO: 16) | |
| | FR3 | | RFTISRDNSKNMLYLKISDLRSEDTAVYYCAR (SEQ ID NO: 17) | |
| | FR4 | | WGQGTMVTVSS (SEQ ID NO: 18) | |
| | VH | | QVQLVESGGGVAQPGRSLRLSCAASGFAFGSYTMHWV RQAPGKGLEWVTLISFDGRSKLYGDSVRDRFTISRDNS KNMLYLKISDLRSEDTAVYYCARRGREGEDAFDLWGQ GTMVTVSS (SEQ ID NO: 34) | |
| 7H3C11FW | | SYTMH (SEQ ID NO: 1) | ISFDGRSKLYGDSVKG (SEQ ID NO: 4) | GSVRGEAAFDL (SEQ ID NO: 5) |
| | FR1 | | QVQLVESGGGVVQPGRSLRLSCAASGFAFG (SEQ ID NO: 19) | |
| | FR2 | | WVRQAPGKGLEWVTL (SEQ ID NO: 16) | |
| | FR3 | | RFTISRDNSKNSLYLQMNSLRAEDTAVYYCAR (SEQ ID NO: 20) | |
| | FR4 | | WGQGTLVTVSS (SEQ ID NO: 21) | |
| | VH | | QVQLVESGGGVVQPGRSLRLSCAASGFAFGSYTMHWV RQAPGKGLEWVTLISFDGRSKLYGDSVKGRFTISRDNS KNSLYLQMNSLRAEDTAVYYCARGSVRGEAAFDLWG QGTLVTVSS (SEQ ID NO: 35) | |
| 7H3B6FW | | SYTMH (SEQ ID NO: 1) | ISFDGRSKLYGDSVKG (SEQ ID NO: 4) | GSKLGEDAFDL (SEQ ID NO: 6) |
| | FR1 | | QVQLVESGGGVVQPGRSLRLSCAASGFAFG (SEQ ID NO: 19) | |
| | FR2 | | WVRQAPGKGLEWVTL (SEQ ID NO: 16) | |
| | FR3 | | RFTISRDNSKNSLYLQMNSLRAEDTAVYYCAR (SEQ ID NO: 20) | |
| | FR4 | | WGQGTLVTVSS (SEQ ID NO: 21) | |
| | VH | | QVQLVESGGGVVQPGRSLRLSCAASGFAFGSYTMHWV RQAPGKGLEWVTLISFDGRSKLYGDSVKGRFTISRDNS KNSLYLQMNSLRAEDTAVYYCARGSKLGEDAFDLWG QGTLVTVSS (SEQ ID NO: 36) | |

TABLE 4 -continued

| Antibody | H-CDR1 | H-CDR2 | H-CDR3 |
|---|---|---|---|
| 7H3C12FW | SYTMH (SEQ ID NO: 1) | ISFDGRSKLYGDSVKG (SEQ ID NO: 4) | GSRIGEDAFDL (SEQ ID NO: 7) |
| | FR1 | QVQLVESGGGVVQPGRSLRLSCAASGFAFG (SEQ ID NO: 19) | |
| | FR2 | WVRQAPGKGLEWVTL (SEQ ID NO: 16) | |
| | FR3 | RFTISRDNSKNSLYLQMNSLRAEDTAVYYCAR (SEQ ID NO: 20) | |
| | FR4 | WGQGTLVTVSS (SEQ ID NO: 21) | |
| | VH | QVQLVESGGGVVQPGRSLRLSCAASGFAFGSYTMHWVRQAPGKGLEWVTLISFDGRSKLYGDSVKGRFTISRDNSKNSLYLQMNSLRAEDTAVYYCARGSRIGEDAFDLWGQGTLVTVSS (SEQ ID NO: 37) | |
| 9E12 | DHAMH (SEQ ID NO: 8) | SLISGDGGATYYADSVKG (SEQ ID NO: 9) | HFSDSRGRSDVPFDI (SEQ ID NO: 10) |
| | FR1 | QVQLVESGGGVVQPGGSLRLSCAASGFTFD (SEQ ID NO: 22) | |
| | FR2 | WVRQAPGKGLEWV (SEQ ID NO: 23) | |
| | FR3 | RFIISRDNSKNSLYLQMNSLRAEDTAVYYCAR (SEQ ID NO: 24) | |
| | FR4 | WGQGTLITVSS (SEQ ID NO: 25) | |
| | VH | QVQLVESGGGVVQPGGSLRLSCAASGFTFDDHAMHWVRQAPGKGLEWVSLISGDGGATYYADSVKGRFIISRDNSKNSLYLQMNSLRAEDTAVYYCARHFSDSRGRSDVPFDIWGQGTLITVSS (SEQ ID NO: 38) | |
| 9H2D9 | DHAMH (SEQ ID NO: 8) | GLIGPDGGATYYADSVKG (SEQ ID NO: 11) | HFSDSRGRSDVPFDI (SEQ ID NO: 10) |
| | FR1 | QVQLVESGGGVVQPGGSLRLSCAASGFTFD (SEQ ID NO: 22) | |
| | FR2 | WVRQAPGNGLEWV (SEQ ID NO: 26) | |
| | FR3 | RFIISRDNSKNSLYLQMNSLRAEDTAVYYCAR (SEQ ID NO: 24) | |
| | FR4 | WGQGTLITVSS (SEQ ID NO: 25) | |
| | VH | QVQLVESGGGVVQPGGSLRLSCAASGFTFDDHAMHWVRQAPGNGLEWVGLIGPDGGATYYADSVKGRFIISRDNSKNSLYLQMNSLRAEDTAVYYCARHFSDSRGRSDVPFDIWGQGTLITVSS (SEQ ID NO: 39) | |

TABLE 5

| Antibody | L-CDR1 | L-CDR2 | L-CDR3 |
|---|---|---|---|
| 7D1 | SGDNLRTKYVS (SEQ ID NO: 12) | QDTRRPS (SEQ ID NO: 13) | MTWDVDTTSM (SEQ ID NO: 14) |
| | FR1 | SYELTQAPSLSVSPGQTANIIC (SEQ ID NO: 27) | |
| | FR2 | WYQQKPGQSPLLVIY (SEQ ID NO: 28) | |
| | FR3 | GIPARFSGSNSGNTATLTISGTQTRDESTYYC (SEQ ID NO: 29) | |
| | FR4 | IFGGGTKLTVL (SEQ ID NO: 30) | |
| | VL | SYELTQAPSLSVSPGQTANIICSGDNLRTKYVSWYQQKPGQSPLLVIYQDTRRPSGIPARFSGSNSGNTATLTISGTQTRDESTYYCMTWDVDTTSMIFGGGTKLTVL (SEQ ID NO: 40) | |
| 7H3C11FW | SGDNLRTKYVS (SEQ ID NO: 12) | QDTRRPS (SEQ ID NO: 13) | MTWDVDTTSM (SEQ ID NO: 14) |
| | FR1 | SYELTQPPSVSVSPGQTASITC (SEQ ID NO: 31) | |
| | FR2 | WYQQKPGQSPVLVIY (SEQ ID NO: 32) | |
| | FR3 | GIPERFSGSNSGNTATLTISGTQAMDEADYYC (SEQ ID NO: 33) | |
| | FR4 | IFGGGTKLTVL (SEQ ID NO: 30) | |
| | VL | SYELTQPPSVSVSPGQTASITCSGDNLRTKYVSWYQQKPGQSPVLVIYQDTRRPSGIPERFSGSNSGNTATLTISGTQAMDEADYYCMTWDVDTTSMIFGGGTKLTVL (SEQ ID NO: 41) | |

TABLE 5 -continued

| Antibody | L-CDR1 | L-CDR2 | L-CDR3 |
|---|---|---|---|
| 7H3B6FW | SGDNLRTKYVS (SEQ ID NO: 12) | QDTRRPS (SEQ ID NO: 13) | MTWDVDTTSM (SEQ ID NO: 14) |
| | FR1 | SYELTQPPSVSVSPGQTASITC (SEQ ID NO: 31) | |
| | FR2 | WYQQKPGQSPVLVIY (SEQ ID NO: 32) | |
| | FR3 | GIPERFSGSNSGNTATLTISGTQAMDEADYYC (SEQ ID NO: 33) | |
| | FR4 | IFGGGTKLTVL (SEQ ID NO: 30) | |
| | VL | SYELTQPPSVSVSPGQTASITCSGDNLRTKYVSWYQQKPGQSPVLVIYQDTRRPSGIPERFSGSNSGNTATLTISGTQAMDEADYYC<u>MTWDVDTTSM</u>IFGGGTKLTVL (SEQ ID NO: 41) | |
| 7H3C12FW | SGDNLRTKYVS (SEQ ID NO: 12) | QDTRRPS (SEQ ID NO: 13) | MTWDVDTTSM (SEQ ID NO: 14) |
| | FR1 | SYELTQPPSVSVSPGQTASITC (SEQ ID NO: 31) | |
| | FR2 | WYQQKPGQSPVLVIY (SEQ ID NO: 32) | |
| | FR3 | GIPERFSGSNSGNTATLTISGTQAMDEADYYC (SEQ ID NO: 33) | |
| | FR4 | IFGGGTKLTVL (SEQ ID NO: 30) | |
| | VL | SYELTQPPSVSVSPGQTASITCSGDNLRTKYVSWYQQKPGQSPVLVIYQDTRRPSGIPERFSGSNSGNTATLTISGTQAMDEADYYC<u>MTWDVDTTSM</u>IFGGGTKLTVL (SEQ ID NO: 41) | |
| 9E12 | SGDNLRTKYVS (SEQ ID NO: 12) | QDTRRPS (SEQ ID NO: 13) | MTWDVDTTSM (SEQ ID NO: 14) |
| | FR1 | SYELTQAPSLSVSPGQTANIIC (SEQ ID NO: 27) | |
| | FR2 | WYQQKPGQSPLLVIY (SEQ ID NO: 28) | |
| | FR3 | GIPARFSGSNSGNTATLTISGTQTRDESTYYC (SEQ ID NO: 29) | |
| | FR4 | IFGGGTKLTVL (SEQ ID NO: 30) | |
| | VL | SYELTQAPSLSVSPGQTANIICSGDNLRTKYVSWYQQKPGQSPLLVIYQDTRRPSGIPARFSGSNSGNTATLTISGTQTRDESTYYC<u>MTWDVDTTSM</u>IFGGGTKLTVL (SEQ ID NO: 40) | |
| 9H2D9 | SGDNLRTKYVS (SEQ ID NO: 12) | QDTRRPS (SEQ ID NO: 13) | MTWDVDTTSM (SEQ ID NO: 14) |
| | FR1 | SYELTQPPSVSVSPGQTASITC (SEQ ID NO: 31) | |
| | FR2 | WYQQKPGQSPVLVIY (SEQ ID NO: 32) | |
| | FR3 | GIPERFSGSNSGNTATLTISGTQAMDEADYYC (SEQ ID NO: 33) | |
| | FR4 | IFGGGTKLTVL (SEQ ID NO: 30) | |
| | VL | SYELTQPPSVSVSPGQTASITCSGDNLRTKYVSWYQQKPGQSPVLVIYQDTRRPSGIPERFSGSNSGNTATLTISGTQAMDEADYYC<u>MTWDVDTTSM</u>IFGGGTKLTVL (SEQ ID NO: 41) | |

Example 3: Preparation of Bispecific Antibody Targeting IL-17A and TNF-α

3-1: Production of Bispecific Antibody

To produce a bispecific antibody in which an anti IL-17A antibody and Humira, which is and anti TNF-α antibody, are fused, among the anti IL-17A antibody monoclones produced in Example 2 above, scFv of 7H3C11FW was linked to the 3'-terminus of Humira heavy chain nucleic acid sequence, and the resultant was named "SDA-0070".

Humira (adalimumab) as an anti-TNF-α antibody was produced by gene synthesis based on the amino acid sequence (SEQ ID NO: 64) including heavy chain variable region and the amino acid sequence (SEQ ID NO: 70) including light chain variable region. Next, a linker was introduced to the 3'-terminus of the nucleic acid sequence (SEQ ID NO: 86) of heavy chain of Humira (adalimumab) as an anti-TNF-α antibody, and, with use of anti IL-17A VH and VL obtained by optimization after the introduction, scFv nucleic acid sequence (SEQ ID NO: 87) was linked. Amino acid sequence of the heavy chain of thus-prepared bispecific antibody was represented by SEQ ID NO: 76.

To produce and prepare the bispecific antibody in protein form, transient expression was induced by using HEK293F as a production cell. Into the vector named N293F, the nucleic acid sequence of the above bispecific antibody was inserted to give a plasmid construct, which was then admixed with polyethlyeneimine to form polyplex. HEK293F cells were then transfected by a treatment with the polyplex, and cultured for 6 days using Free style medium (Gibco, U.S.A). Culture medium was centrifuged at 8000 rpm to remove cell debris, and, by using a bottle top filter (Millipore, Steritop-GP Filter Unit. Cat. No. SCGPS01RE), pure culture medium was obtained.

3-2: Purification of Antibody

To isolate and purify the TNF-α/IL-17A bispecific antibody present in culture medium, as a first purification, affinity purification was carried out by using Protein A resin (KANEKA, Japan). To an empty column (Bio-rad, BR731-1550), Protein A (4 ml) was added and the resin was packed and washed with 100 ml of DPBS (LB001-02). The resin-packed column was added with the medium, which was then allowed to flow at rate of 1 ml/minute. After washing with 150 ml DPBS, elution was performed using 0.1 M glycine-HCl (pH 3.3, 10 ml). The eluent was then added with 1 M Tris-HCl (pH 9.0) to a level of 10% to neutralize the pH. By using Amicon Ultra-15 (Millipore, UFC901096), the buffer was changed to DPBS. After repeating about 3 times, the above process was terminated when concentration to 1 ml or so is achieved. Then, the concentration was examined, i.e., for measuring the concentration, UV quantification was carried out by using Epoch (Biotek, U.S.A)

To remove high-molecular weight materials, gel filtration chromatography using Superdex200 resin (GE healthcare, U.S.A) was carried out as a second purification. After 2CV equilibration using DPBS (Welgene Inc., South Korea) as a mobile phase and filtering the purified protein with 0.22 µm syringe filter (Millipore, SLGP033RB), 10 ml of the first-purified protein were applied to a sample loop. The loaded protein was injected to a column and fractions corresponding to the target molecule were pooled. Pooled fractions were concentrated by using Amicon Ultra-15 (Millipore, UFC905096), and then subjected to sterile-filtration using 0.22 µm syringe filter (Millipore, SLGP033RB).

3-3: SDS-PAGE and HPLC

Purified protein was prepared as a mixture with a reducing or a non-reducing buffer, respectively. For isolating the protein, acrylamide separation gels (Translab, South Korea) were prepared, each at 12%, and set in a running tank (BioRad, U.S.A). After filling it with 1× running buffer, 2 µg of the sample were loaded. In the separation gel, a well loaded with protein size marker (BioRad, U.S.A) was included, one well for each gel. After completing the loading, an electrode was connected in direction of from (−) to (+) and electrophoresis was performed at 200 V, which was continued until the brilliant blue dye in loading buffer reaches the gel bottom. The separation gel after electrophoresis was stained with Coomassie blue staining reagent and, after destaining with a destaining buffer, remaining reagents were removed with distilled water (D.W.) and separation pattern of the marker and purified protein was analyzed (FIG. 1). After the gel filtration chromatography (GFC) purification, the antibody was determined based on an analysis using size exclusion (SE)-HPLC.

Example 4: Analysis of Binding Specificity of Bispecific Antibody

In order to determine the antigen binding specificity of the bispecific antibody, ELISA was carried out. Each of human IL-17A and mouse IL-17A (R&D system, U.S.A), marmorset IL-17A (Sino biological, China), cynomolgus IL-17A, human TNF-α (Peprotech, U.S.A), human IL-17F (R&D system, U.S.A), human IL-17A/F (R&D system, U.S.A), and BSA was O/N-coated, at 15 nM for each, 37° C., on a 96-well plate. Thereafter, uncoated areas were blocked with 3% skim milk/0.05% PBST. IL-17A antibody was then added, at 66 nM, 6.6 nM, or 0.6 nM, to the plate and the reaction was allowed to occur for 1 hour at 37° C. Anti human Fc-HRP (pierce, U.S.A) was diluted (1:3000) and then reacted for 1 hour. Next, color development was carried out by treating for 10 minutes with TMB substrate (BD, U.S.A), and the reaction was terminated by a treatment with 2 N $H_2SO_4$. Absorbance at 450 nm of the plate after color development was then measured by using Sunrise ELISA reader (TECAN, Switzerland).

Figure 2A:
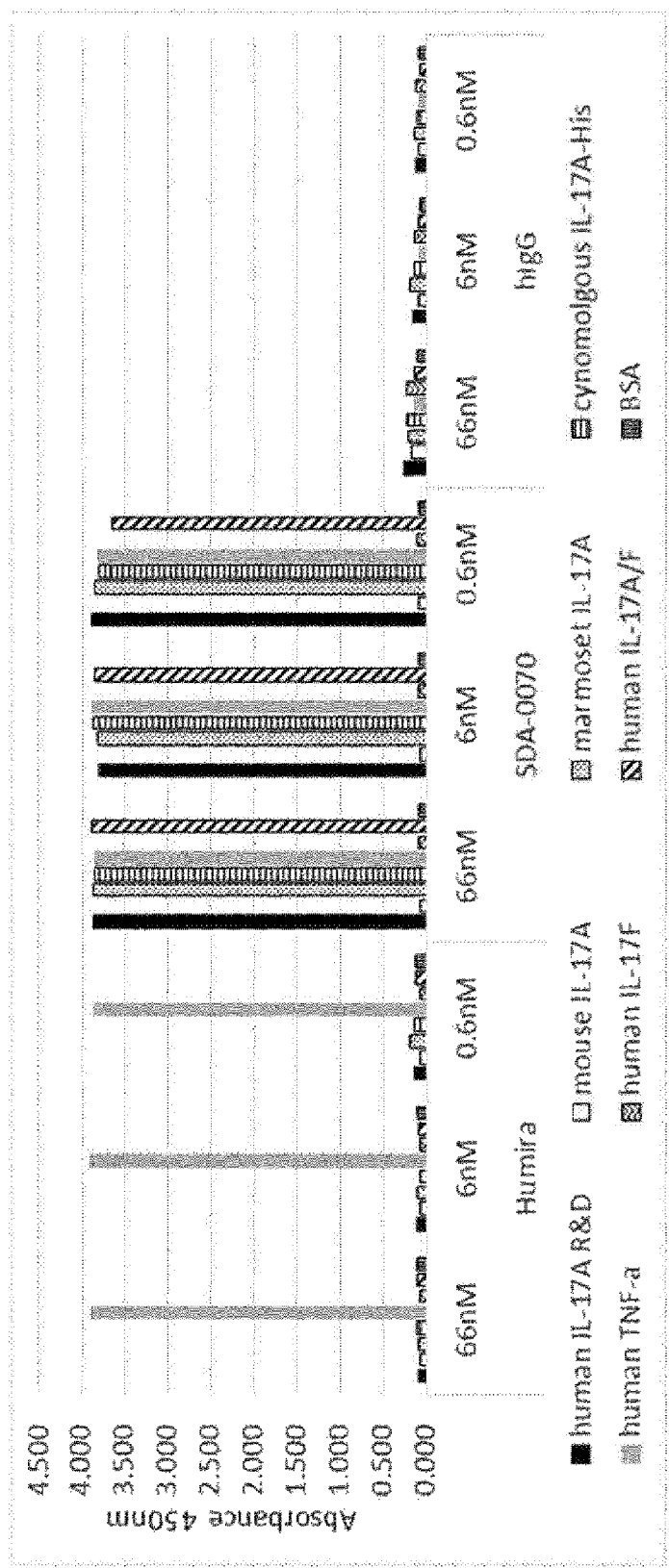
FIGS. 2a to 2c show the result of ELISA analysis of SDA-0070 indicating that SDA-0070 is a bispecific antibody showing specific binding property only for IL-17A and TNF-α without having any non-specific binding property.
Figure 2B:
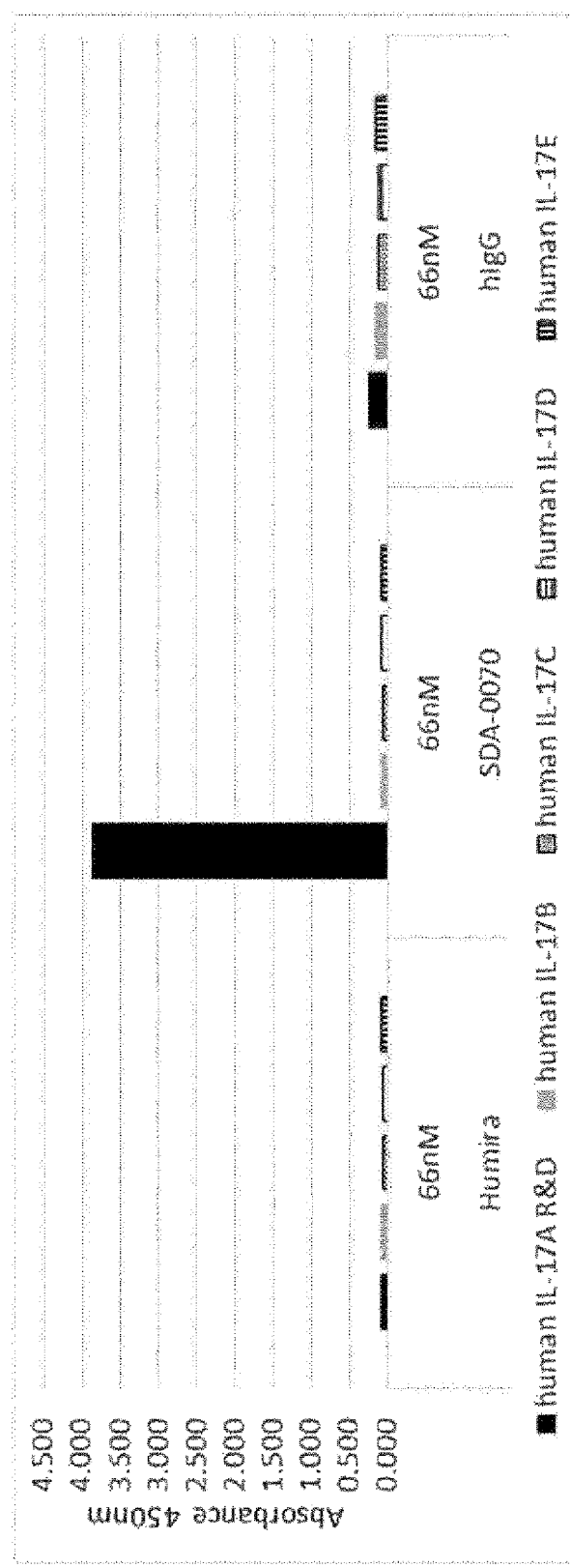
Figure 2C:
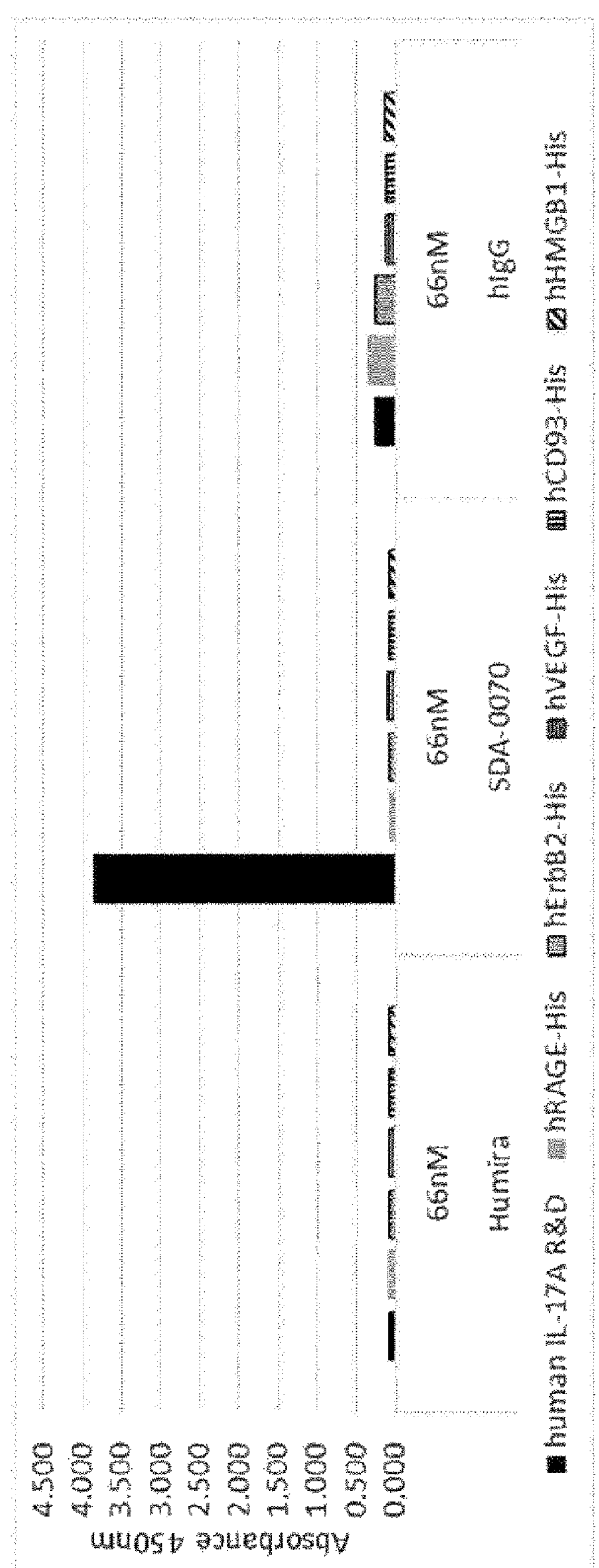

As a result, unlike human TNF-α monospecific antibody, the bispecific antibody binds not only to human TNF-α but also to human IL-17A, and it maintains the binding to the marmoset, cynomolgus, and IL-17A/F heterodimer (FIG. 2a). Moreover, it did not show any binding to IL-17B, IL-17C, IL-17D, and IL-17E, which correspond to IL-17 ligand family, and also had no binding to non-specific antigen proteins like human RAGE-his, human ErbB2-his, human VEGF-his, human CD93-His, and human HMGB1-His, (FIG. 2b and FIG. 2c). Thus, it was found that the antibody of the present invention is a very specific antibody which shows enhanced binding only to human TNF-α and human IL-17A or IL-17A/F.

Example 5: Evaluation of Co-Binding Property of Bispecific Antibody for Two Antigens Using ELISA To determine the co-binding property of bispecific antibody for IL-17A and TNF-α as a target, enzyme linked immunoassay in which target antigen TNF-α is coated and detection is made by using remaining target antigen IL-17A was employed.

TNF-α (Peprotech, U.S.A) was diluted in DPBS (Welgene Inc., South Korea) at 0.26 µg/ml, and treated in an amount of 100 µl per well of a 96-well plate (Corning, U.S.A). By allowing it to stand for 16 hours at 4° C., coating was carried out. As a washing buffer, PBS-T (0.1% Tween 20) was used, and, for blocking, skim milk (BDbiosciences, U.S.A) was diluted to 3% in PBS-T and used. The antibody sample was subjected to serial dilution, i.e., 10 times for each dilution starting from 6.6 nM, and total 5 point dilution was performed till to have 660 fM. The diluted antibody sample was treated in an amount of 100 µl per well followed by reaction for 1 hour at 25° C. Then, as a secondary antibody, anti-His-HRP (Thermofisher Scientific, U.S.A) was diluted at 1:5000, and treated in an amount of 100 µl per well followed by reaction for 1 hour at 25° C. As a substrate, TMB (Sigma Aldrich, U.S.A) was used, which was added in an amount of 100 µl per well. After reacting them for 20 minutes, the reaction was terminated by a treatment with 2 N $H_2SO_4$, and absorbance at 450 nm was measured by using Multiskan™ GO Microplate Spectrophotometer (Thermofisher Scientific, U.S.A).

Figure 3:
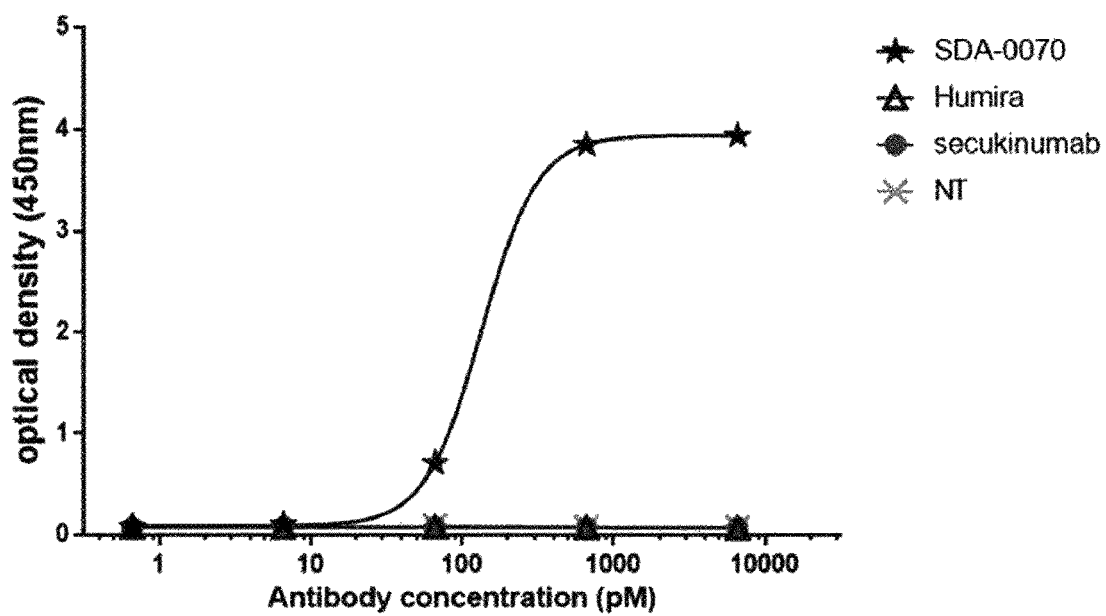
FIG. 3 shows the result of ELISA in which SDA-0070 shows bispecific binding to IL-17A and TNF-α.

As a result, the monospecific antibody showed no binding reaction at all, but the bispecific antibody showed the co-binding reaction with TNF-α and IL-17A in accordance with concentration gradient (FIG. 3 and Table 6).

TABLE 6

| $EC_{50}$ of each antibody for TNF-α and IL-17A antigens | | | |
|---|---|---|---|
| | SDA-0070 | Humira | Secukinumab |
| $EC_{50}$ (pM) | 133.7 | — | — |

Example 6: Efficacy Evaluation of Cation Exchange Chromatography (CEX) Purified Product of SDA-0070 Using HT-29 Cell Analysis HT-29 (*Homo sapiens* colorectal adenocarcinoma) (South Korea Cell Line Bank, South Korea) used for the test is a cell line derived from adenocarcinoma and it is known to respond to IL-17 and TNF-α to secret various immunocytokines, CXCL-1 (human GRO-α) as an immunochemokine, and the like. Cells obtained after at least 3 subcultures using RPMI1640 (Hyclone, U.S.A) medium containing 10% fetal bovine serum (Gibco, U.S.A), 1% antibiotics, and anti-anti (penicillin/streptomycin/anti-mycoplasma; Gibco, U.S.A) were used.

For examining the neutralization property, three tests including single neutralization property test for IL-17A, single neutralization property test for TNF-α, and co-neutralization property test for IL17-A and TNF-α were carried out. IL-17A and TNF-α were either diluted independently or admixed with each other to give a diluted product. The antibody sample was diluted, by 2 times for each dilution, from 736 pM to 0.36 pM so that the treatment can be carried out with total 12 concentrations. Each diluted antibody and diluted antigen prepared in advance were admixed in a 96-well plate and reacted at 37° C. for 1 hour. The plate upon completion of the antigen-antibody reaction was subjected to trypsin-EDTA treatment. HT-29 cells collected after the treatment were seeded at $7.5 \times 10^4$ cells/well and cultured for 48 hours in an environment of 37° C., 5% $CO_2$. After 48 hours, culture medium except the cells was collected. CXCL-1 concentration in the collected culture medium was measured by using ELISA kit Human CXCL-1 (R&D systems, U.S.A) so that the neutralization property of antibody against antigen was evaluated.

Figure 4A:
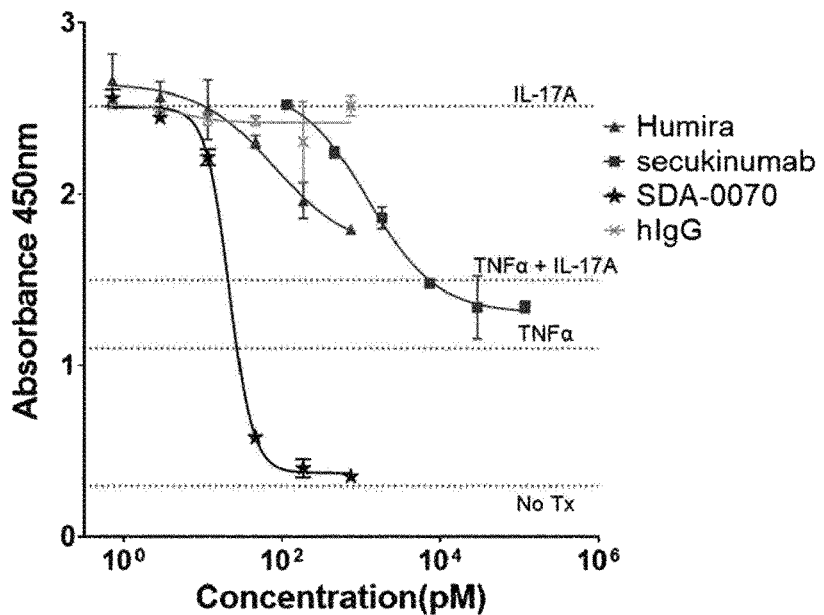
FIGS. 4a to 4c show the result of evaluating the neutralization property of SDA-0070 in human HT-29 cells.
Figure 4B:
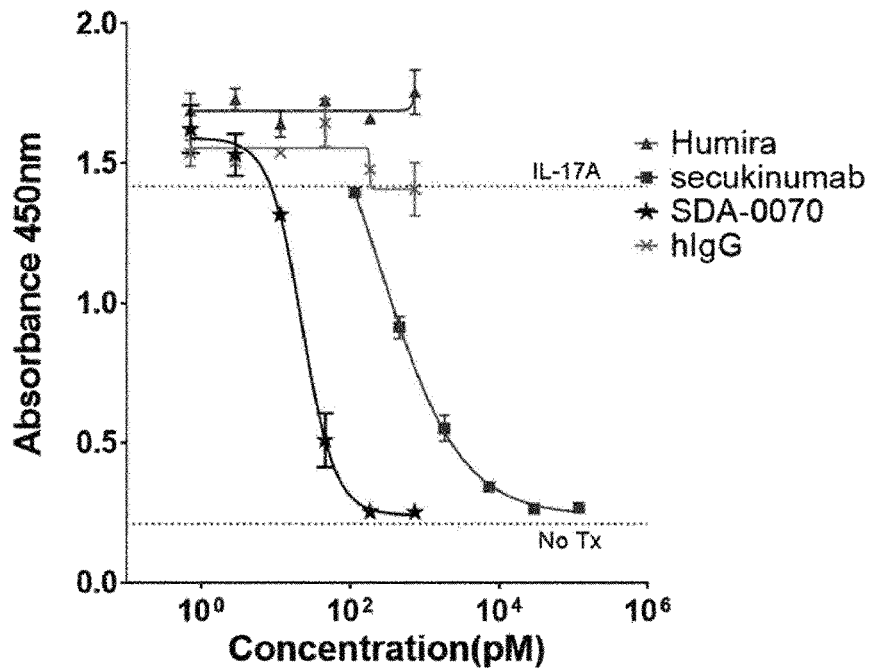
Figure 4C:
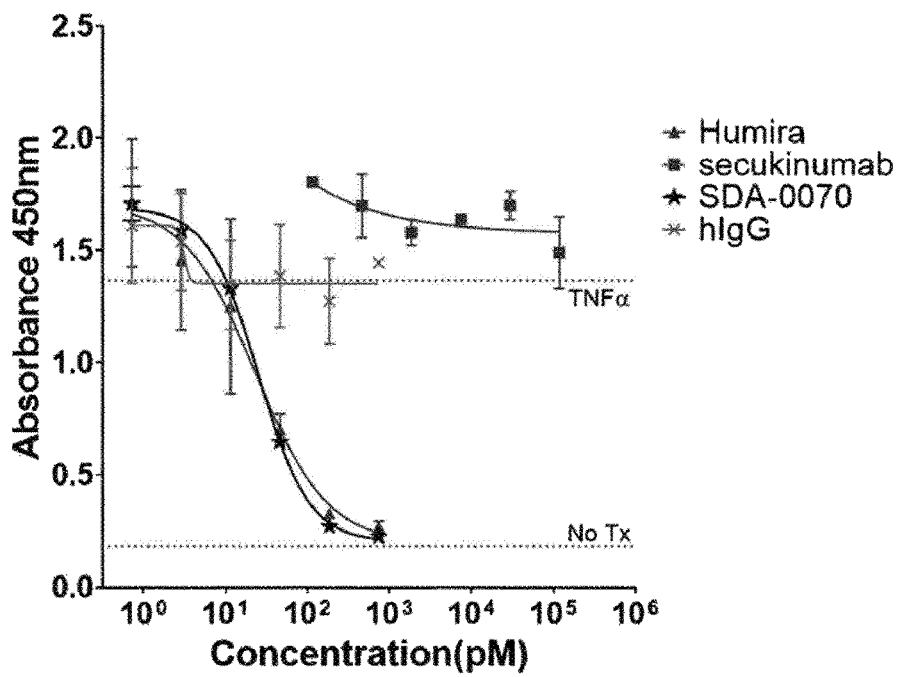

As a result of comparing the neutralization property for SDA-0070, it was found that the neutralization property of the bispecific antibody for IL-17A and the neutralization property of the bispecific antibody for TNF-α are slightly better than the result obtained from monospecific antibody, and therefore the co-neutralization property for IL-17A and TNF-α also tends to be more favorable (FIGS. 4a to 4c and Table 7). In the following Table 7, the result of evaluating the inhibitory activity of SDA-0070 clones using HT-29 cells is given.

TABLE 7

| Name | IL-17A + TNF-α $IC_{50}$ (pM) | IL-17A $IC_{50}$ (pM) | TNF-α $IC_{50}$ (pM) |
|---|---|---|---|
| Humira | 80.45 | | 23.2 |
| Secukinumab | 1229 | 258.8 | |
| SDA-0070_CEX | 21.55 | 22.72 | 25.15 |

Example 7: Efficacy Evaluation of CEX Purified Product of SDA-0070 Using Reporter Cell Analysis By using HEK-Blue™ IL-17 cell line (Invivogen, U.S.A) expressing IL-17RA and IL-17RC as an IL-17 receptor and HEK-Blue™ TNF-α cell line (Invivogen, U.S.A) expressing TNFRI and TNFRII as a TNF-α receptor, the neutralization property for IL-17A and TNF-α was evaluated. For culture of HEK-Blue cell lines, DMEM-HG (Hyclone, U.S.A) containing 10% fetal bovine serum (Gibco, U.S.A), 1% antibiotics, and Anti-anti (penicillin/streptomycin/anti-mycoplasma; Gibco, U.S.A) was used. As a selection antibiotic for maintaining the expression of each receptor and SEAP, zeocin (Invivogen, U.S.A) was used. For HEK-Blue™ IL-17 cell line, HEK-Blue™ Selection (Invivogen, U.S.A), which is a mixture of antibiotics, was additionally used. All cells used for the test were the cells which have been subcultured at least 3 times, and, when recovering the cells from a culture plate, Accutase (Merck Millipore, Germany) was used. A diluted product of each antigen was prepared such that IL-17A (R&D, U.S.A) has final concentration of 0.6 ng/ml and TNF-α (R&D, U.S.A) has final concentration of 0.4 ng/ml. Each antibody sample was diluted, 2 times for each dilution, starting from 736 pM to 0.36 pM so that the treatment can be made with total 12 concentrations. The diluted antibody and diluted antigen were admixed with each other in a 96-well plate followed by reaction for 1 hour at 37° C. The HEK-Blue™ IL-17 cells and HEK-Blue™ TNF-α cells recovered by Accutase were seeded, at $5 \times 10^4$ cells per well, to the plate having completed antigen-antibody reaction, and they were cultured for 24 hours in an environment of 37° C., 5% $CO_2$. After 24 hours, culture medium except the cells was collected. To the collected culture medium, QUANTI-Blue™ medium (Invivogen, U.S.A) solution was added and cultured at 37° C. Then, depending on the resulting substrate reaction rate, absorbance at 622 nm was measured within 20 minutes to 60 minutes by using Multiskan™ GO Microplate Spectrophotometer (Thermofisher Scientific, U.S.A).

Figure 5A:
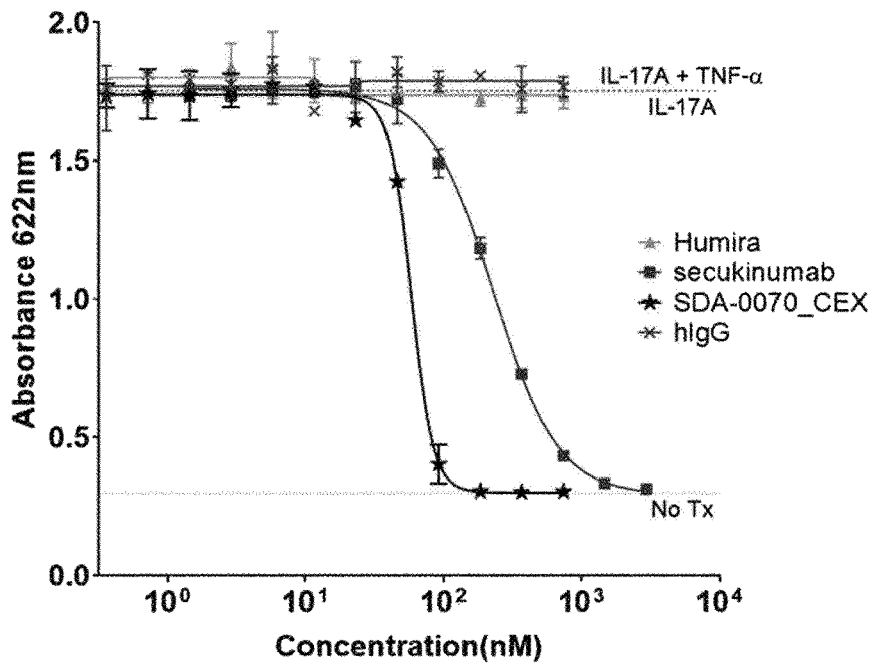
FIGS. 5a and 5b show the result of evaluating the neutralization property of SDA-0070 in HEK blue derived cells.
Figure 5B:
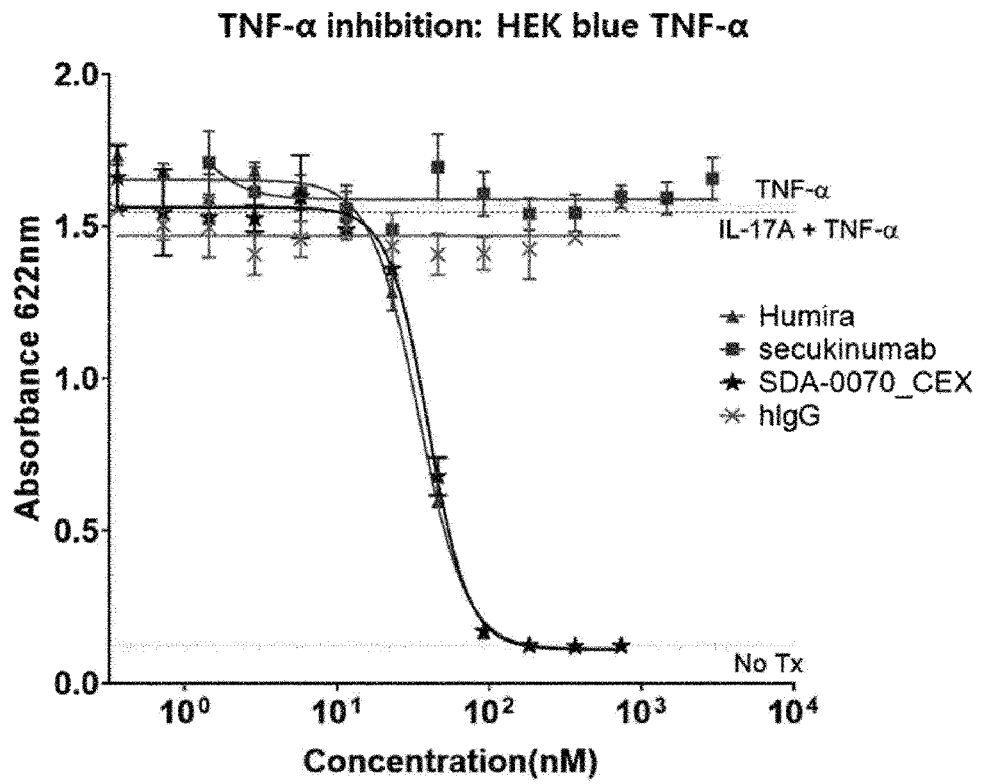

As a result of the test for comparing the neutralization property of HEK Blue for SDA-0070_CEX purified product, more excellent efficacy than secukinumab, which is a monospecific antibody for IL-17A, was shown while efficacy similar to Humira, which is a monospecific antibody for TNF-α, was shown (FIGS. 5a and 5b and Table 8). In the following Table 8, IC50 results of SDA-7000 using HEK Blue cell lines are given.

TABLE 8

| Name | IL-17A $IC_{50}$ (pM) | TNF-α $IC_{50}$ (pM) |
|---|---|---|
| Humira | | 34.35 |
| Secukinumab | 229.2 | |
| SDA-0070_CEX | 58.04 | 39.87 |

Example 8: Evaluation of Substance Efficacy Equivalence Depending on Purification Method by Using HT-29 Cell Analysis 8-1: Purification by Cation Exchange Chromatography To improve the purification process of the bispecific antibody, a cation exchange chromatography (CEX) column (Thermofisher Scientific Poros, U.S.A) was used in addition to the gel filtration chromatography (GFC) column which has been used before (GE Healthcare, England).

After filling the column with cation exchange chromatography resin (Thermo, U.S.A), the column was connected with AKTA Pure L (GE Healthcare, U.S.A) equilibrated with sodium acetate as mobile phase A. By flowing mobile phase A in an amount of 5 CV, equilibration was performed. The first purified product was dialyzed against mobile phase A, and, after filtering through 0.22 μm syringe filter (Millipore, U.S.A), injected to the column. By flowing mobile phase A in an amount of 5 CV, non-adhered proteins were removed. By flowing mobile phase B (mobile phase A+1 M NaCl) according to concentration gradient, loaded proteins were eluted. The eluent was added to a dialysis bag (Spectrumlabs) and then dialyzed 2 times with an interval of 4 hours at least against DPBS (Welgene Inc., South Korea). The dialyzed proteins were concentrated to 20 mg/mL or higher by using Amicon Ultra-15 (Millipore, UFC905096), and then subjected to sterile-filtration using 0.22 μm syringe filter (Millipore, SLGP033RB).

8-2: Comparison of Neutralization Property Depending on Purification Method

By comparing co-neutralization property for IL-17A and TNF-α in HT-29 cells between the purified product of antibody sample using GFC column (GE Healthcare, England) and the purified product of antibody sample using GFC column CEX column (Thermofisher Scientific Poros, U.S.A), equivalency test was carried out to examine whether or not a difference in purification method exhibits any effect on the efficacy.

For the test, HT-29 cell line (*Homo sapiens* colorectal adenocarcinoma) (South Korea Cell Line Bank, South Korea) obtained after at least 3 subcultures using RPMI1640

(Hyclone, U.S.A) medium containing 10% fetal bovine serum (Gibco, U.S.A), 1% antibiotics, and anti-anti (penicillin/streptomycin/anti-mycoplasma; Gibco, U.S.A) were used.

IL-17A (R&D systems, U.S.A) and TNF-α (R&D systems, U.S.A) were diluted, respectively, and the antibody sample was diluted from 736 pM to 0.7 pM, i.e., 4 times for each dilution, so that the treatment can be carried out with total 6 concentrations. Each diluted antibody and diluted antigen were admixed in a 96-well plate and reacted at 37° C. for 1 hour. The plate upon completion of the antigen-antibody reaction was subjected to trypsin-EDTA treatment. HT-29 cells collected after the treatment were seeded at $7.5 \times 10^4$ cells/well and cultured for 48 hours in an environment of 37° C., 5% $CO_2$. After 48 hours, culture medium except the cells was collected. CXCL-1 concentration in the collected culture medium was measured by using ELISA kit Human CXCL-1 (R&D systems, U.S.A) so that the neutralization property of antibody against each antigen was evaluated.

Figure 6:
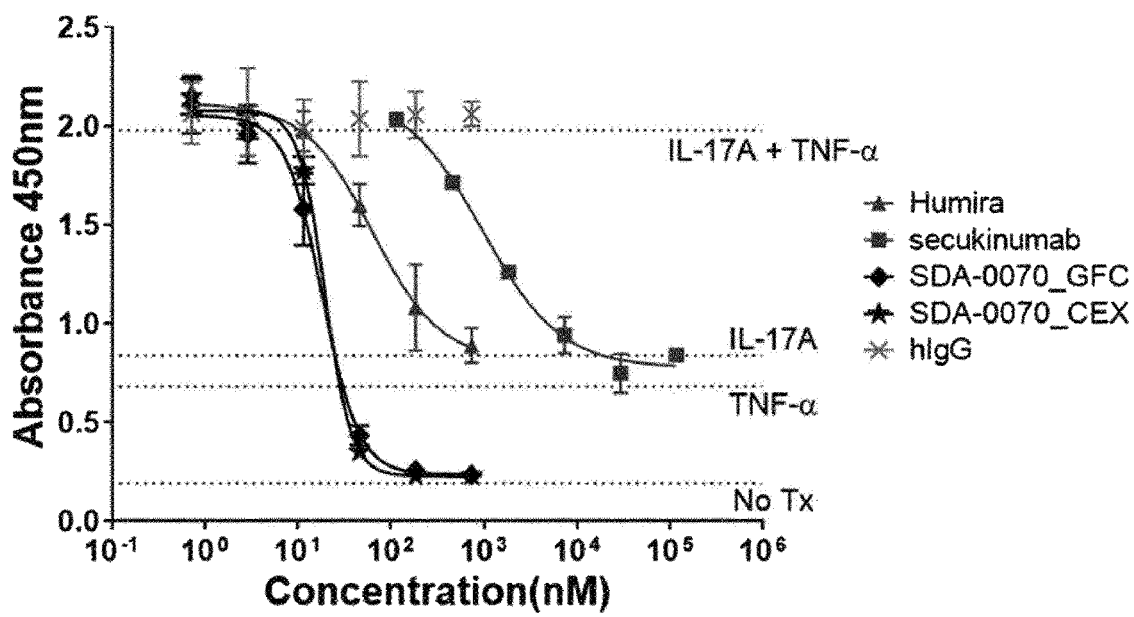
FIG. 6 shows the result of evaluating the equivalence by determining the neutralization property depending on the method of purifying SDA-0070, in which the determination was made by using human HT-29 cells.

As a result of measuring the co-neutralization property for IL-17A and TNF-α of the antibody samples against HT-29 cells, it was found that the co-neutralization property is maintained at similar level between the sample purified by GFC column and the sample purified by CEX column (FIG. 6 and Table 9). In the following Table 9, the result of evaluating the efficacy using HT-20 cells depending on the purification method of GFC or CEX is given.

TABLE 9

| Name | IC50 (pM) |
| --- | --- |
| Humira | 63.19 |
| Secukinumab | 960.7 |
| SDA-0070_GFC | 18.2 |
| SDA-0070_CEX | 19.56 |

Example 9: Evaluation of Substance Efficacy Equivalence Between Sample Derived from HEK293 and Sample Derived from CHO-S by Using HT-29 Cell Analysis By using SDA-0070_CEX as an antibody sample produced based on HEK293 transient expression system and SDA-0070_RD1601 sample produced based on CHO-S cell line system followed by $2^{nd}$ CEX purification, the neutralization property in HT-29 cells was evaluated and the efficacy equivalence was compared between the different cell lines used for production.

For the test, HT-29 cells were subcultured 3 or more times using a medium containing 10% fetal bovine serum (Gibco, U.S.A), 1% antibiotics, and Anti-anti (penicillin/streptomycin/anti-mycoplasma; Gibco, U.S.A) and used. The neutralization property test was conducted for the three types, i.e., neutralization property for IL-17A only, neutralization property for TNF-α only, and co-neutralization property for IL-17A and TNF-α. For testing the neutralization property for IL-17A only, IL-17A (R&D, U.S.A) was diluted to have final concentration of 3.75 ng/ml and, for testing the neutralization property for TNF-α only, TNF-α (R&D, U.S.A) was diluted to have final concentration of 1.17 ng/ml. For testing the co-neutralization property for IL-17A and TNF-α, IL-17A was diluted to have final concentration of 2.5 ng/ml and TNF-α was diluted to have final concentration of 0.39 ng/ml. The antibody sample was diluted, by 2 times for each dilution, from 736 pM to 0.36 pM so that the treatment can be carried out with total 12 concentrations. The diluted antibody and diluted antigen were admixed in a 96-well plate and reacted at 37° C. for 1 hour. The plate upon completion of the antigen-antibody reaction was subjected to trypsin-EDTA treatment. HT-29 cells collected after the treatment were seeded and cultured for 48 hours in an environment of 37° C., 5% $CO_2$. After 48 hours, culture medium except the cells was collected. CXCL-1 concentration in the collected culture medium was measured by using ELISA kit Human CXCL-1 (R&D systems, U.S.A) so that the neutralization property of antibody against antigen was evaluated.

Figure 7A:
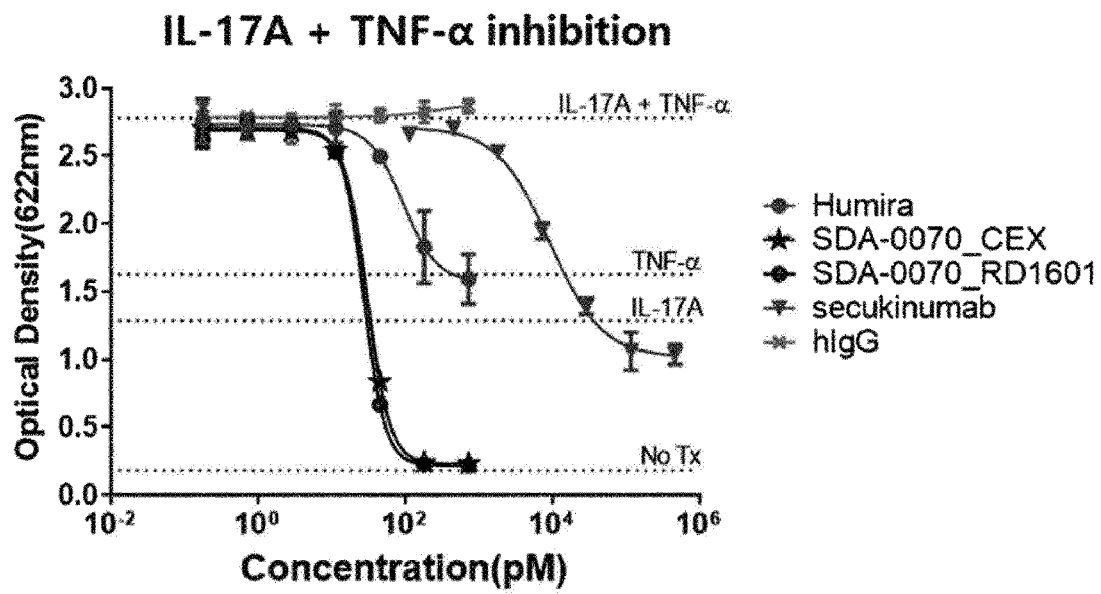
FIGS. 7a to 7c show the result of evaluating the efficacy equivalence between a transient expression product of SDA-0070 prepared from human HT-29 cells and a mass production product prepared by using stabilized cells.
Figure 7B:
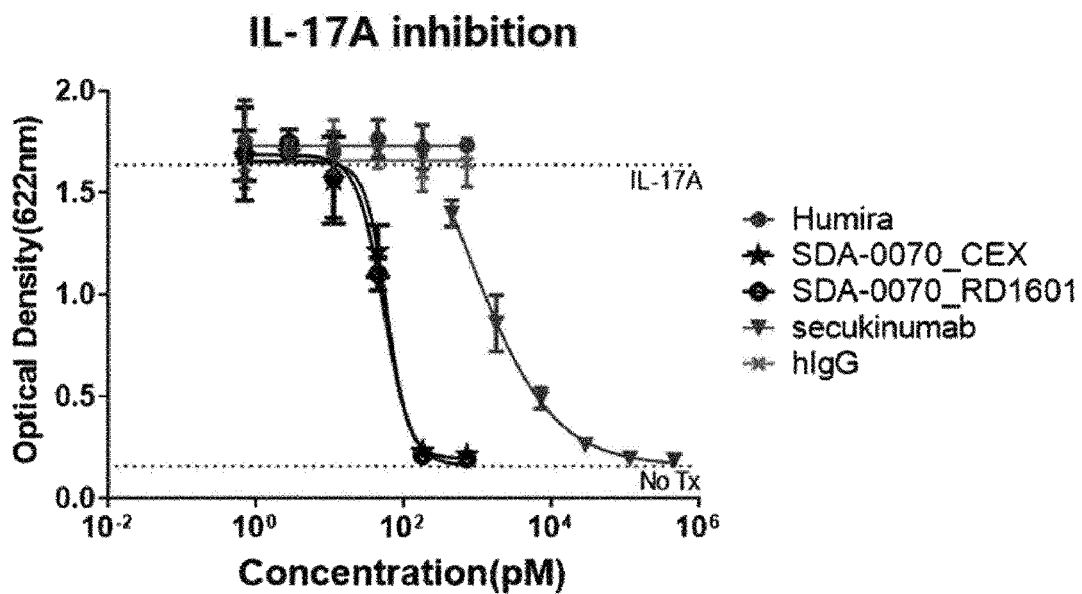
Figure 7C:
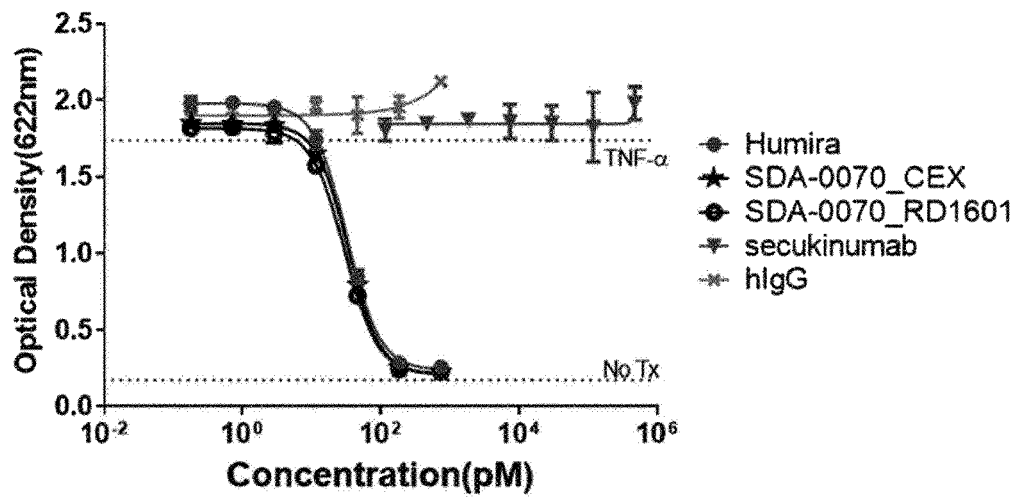

As a result of comparing the neutralization property between SDA-0070_CEX as a sample produced based on HEK293 transient expression system and SDA-0070_RD1601 sample produced based on CHO-S cell line system in the same clone, it was found that there is no difference in the neutralization property for IL-17 and TNF-α (FIGS. 7a to 7c, and Table 10). In the following Table 10, the result of comparing production efficacy between the different production systems is shown, in which the production has been made by using HT-29.

TABLE 10

| Name | IL-17A + TNF-α $IC_{50}$ (pM) | IL-17A $IC_{50}$ (pM) | TNF-α $IC_{50}$ (pM) |
| --- | --- | --- | --- |
| Humira | 95.09 | | 32.38 |
| SDA-0070_CEX | 30.86 | 60.53 | 33.63 |
| SDA-0070_RD1601 | 27.67 | 55.16 | 30.16 |
| Secukinumab | 9303 | 804.6 | |

Example 10: Evaluation of Substance Efficacy Equivalence Between Sample Derived from HEK293 and Sample Derived from CHO-S by Using Reporter Cell Analysis By using SDA-0070_CEX as an antibody sample produced based on HEK293 transient expression system and SDA-0070_RD1601 sample produced based on CHO-S cell line system, the neutralization property in HEK blue derived cells was evaluated and the efficacy equivalence was compared between the different cell lines used for production.

By using HEK-Blue™ IL-17 cell line expressing IL-17RA and IL-17RC as IL-17 receptor (Invivogen, U.S.A) and HEK-Blue™ TNF-α cell line (Invivogen, U.S.A) expressing TNFRI and TNFRII as TNF-α receptor, the neutralization property for IL-17A and TNF-α was evaluated. For culture of HEK-Blue cell lines, DMEM-HG (Hyclone, U.S.A) containing 10% fetal bovine serum (Gibco, U.S.A), 1% antibiotics, and Anti-anti (penicillin/streptomycin/anti-mycoplasma; Gibco, U.S.A) was used. As a selection antibiotic for maintaining the expression of each receptor and SEAP, zeocin (Invivogen, U.S.A) was commonly used. For HEK-Blue™ IL-17 cell line, HEK-Blue™ Selection (Invivogen, U.S.A), which is a mixture of antibiotics, was additionally used. All cells used for the test were the cells which have been subcultured at least 3 times, and, when recovering the cells from a culture plate, Accutase (Merck Millipore, Germany) was used. A diluted product of each antigen was prepared such that IL-17A (R&D, U.S.A, 7955-IL-025/CF) has final concentration of 0.6 ng/ml and TNF-α (R&D, U.S.A, 210-TA-020/CF) has final concentration of 0.4 ng/ml. Each antibody sample was diluted, 2 times for each dilution, starting from 736 pM to 0.36 pM so that the treatment can be made with total 12 concentrations. The diluted antibody and diluted antigen were admixed with each other in a 96-well plate followed by reaction for 1 hour at 37° C. The HEK-Blue™ IL-17 cells and HEK-Blue™ TNF-α cells recovered by Accutase were seeded, at 5×10$^4$ cells per well, to the plate having completed antigen-antibody reaction and cultured for 24 hours in an environment of 37° C., 5% $CO_2$. After 24 hours, culture medium except the cells was collected. To the collected culture medium, QUANTI-Blue™ medium (Invivogen, U.S.A) solution was added and cultured at 37° C. Then, depending on the resulting substrate reaction rate, absorbance at 622 nm was measured within 20 minutes to 60 minutes by using Multiskan™ GO Microplate Spectrophotometer (Thermofisher Scientific, U.S.A).

Figure 8A:
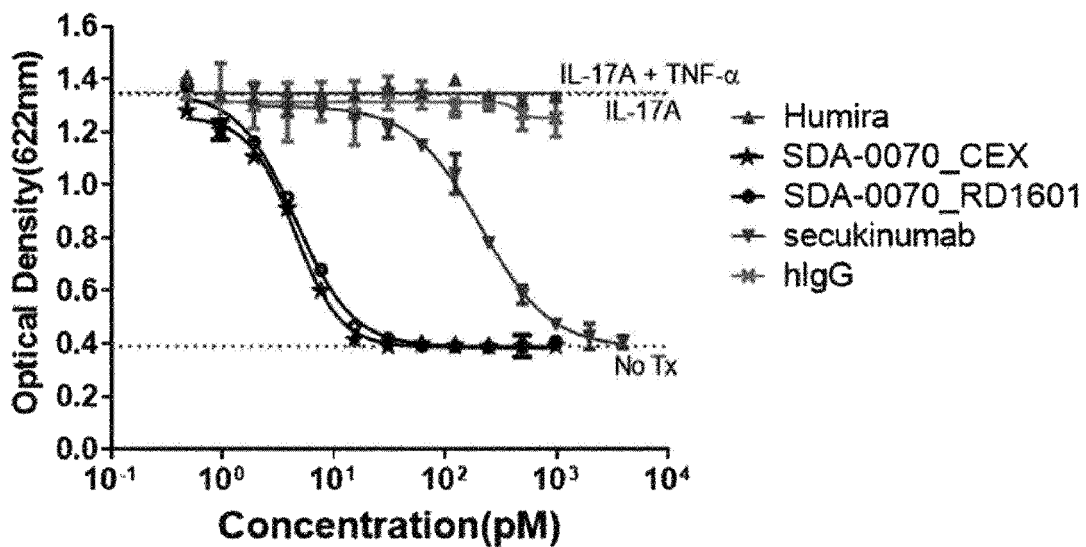
FIGS. 8a and 8b show the result of evaluating the efficacy equivalence between a transient expression product of SDA-0070 prepared from HEK blue derived cells and a mass production product prepared by using stabilized cells.
Figure 8B:
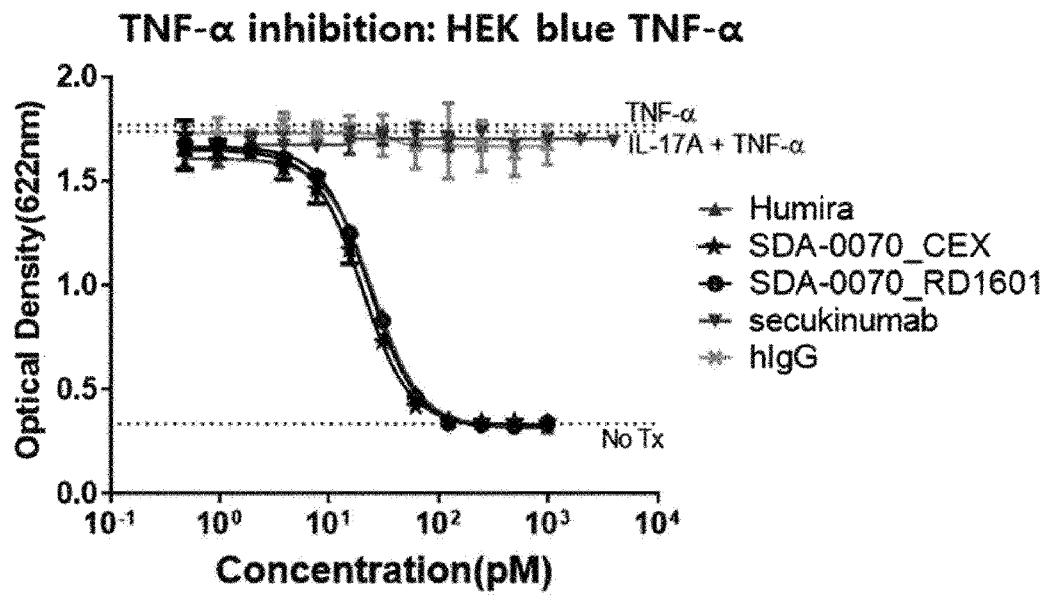

As a result of comparing the neutralization property between SDA-0070_CEX as a sample produced based on HEK293 transient expression system and SDA-0070_RD1601 sample produced based on CHO-S cell line in same clone, it was found that there is no difference in the efficacy between the two proteins having different cell origin (FIGS. 8a and 8b, and Table 11). In the following Table 11, the result of comparing efficacy of each protein by using HEK blue derived cells is given.

TABLE 11

| Name | IL-17A IC$_{50}$ (pM) | TNF-α IC$_{50}$ (pM) |
| --- | --- | --- |
| Humira | | 25.26 |
| SDA-0070_CEX | 4.456 | 19.83 |
| SDA-0070_RD1601 | 4.542 | 23.26 |
| Secukinumab | 208.3 | |

Example 11: Evaluation of Antibody Affinity for Human FcRn Antigen

By using Octet QK analyzer (Fortebio Inc, U.S.A), affinity of the antibodies for human or monkey FcRn (Sinobiological, China) antigen was measured. With Octet analyzer, a thickness change in protein layer bound to the surface of a biosensor is measured by using BLI (Bio-Layer Interferometry) principle, so that the state of binding between a protein and other biological molecule can be monitored in real time.

Using Ni-NTA biosensor coated with nickel (Fortebio Inc, 18-5101), human or monkey FcRn-His antigen having a histidine residue linked to the protein C-terminal was immobilized. Then, antibody Humira and SDA-0070, prepared at different concentrations, were separately bound thereto, and then affinity was measured.

As a result of examining the affinity of all antibodies for human FcRn, it was found that SDA-0070 has binding rate (Kon) of 1.6×10$^6$ 1/Ms at pH 6.0, showing binding rate which is similar to the rate of Humira having normal IgG structure. Meanwhile, SDA-0070 has dissociation rate (Kdis) of less than 1×10$^{-3}$ 1/s. KD was, being affected by a small difference in the dissociation rate (Kdis), 6.4×10$^{-10}$ M or so for Humira and 5.0×10$^{-10}$ M for SDA-0070. In an environment with pH 7.4, the dissociation rate (Kdis) of SDA-00070 was 5.83×10$^{-3}$ 1/s, which is similar to Humira. Moreover, from monkey FcRn, an analysis result similar to human FcRn was obtained. In spite of a structural difference in bispecific antibody, FcRn affinity similar to IgG with normal structure was exhibited. In the following Table 12, kinetic parameters of SDA-0070 for human FcRn and monkey FcRn are given.

TABLE 12

| Analyte Immobilize | | Dissociation pH | Humira | SDA-0070 |
| --- | --- | --- | --- | --- |
| hFcRN-C-His | $K_D$ (M) | pH 6.0 | 6.42 × 10$^{-10}$ | 5.06 × 10$^{-10}$ |
| | $K_{on}$ (1/Ms) | | 1.63 × 10$^6$ | 1.69 × 10$^6$ |
| | $K_{dis}$ (1/S) | | 1.05 × 10$^{-3}$ | 8.56 × 10$^{-4}$ |
| hFcRN-C-His | $K_D$ (M) | pH 7.4 | 6.32 × 10$^{-9}$ | 9.08 × 10$^{-9}$ |
| | $K_{on}$ (1/Ms) | | 8.61 × 10$^5$ | 6.41 × 10$^5$ |
| | $K_{dis}$ (1/S) | | 5.44 × 10$^{-3}$ | 5.83 × 10$^{-3}$ |
| cynoFcRN-C-His | $K_D$ (M) | pH 6.0 | 5.99 × 10$^{-10}$ | 4.61 × 10$^{-10}$ |
| | $K_{on}$ (1/Ms) | | 1.89 × 10$^6$ | 1.63 × 10$^6$ |
| | $K_{dis}$ (1/S) | | 1.13 × 10$^{-3}$ | 7.50 × 10$^{-4}$ |
| cynoFcRN-C-His | $K_D$ (M) | pH 7.4 | 4.24 × 10$^{-9}$ | 4.46 × 10$^{-9}$ |
| | $K_{on}$ (1/Ms) | | 1.06 × 10$^6$ | 9.43 × 10$^5$ |
| | $K_{dis}$ (1/S) | | 4.49 × 10$^{-3}$ | 4.20 × 10$^{-3}$ |

Example 12: Evaluation of Binding of SDA-0070 to Major Proteins Related to ADCC

To evaluate the binding strength of SDA-0070 related to antibody-dependent cell mediated cytotoxicity (ADCC), indirect-ELISA was carried out. ADCC is a phenomenon in which Fc region of an antibody bound to a surface of a target cell is recognized by NK cells and cytotoxicity is exhibited against the cell as a target. CD16, CD64, and the like present on a surface of NK cells bind to Fc of an antibody to trigger an activation signal, and induce cell apoptosis accordingly.

To evaluate the binding of SDA-0070 to CD64 and CD16, Humira (Abbvie, U.S.A) and one type of antibody in IgG1 form (Sigma Aldrich, U.S.A) were used as a positive condition antibody. As a negative condition antibody, one type of IgG4 (Sigma Aldrich, U.S.A) antibody was also used. Recombinant human Fc gamma RIIIA/CD16a protein (1 μg/ml, R&D systems, U.S.A), recombinant human Fc gamma RI/CD64 protein (R&D systems, U.S.A), and BSA (Sigma Aldrich, U.S.A) were treated, each in 100 μl, on a 96-well plate (NUNC, 96 well plat bottom) by using DPBS, and then the reaction was allowed to occur for 12 hours to have coating. The aforementioned antibody group for binding test was serially diluted, i.e., 4 times for each dilution starting from 1380 nM, and the reaction was allowed to occur for 2 hours. Then, a treatment with the secondary antibody Peroxidase-AffiniPure F(ab')2 Fragment Goat Anti-Human IgG, F(ab')2 Fragment Specific (Jackson Immune research, U.S.A) was performed followed by a reaction for 1 hour. Next, color development was performed by a treatment with TMB, and the substrate reaction was terminated by a treatment with $H_2SO_4$. Absorbance at 450 nm was then measured by using a spectrophotometer (Thermo Scientific, U.S.A).

Figure 9:
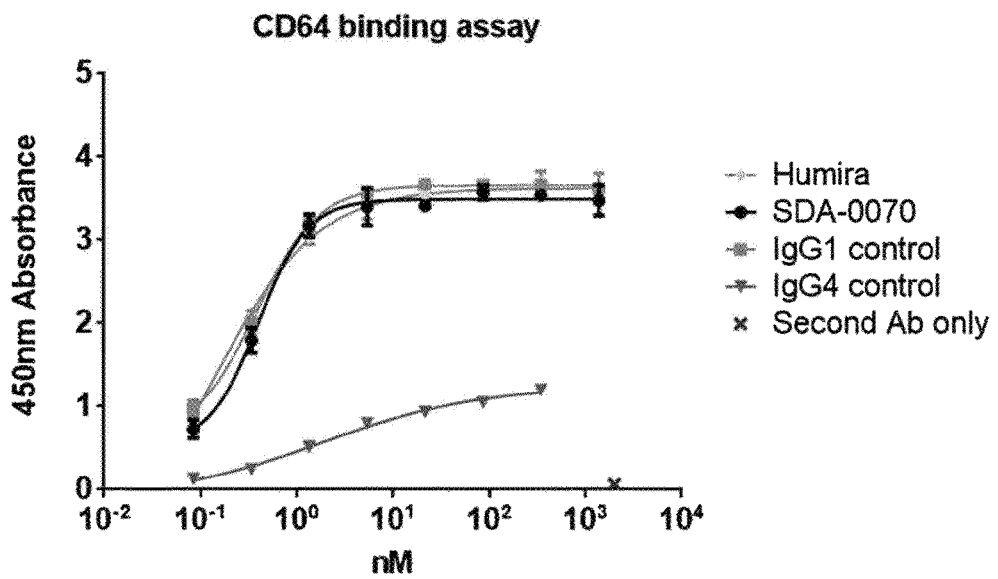
FIG. 9 shows the result of examining the CD64 binding strength for ADCC analysis of SDA-0070.

As a result of measuring the binding level of the Fc part of antibody group to CD64 derived from NK cells, it was found that the binding strength of SDA-0070 is similar to the binding strength of Humira and IgG1 as control (FIG. 9).

Figure 10:
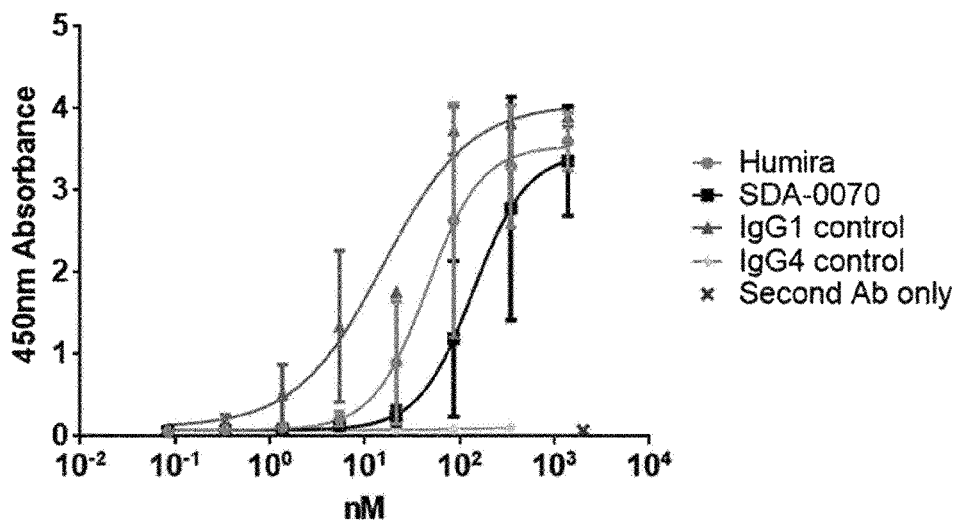
FIG. 10 shows the result of examining the CD16a binding strength for ADCC analysis of SDA-0070.
Figure 11:
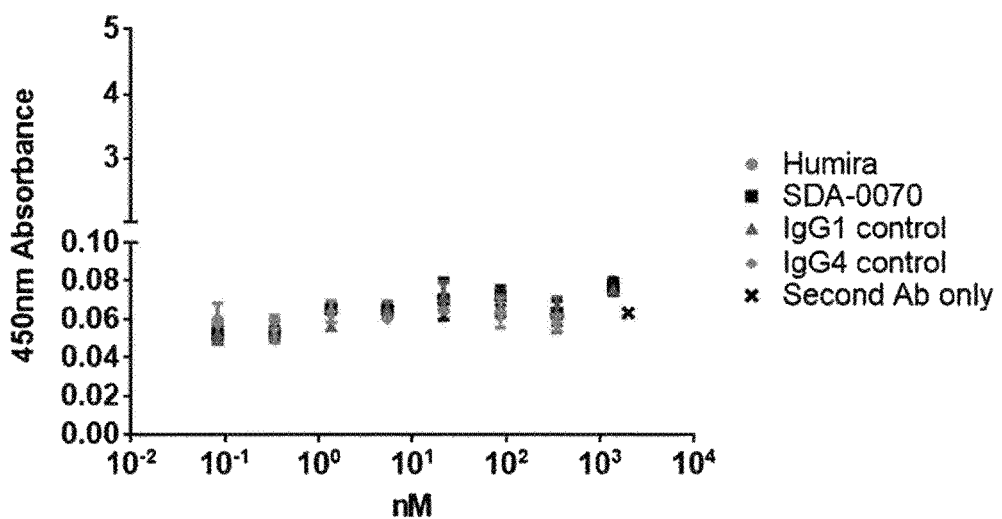
FIG. 11 shows the result of examining the BSA binding strength for ADCC analysis of SDA-0070.

Moreover, with regard to the binding strength of the antibody group to CD16a, IgG1 control exhibited the most excellent result followed by SDA-7000 and Humira antibody, which showed a similar result (FIG. 10). In terms of the BSA binding strength, it was found that both SDA-0070 and control antibody show no response (FIG. 11).

Example 13: Co-Binding Property of SDA-0070 to IL-17A and TNF-α

By using OCTET as described below, co-binding pattern of SDA-7000 to TNF-α and IL-17A was determined in real time.

Figure 12:
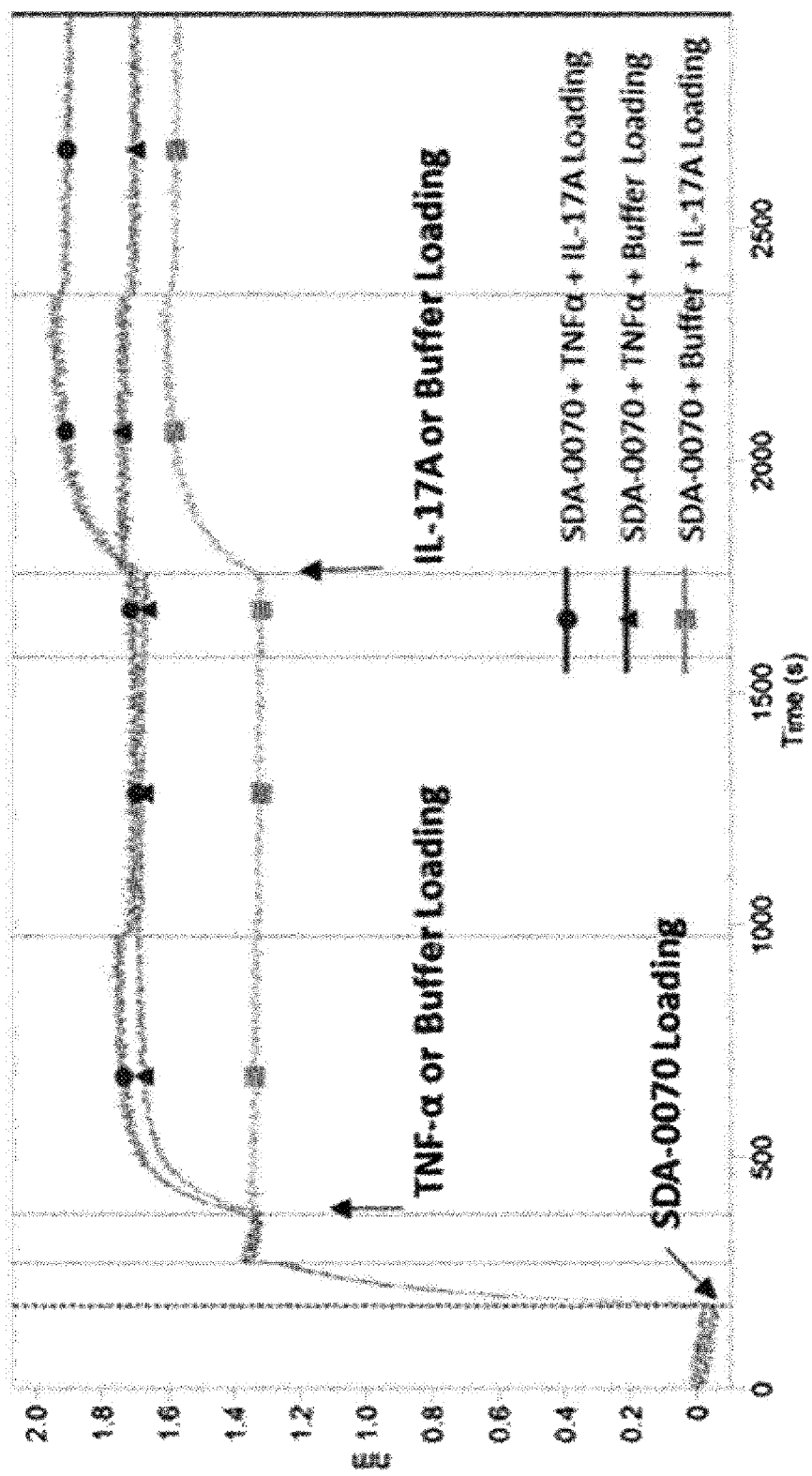
FIG. 12 shows the result of examining the co-binding property of SDA-0070 to IL-17A and TNF-α.

Specifically, Octet QK analyzer (Fortebio Inc, U.S.A) was used, and the antibody was allowed to bind to AHC biosensor (Fortebio Inc, U.S.A) via Fc region. SDA-0070 was diluted at a concentration of 10 μg/ml in 1× Kinetics buffer (Fortebio Inc, U.S.A) and then loaded to the AHC biosensor for binding. After a stabilization period, unbound state of SDA-7000 bound to the sensor was determined. According to various conditions, a treatment only with 20 nM TNF-α (Peprotech, U.S.A) or Kinetics buffer was performed, and TNF-α binding was compared between them in real time. Thereafter, at various conditions, a treatment only with 15 nM IL-17A (R&D systems, U.S.A) or Kinetics buffer was performed, and IL-17A binding was compared between them in real time As a result, it was found based on the real-time data that SDA-0070 simultaneously recognizes and binds to both antigens, which is the same result as the result obtained by ELISA (FIG. 12).

Example 14: Analysis of Neutralization Property of Anti IL-17A Antibody and Anti TNF-α Antibody Commercially available RA-FLS cells (Cell Application, U.S.A) known to allow induced expression of hIL-6, i.e., an inflammatory cytokine, by TNF-α or IL-17A were seeded at $2 \times 10^4$ cells/well to a 96-well cell culture plate containing human cynoviocyte medium (Cell application, U.S.A) and cultured for 24 hours in an environment of 37° C., 5% $CO_2$. In this example, SDA-7000 was evaluated together with TNF-α monospecific antibody Humira (Abbvie, U.S.A), IL-17A monospecific antibody secukinumab (Novartis, Switzerland), and TNF-α and IL-17A bispecific antibody LY3114062 (Eli Lilly, WO2014137961, U.S.A). To 1.87 ng/ml hTNF-α (R&D system, U.S.A) or 18.7 ng/ml hIL-17A (R&D system, U.S.A), secukinumab antibody as an anti IL-17A was added after serial dilution by 4 times starting from 17664 pM, and SDA-0070, LY3114062 or Humira as anti TNF-α antibody was added after serial dilution starting from 4416 pM. Then, each mixture was reacted for 1 hour at 37° C.

The mixture was treated with RA-FLS cells which have been cultured as described above and cultured with the cells for 24 hours. Then, only the culture medium was collected and treated with ELISA kit for measuring hIL-6 (R&D system, U.S.A). Expression amount of hIL-6 was measured by using a spectrophotometer (Multiskan G O, Thermo Scientific, U.S.A).

Figure 13:
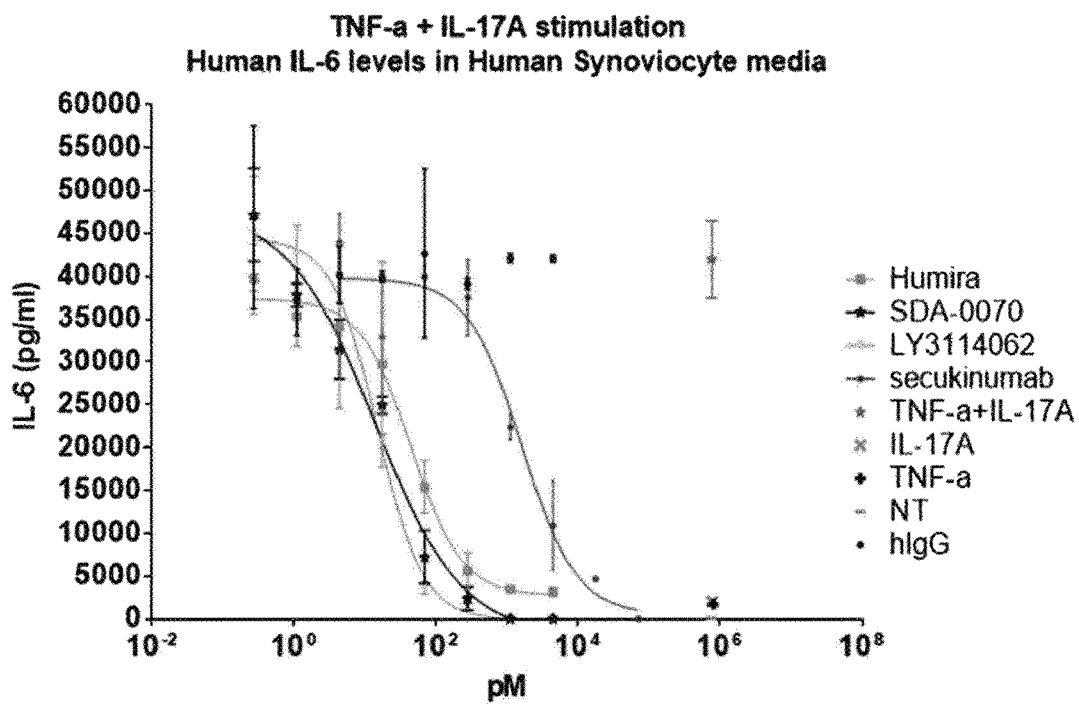
FIG. 13 shows the result of evaluating the co-neutralization property of SDA-0070 for IL-17A and TNF-α in commercially available RA-FLS cells.
Figure 14:
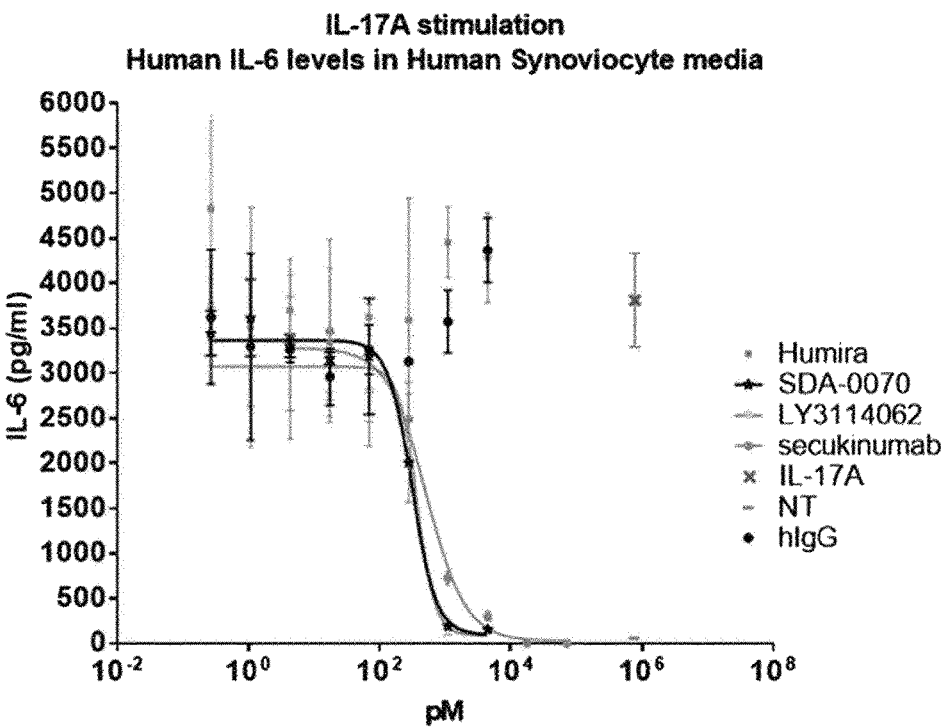
FIG. 14 shows the result of evaluating the neutralization property of SDA-0070 for IL-17A in commercially available RA-FLS cells.
Figure 15:
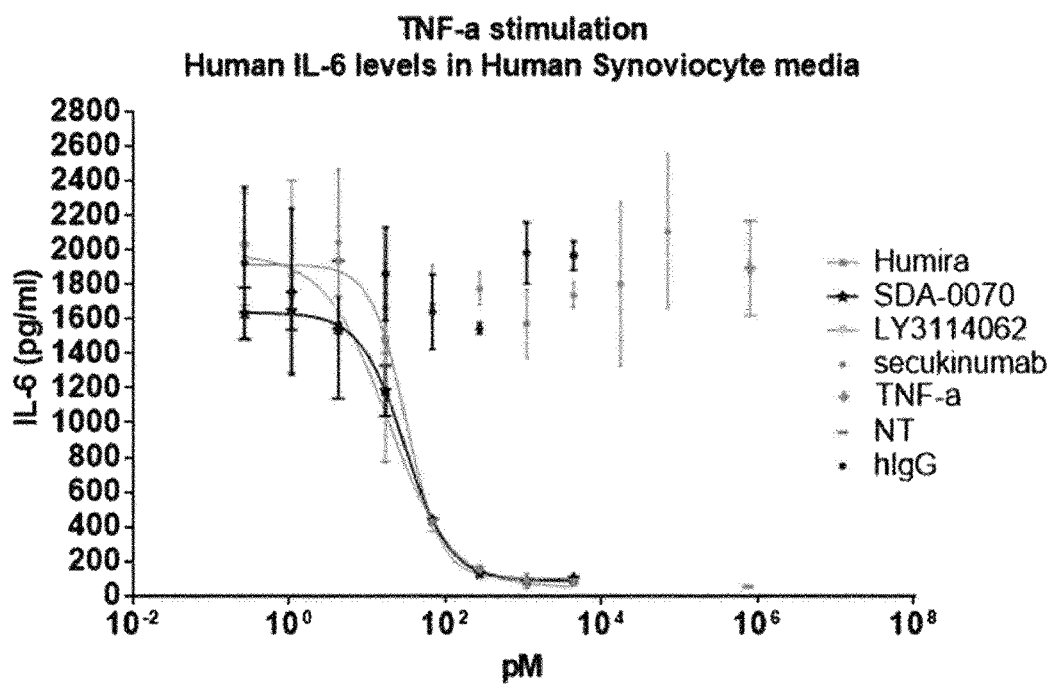
FIG. 15 shows the result of evaluating the neutralization property of SDA-0070 for TNF-α in commercially available RA-FLS cells.

As a result, it was found that SDA-0070 bispecific antibody exhibits higher activity of inhibiting IL-6 secretion compared to the group treated with monospecific anti IL-17 antibody or monospecific anti TNF-α antibody (FIG. 13 to FIG. 15, and Table 13 to Table 15).

TABLE 13

Result of evaluating co-neutralization property for IL-17A and TNF-α in commercially available RA-FLS cells

|  | Humira | SDA-0070 | LY3114062 | Secukinumab |
|---|---|---|---|---|
| $IC_{50}$ (pM) | 44.10 | 13.72 | 14.85 | 1614 |

TABLE 14

Result of evaluating neutralization property for IL-17A in commercially available RA-FLS cells

|  | Humira | SDA-0070 | LY3114062 | Secukinumab |
|---|---|---|---|---|
| $IC_{50}$ (pM) | — | 312.4 | 371.5 | 519.1 |

TABLE 15

Result of evaluating neutralization property for TNF-α in commercially available RA-FLS cells

|  | Humira | SDA-0070 | LY3114062 | Secukinumab |
|---|---|---|---|---|
| $IC_{50}$ (pM) | 31.75 | 30.65 | 18.57 | — |

Example 15: Evaluation of Neutralization Property of SDA-0070 for IL-17A and TNF-α by Using RA-FLS Cells Derived from Patient In this example, instead of using commercially available RA-FLS cells, rheumatoid arthritis-fibroblast like synoviocyte (RA-FLS) was isolated from a patent having rheumatoid arthritis, and it was cultured and used for evaluating the activity of SDA-0070. After finely mincing the synovial membrane tissues, 1 mg/ml Type 2 collagenase (Worthington Biochemical Corporation) was added thereto for having a reaction in Dulbecco's modified Eagle's medium (Welgene Inc. South Korea). After re-floating in DMEM (supplemented with 10% fetal bovine serum (FBS), 1% P/S), cells were filtered using a 40 μm cell strainer, and then adhered on a 100 mm culture dish. Only the adhered cells were cultured again and used.

The isolated and cultured RA-FLS (RA03) cells derived from a patient were inoculated to a 24-well plate at $5 \times 10^4$ cells/ml followed by culture at 37° C. Each cell was then treated with Humira, SDA-0070, or LY3114062, each at $10^3$, $10^2$, $10^1$, $10^0$, $10^{-1}$, $10^{-2}$, or $10^{-3}$ pM. After 1 hour, the cells were treated simultaneously with TNF-α (10 ng/ml, R&D systems, U.S.A) and IL-17A (50 ng/ml, R&D systems, U.S.A). After 48 hours, the cell culture medium was collected. The collected medium was centrifuged for 5 minutes at 3500 rpm to obtain a supernatant, which was then stored in an ultra-low temperature freezer until use for ELISA test. To measure the concentration of IL-6 in cell culture medium, an analysis was made by using Human IL-6 ELISA (R&D systems, U.S.A).

Figure 16A:
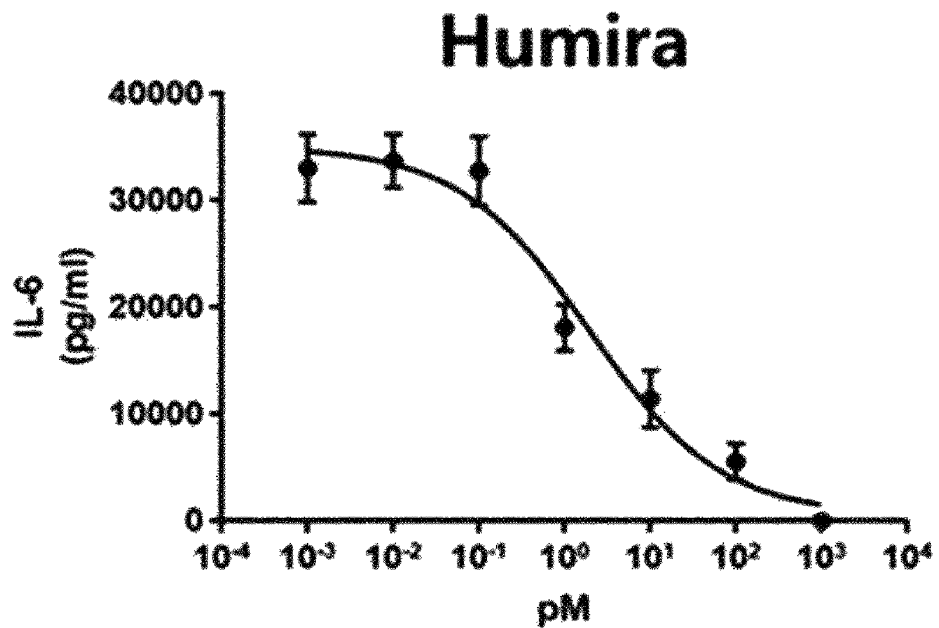
FIGS. 16a to 16c show the result of evaluating the neutralization property of each of Humira, SDA-0070, and LY3114062 for TNF-α and IL-17A in RA-FLS cells that are derived from a patient.
Figure 16B:
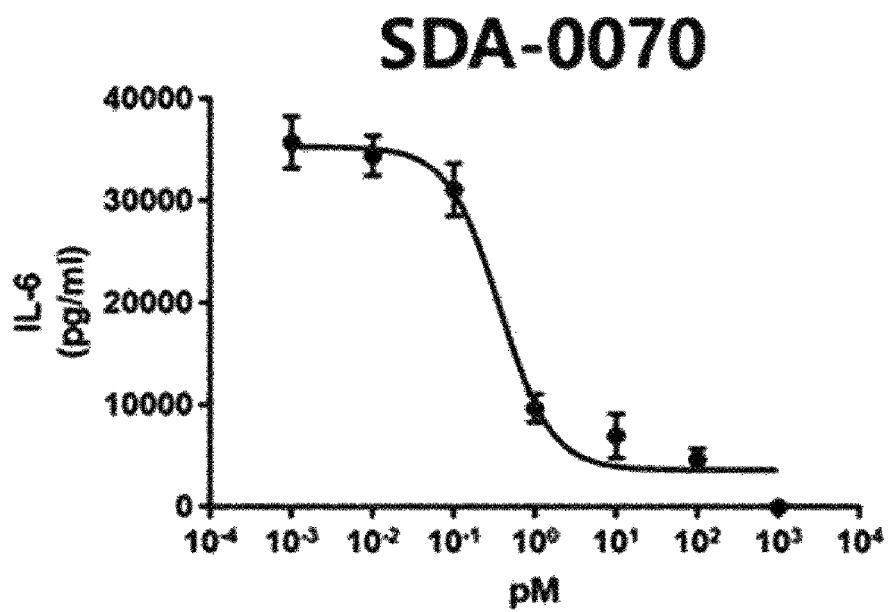
Figure 16C:
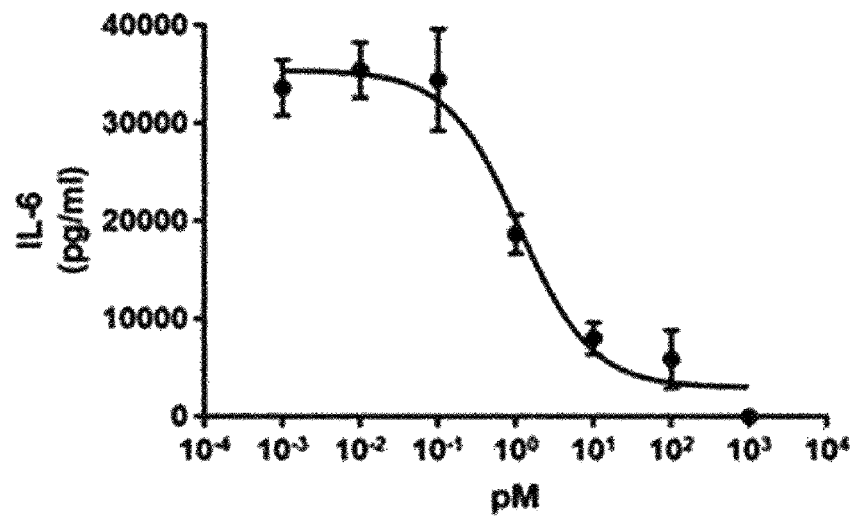

IC50 values (unit: pM) were determined for the antibody treatment groups under the condition of having production of IL-6 induced by TNF-α+IL-17A in RA-FLS (RA03). As a result, the IC50 value was found to be, from the lowest to the highest, in the following order; SDA-0070: 0.3694 pM, LY3114062: 1.420 pM, Humira: 1.966 pM. As a bispecific antibody, SDA-7000 showed the highest activity of simultaneously inhibiting TNF-α and IL-17A, i.e., it was about 3.8 times higher than LY3114062 and about 5 times higher than Humira as a monospecific antibody for TNF-α (FIG. 16a to FIG. 16c).

Example 16: Measurement of Activity of Inhibiting Functions of IL-17A and TNF-α in C57BL/6 Mouse Based on an in vivo test, a change in KC concentration in blood serum caused by IL-17A/TNF-α stimulation according to administration of bispecific antibody was determined.

To a 6-week old male C57/BL6 mouse, PBS, SDA-0070 (40 μg/mouse), LY3114062 (40 μg/mouse), secukinumab (30 μg/mouse), or Humira (30 μg/mouse) was injected (5 animals for each group). After 1 hour, the animal was subcutaneously injected with TNF-α (R&D systems, U.S.A, 0.5 μg/mouse) and IL-17A (R&D system, U.S.A, 6 μg/mouse) and blood was taken 4 hours thereafter. The collected blood was centrifuged for 10 minutes at 5000 rpm to obtain blood serum, which was then stored in an ultra-low temperature freezer. Concentration of KC (CXCL1) was measured by using Quantikine ELISA Mouse CXCL1/KC Immunoassay kit (R&D systems, U.S.A).

A microplate coated with anti mouse KC antibody was treated with the mouse serum diluted in a dilution solution for analysis, and the reaction was allowed to occur for 2 hours at room temperature. After washing 5 times with washing buffer, a treatment with mouse KC Conjugate (100 μl) was performed. After a reaction for 30 minutes, the reaction was terminated with a termination solution, and O.D at 450 nm was measured by using a spectrophotometer.

Figure 17:
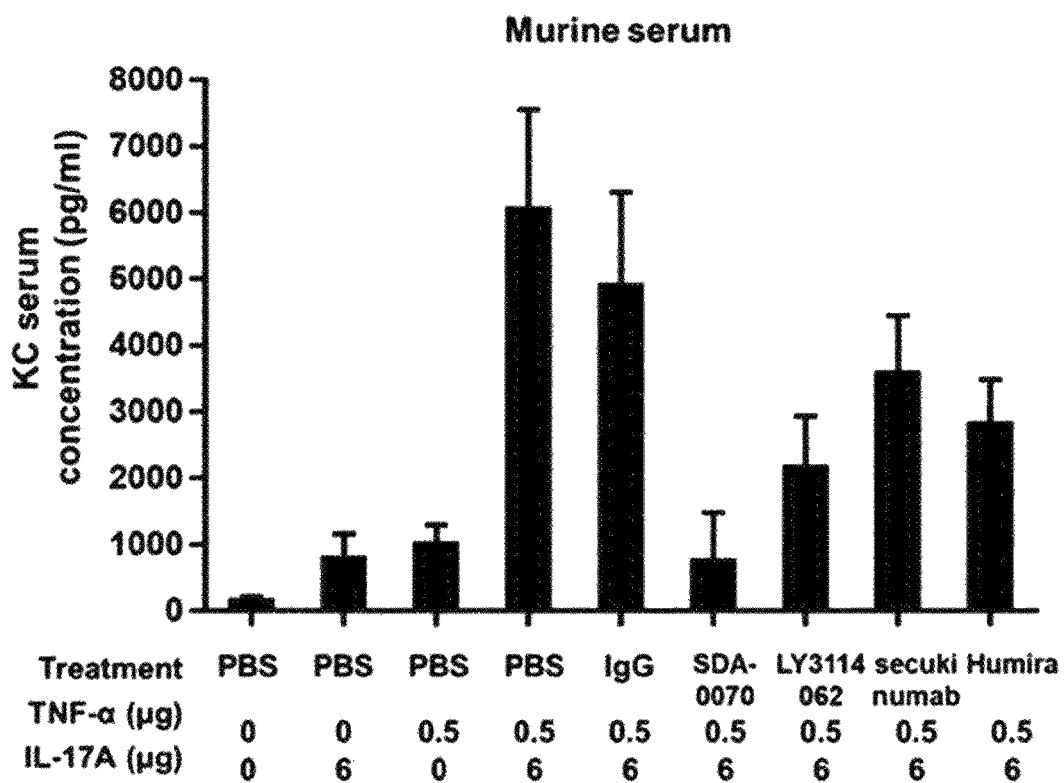
FIG. 17 shows the result of determining the neutralization property of SDA-0070 for TNF-α and IL-17A in C57BL/6 mouse.

As a result, it was found that the all antibody treatment groups exhibit the KC level that is lower in statistically significant sense than the positive control (TNF-α+IL-17A combination only). In particular, SDA-0070 group exhibited the lowest KC level. The SDA-0070 treatment group has more favorable efficacy in statistically significant sense than the Humira treatment group (p=0.0012), and also has more favorable efficacy in statistically significant sense than the LY3114062 treatment group (p=0.0138). In other words, as a result of in vivo determination of a change in KC concentration in blood serum which has been caused by IL-17A/TNF-α stimulation according to administration of bispecific antibody, it was found that SDA-0070 has an excellent neutralization property for both antigens IL-17A and TNF-α (FIG. 17).

The bispecific antibody or an antigen binding fragment thereof according to the present invention exhibits high specificity for IL-17A and TNF-α and more favorable neutralization property compared to monospecific antibody of a prior art, and, by quickly suppressing inflammation and an immune response by inhibiting simultaneously IL-17 and TNF-α, it has an advantage of improving the treatment effect with lower dose.

In the above, specific parts of the content of the present invention are described in detail, but, for a person who has common knowledge in the pertinent art, it would be evident that those specific techniques are only preferred modes of carrying out the invention and by no means the scope of the present invention is limited by them. Thus, the actual scope of the present invention shall be defined by the attached claims and equivalents thereof.

A sequence listing electronically submitted with the present application on Aug. 11, 2021 as an ASCII text file named 20210811_Q59221GR11_TU_SEQ, created on Aug. 9, 2021 and having a size of 51,000 bytes, is incorporated herein by reference in its entirety.

What is claimed is:

1. A bispecific antibody specifically binding to IL-17A (interleukin-17A) and TNF-α (tumor necrosis factor-alpha) comprising an antibody specifically binding to IL-17A or an antigen binding fragment thereof and an antibody specifically binding to TNF-α or an antigen binding fragment thereof characterized in that the antibody specifically binding to IL-17A or an antigen binding fragment thereof contains (i) heavy chain CDR1 of SEQ ID NO: 1, heavy chain CDR2 of SEQ ID NO: 2, and heavy chain CDR3 of SEQ ID NO: 3;
heavy chain CDR1 of SEQ ID NO: 1, heavy chain CDR2 of SEQ ID NO: 4, and heavy chain CDR3 of SEQ ID NO: 5;
heavy chain CDR1 of SEQ ID NO: 1, heavy chain CDR2 of SEQ ID NO: 4, and heavy chain CDR3 of SEQ ID NO: 6;
heavy chain CDR1 of SEQ ID NO: 1, heavy chain CDR2 of SEQ ID NO: 4, and heavy chain CDR3 of SEQ ID NO: 7;
heavy chain CDR1 of SEQ ID NO: 8, heavy chain CDR2 of SEQ ID NO: 9, and heavy chain CDR3 of SEQ ID NO: 10; or
heavy chain CDR1 of SEQ ID NO: 8, heavy chain CDR2 of SEQ ID NO: 11, and heavy chain CDR3 of SEQ ID NO: 10, and (ii) light chain CDR1 of SEQ ID NO: 12; light chain CDR2 of SEQ ID NO: 13; and light chain CDR3 of SEQ ID NO: 14.

2. The bispecific antibody specifically binding to IL-17A and TNF-α according to claim 1, wherein the antibody specifically binding to IL-17A or an antigen binding fragment thereof contains heavy chain variable region framework region (FR) selected from the group consisting of SEQ ID NO: 15 to SEQ ID NO: 26.

3. The bispecific antibody specifically binding to IL-17A and TNF-α according to claim 2, wherein the antibody specifically binding to IL-17A or an antigen binding fragment thereof contains heavy chain variable region FR selected from the group consisting of:
FR1 of SEQ ID NO: 15, FR2 of SEQ ID NO: 16, FR3 of SEQ ID NO: 17 and FR4 of SEQ ID NO: 18;
FR1 of SEQ ID NO: 19, FR2 of SEQ ID NO: 16, FR3 of SEQ ID NO: 20 and FR4 of SEQ ID NO: 21;
FR1 of SEQ ID NO: 22, FR2 of SEQ ID NO: 23, FR3 of SEQ ID NO: 24 and FR4 of SEQ ID NO: 25; and
FR1 of SEQ ID NO: 22, FR2 of SEQ ID NO: 26, FR3 of SEQ ID NO: 24 and FR4 of SEQ ID NO: 25.

4. The bispecific antibody specifically binding to IL-17A and TNF-α according to claim 1, wherein the antibody specifically binding to IL-17A or an antigen binding fragment thereof contains light chain variable region framework region (FR) selected from the group consisting of SEQ ID NO: 27 to SEQ ID NO: 33.

5. The bispecific antibody specifically binding to IL-17A and TNF-α according to claim 4, wherein the antibody specifically binding to IL-17A or an antigen binding fragment thereof contains light chain variable region FR of:
FR1 of SEQ ID NO: 27, FR2 of SEQ ID NO: 28, FR3 of SEQ ID NO: 29 and FR4 of SEQ ID NO: 30; or
FR1 of SEQ ID NO: 31, FR2 of SEQ ID NO: 32, FR3 of SEQ ID NO: 33 and FR4 of SEQ ID NO: 30.

6. The bispecific antibody specifically binding to IL-17A and TNF-α according to claim 1, wherein the antibody specifically binding to IL-17A or an antigen binding fragment thereof contains heavy chain variable region selected from the group consisting of SEQ ID NO: 34 to SEQ ID NO: 39; and light chain variable region of SEQ ID NO: 40 or SEQ ID NO: 41.

7. The bispecific antibody specifically binding to IL-17A and TNF-α according to claim 1, wherein the antibody specifically binding to TNF-α or an antigen binding fragment thereof contains
(i) heavy chain CDR1 of SEQ ID NO: 54, heavy chain CDR2 of SEQ ID NO: 55, and heavy chain CDR3 of SEQ ID NO: 56; and light chain CDR1 of SEQ ID NO: 57, light chain CDR2 of SEQ ID NO: 58, and light chain CDR3 of SEQ ID NO: 59;
(ii) heavy chain CDR1 of SEQ ID NO: 60, heavy chain CDR2 of SEQ ID NO: 61, and heavy chain CDR3 of SEQ ID NO: 62; and light chain CDR1 of SEQ ID NO: 63, light chain CDR2 of SEQ ID NO: 64, and light chain CDR3 of SEQ ID NO: 65;
(iii) heavy chain CDR1 of SEQ ID NO: 66, heavy chain CDR2 of SEQ ID NO: 67, and heavy chain CDR3 of SEQ ID NO: 68; and light chain CDR1 of SEQ ID NO: 69, light chain CDR2 of SEQ ID NO: 70, and light chain CDR3 of SEQ ID NO: 71; or (iv) heavy chain CDR1 of SEQ ID NO: 72, heavy chain CDR2 of SEQ ID NO: 73, and heavy chain CDR3 of SEQ ID NO: 74; and light chain CDR1 of SEQ ID NO: 75, light chain CDR2 of SEQ ID NO: 76, and light chain CDR3 of SEQ ID NO: 77.

8. The bispecific antibody specifically binding to IL-17A and TNF-α according to claim 1, wherein the antibody specifically binding to TNF-α or an antigen binding fragment thereof contains
- (i) heavy chain variable region of SEQ ID NO: 78 and light chain variable region of SEQ ID NO: 79;
- (ii) heavy chain variable region of SEQ ID NO: 80 and light chain variable region of SEQ ID NO: 81;
- (iii) heavy chain variable region of SEQ ID NO: 82 and light chain variable region of SEQ ID NO: 83; or
- (iv) heavy chain variable region of SEQ ID NO: 84 and light chain variable region of SEQ ID NO: 85.

9. The bispecific antibody specifically binding to IL-17A and TNF-α according to claim 8, wherein the antibody specifically binding to TNF-α or an antigen binding fragment thereof is selected from the group consisting of adalimumab, golimumab, certolizumab, and inflixim.

10. The bispecific antibody specifically binding to IL-17A and TNF-α according to claim 1, wherein it contains a heavy chain and a light chain of the antibody specifically binding to IL-17A; and a heavy chain and a light chain of the antibody specifically binding to TNF-α, and C-terminus of heavy chain constant region of the antibody specifically binding to IL-17A is linked to C-terminus of heavy chain constant region of the antibody specifically binding to TNF-α.

11. The bispecific antibody specifically binding to IL-17A and TNF-α according to claim 10, wherein the antibody-antibody linkage is made via a linker.

12. The bispecific antibody specifically binding to IL-17A and TNF-α according to claim 1, wherein it contains an antigen binding fragment of the antibody specifically binding to IL-17A; and a heavy chain and a light chain of the antibody specifically binding to TNF-α, and the antigen binding fragment of the antibody specifically binding to IL-17A is linked to C-terminus of heavy chain constant region of the antibody specifically binding to TNF-α.

13. The bispecific antibody specifically binding to IL-17A and TNF-α according to claim 12, wherein the antigen binding fragment of the antibody is a single-chain variable fragment (scFv).

14. The bispecific antibody specifically binding to IL-17A and TNF-α according to claim 12, wherein the antibody-fragment linkage is made via a linker.

15. A polynucleotide encoding the bispecific antibody or an antigen binding fragment thereof according to claim 1.

16. A vector including the polynucleotide of claim 15.

17. A cell transformed with the vector of claim 16.

18. A method of producing a bispecific antibody or an antigen binding fragment thereof, the method comprising:
- culturing the cell of claim 17; and
- collecting a bispecific antibody specifically binding to IL-17A and TNF-α or an antigen binding fragment thereof from obtained cell culture medium.

19. A pharmaceutical composition for treating an autoimmune disease comprising, as an active ingredient, the bispecific antibody or an antigen binding fragment thereof according to claim 1.

20. The pharmaceutical composition according to claim 19, wherein the autoimmune disease is selected from the group consisting of rheumatoid arthritis, psoriasis, psoriatic arthritis, ankylosing spondylitis, multiple sclerosis, interstitial fibrosis, lupus, glomerulonephritis, Crohn's disease, inflammatory bowel disease, autoimmune eye disease, children arthritis, Behcet's disease, deficiency of the IL-1 receptor antagonist (DIRA), TNF receptor-associated periodic syndrome (TRAPS), neonatal-onset multisystem inflammatory disease (NOMID), familial Mediterranean fever (FMF), and cryopyrin-associated periodic syndrome (CAPS).

21. An antibody-drug conjugate containing the bispecific antibody or an antigen binding fragment thereof according to claim 1, and a drug conjugated thereto.

\* \* \* \* \*